US011191789B2

(12) United States Patent
Kihm et al.

(10) Patent No.: US 11,191,789 B2
(45) Date of Patent: *Dec. 7, 2021

(54) CARTILAGE AND BONE REPAIR AND REGENERATION USING POSTPARTUM-DERIVED CELLS

(75) Inventors: Anthony J. Kihm, Princeton, NJ (US); Agnieszka Seyda, New Brunswick, NJ (US); Sridevi Dhanaraj, Raritan, NJ (US); Ziwei Wang, Monroe, NJ (US); Alexander M. Harmon, Clinton, NJ (US); Ian Ross Harris, Belle Mead, NJ (US); Darin J. Messina, Somerville, NJ (US); Sanjay Mistry, Bedminster, NJ (US); Anna Gosiewska, Skillman, NJ (US); Chin-Feng Yi, Hillsborough, NJ (US)

(73) Assignee: Depuy Synthes Products, Inc., Raynham, MA (US)

( * ) Notice: Subject to any disclaimer, the term of this patent is extended or adjusted under 35 U.S.C. 154(b) by 149 days.

This patent is subject to a terminal disclaimer.

(21) Appl. No.: 10/876,998

(22) Filed: Jun. 25, 2004

(65) Prior Publication Data

US 2005/0019865 A1 Jan. 27, 2005

Related U.S. Application Data

(60) Provisional application No. 60/483,264, filed on Jun. 27, 2003.

(51) Int. Cl.
| | |
|---|---|
| A61K 48/00 | (2006.01) |
| A61K 35/51 | (2015.01) |
| C12N 5/074 | (2010.01) |
| C12N 5/073 | (2010.01) |
| A61K 38/18 | (2006.01) |
| A61K 38/19 | (2006.01) |
| A61K 38/20 | (2006.01) |
| A61K 38/27 | (2006.01) |
| C12N 5/0735 | (2010.01) |
| A61K 35/50 | (2015.01) |
| A61K 35/12 | (2015.01) |

(52) U.S. Cl.
CPC .............. *A61K 35/51* (2013.01); *A61K 35/50* (2013.01); *A61K 38/18* (2013.01); *A61K 38/185* (2013.01); *A61K 38/1808* (2013.01); *A61K 38/1825* (2013.01); *A61K 38/1833* (2013.01); *A61K 38/1841* (2013.01); *A61K 38/1858* (2013.01); *A61K 38/1866* (2013.01); *A61K 38/1891* (2013.01); *A61K 38/19* (2013.01); *A61K 38/204* (2013.01); *A61K 38/2053* (2013.01); *A61K 38/27* (2013.01); *C12N 5/0605* (2013.01); *C12N 5/0606* (2013.01); *C12N 5/0607* (2013.01); *A61K 35/12* (2013.01); *C12N 2500/32* (2013.01); *C12N 2500/34* (2013.01); *C12N 2500/44* (2013.01); *C12N 2500/90* (2013.01); *C12N 2500/95* (2013.01); *C12N 2501/12* (2013.01); *C12N 2501/21* (2013.01); *C12N 2501/23* (2013.01); *C12N 2502/02* (2013.01); *C12N 2506/02* (2013.01); *C12N 2506/03* (2013.01); *C12N 2509/00* (2013.01); *C12N 2533/50* (2013.01)

(58) Field of Classification Search
CPC ................ C12N 5/0605; C12N 5/0607; C12N 2506/03; C12N 2502/02; C12N 2506/02; C12N 2509/00; C12N 2506/025; C12N 5/0668; C12N 2502/03; C12N 2506/1392; C12N 5/0068; C12N 5/0623; C12N 5/0654; C12N 5/0655; C12N 5/0675; A61K 35/51; A61K 35/28; A61K 35/50; A61L 27/3604; A61L 27/3886; A61L 27/3895; A61L 27/54
USPC .................................. 435/325, 455; 424/93.1
See application file for complete search history.

(56) References Cited

U.S. PATENT DOCUMENTS

| | | | |
|---|---|---|---|
| 2,324,800 | A | 7/1943 | Pasternack et al. |
| 2,654,735 | A | 10/1953 | Funk et al. |
| 2,864,848 | A | 12/1958 | McArthur |
| 2,912,332 | A | 11/1959 | Young et al. |
| 3,665,061 | A | 5/1972 | Eberly, Jr. |
| 3,930,954 | A | 1/1976 | Irie et al. |
| 4,193,992 | A | 3/1980 | Fontaine |

(Continued)

FOREIGN PATENT DOCUMENTS

| | | |
|---|---|---|
| EP | 0 333 328 B1 | 12/1993 |
| EP | 1 216 718 | 6/2002 |

(Continued)

OTHER PUBLICATIONS

Luyten et al. Skeletal tissue engineering: opportunities and challenges. Best Pract Res Clin Rheumatol. vol. 15, No. 5, pp. 759-769, Dec. 2001.*

(Continued)

*Primary Examiner* — Michael C Wilson
(74) *Attorney, Agent, or Firm* — Johnson & Johnson

(57) ABSTRACT

Cells derived from postpartum tissue and methods for their isolation and induction to differentiate to cells of a chondrogenic or osteogenic phenotype are provided by the invention. The invention further provides cultures and compositions of the postpartum-derived cells and products related thereto. The postpartum-derived cells of the invention and products related thereto have a plethora of uses, including but not limited to research, diagnostic, and therapeutic applications, for example, in the treatment of bone and cartilage conditions.

15 Claims, No Drawings

(56) References Cited

U.S. PATENT DOCUMENTS

| | | | |
|---|---|---|---|
| 4,216,144 A | 8/1980 | Mead | |
| 4,290,962 A | 9/1981 | Tachi et al. | |
| 4,352,883 A | 10/1982 | Lim | 435/178 |
| 4,393,240 A | 7/1983 | Stille | |
| 4,465,776 A | 8/1984 | Cidlowski et al. | |
| 4,487,865 A | 12/1984 | Balazs et al. | |
| 4,544,516 A | 10/1985 | Hughes et al. | |
| 4,657,866 A | 4/1987 | Kumar | |
| 4,882,162 A | 11/1989 | Ikada et al. | |
| 4,925,667 A | 5/1990 | Fellows et al. | |
| 4,963,489 A | 10/1990 | Naughton et al. | 435/240.1 |
| 5,004,681 A | 4/1991 | Boyse et al. | 435/2 |
| 5,192,553 A | 3/1993 | Boyse et al. | 424/529 |
| 5,248,608 A | 9/1993 | Van Dooren et al. | |
| 5,286,632 A | 2/1994 | Jones | |
| 5,308,763 A * | 5/1994 | Ronnett | C12N 5/062 435/379 |
| 5,320,962 A | 6/1994 | Stiles et al. | |
| 5,342,761 A | 8/1994 | MacLeod | |
| 5,437,994 A | 8/1995 | Emerson et al. | |
| 5,443,950 A | 8/1995 | Naughton et al. | |
| 5,466,233 A | 11/1995 | Weiner et al. | 604/890.1 |
| 5,486,359 A | 1/1996 | Caplan et al. | 424/93.7 |
| 5,580,777 A | 12/1996 | Bernard et al. | |
| 5,589,376 A | 12/1996 | Anderson et al. | |
| 5,670,483 A | 9/1997 | Zhang et al. | 514/14 |
| 5,677,181 A | 10/1997 | Parish | |
| 5,693,332 A | 12/1997 | Hansbrough | |
| 5,698,518 A | 12/1997 | Carson et al. | |
| 5,707,643 A | 1/1998 | Ogura et al. | 424/428 |
| 5,718,922 A | 2/1998 | Herrero-Vanrell et al. | |
| 5,736,516 A | 4/1998 | Louis | 514/12 |
| 5,811,094 A * | 9/1998 | Caplan et al. | 424/93.7 |
| 5,827,735 A | 10/1998 | Young et al. | 435/325 |
| 5,834,308 A | 11/1998 | Peck et al. | 435/325 |
| 5,840,580 A | 11/1998 | Terstappen et al. | |
| 5,842,477 A | 12/1998 | Naughton et al. | |
| 5,843,780 A | 12/1998 | Thompson | |
| 5,843,781 A | 12/1998 | Ballermann et al. | |
| 5,855,619 A | 1/1999 | Caplan et al. | |
| 5,869,079 A | 2/1999 | Wong et al. | 424/426 |
| 5,902,598 A | 5/1999 | Chen et al. | 424/423 |
| 5,902,741 A * | 5/1999 | Purchio et al. | 435/325 |
| 5,906,934 A | 5/1999 | Grande et al. | 435/325 |
| 5,919,702 A * | 7/1999 | Purchio et al. | 435/378 |
| 5,928,214 A | 7/1999 | Rubinstein et al. | |
| 5,942,225 A | 8/1999 | Bruder et al. | 424/93.7 |
| 5,955,343 A | 9/1999 | Holmes et al. | 435/240.1 |
| 5,962,325 A | 10/1999 | Naughton et al. | |
| 5,994,094 A | 11/1999 | Hötten et al. | 435/69.1 |
| 6,001,647 A | 12/1999 | Peck et al. | |
| 6,022,743 A | 2/2000 | Naughton et al. | |
| 6,059,968 A | 5/2000 | Wolf | |
| 6,140,039 A | 10/2000 | Naughton et al. | |
| 6,171,610 B1 | 1/2001 | Vacanti et al. | |
| 6,179,872 B1 | 1/2001 | Bell et al. | |
| 6,200,606 B1 | 3/2001 | Peterson et al. | 424/574 |
| 6,200,806 B1 | 3/2001 | Thomson | |
| 6,214,369 B1 | 4/2001 | Grande et al. | 424/423 |
| 6,221,904 B1 | 4/2001 | Agus et al. | |
| 6,251,090 B1 | 6/2001 | Avery et al. | 604/9 |
| 6,261,600 B1 | 7/2001 | Kirschner et al. | |
| 6,261,841 B1 | 7/2001 | Cohen et al. | |
| 6,291,240 B1 * | 9/2001 | Mansbridge et al. | 435/395 |
| 6,323,188 B1 | 11/2001 | Weissman | |
| 6,326,201 B1 | 12/2001 | Fung et al. | 435/377 |
| 6,331,313 B1 | 12/2001 | Wong et al. | 424/427 |
| 6,333,029 B1 | 12/2001 | Vyakarnam et al. | |
| 6,355,239 B1 | 3/2002 | Bruder et al. | 424/93.1 |
| 6,355,699 B1 | 3/2002 | Vyakarnam et al. | 521/61 |
| 6,358,737 B1 | 3/2002 | Bonewald et al. | |
| 6,372,494 B1 | 4/2002 | Naughton et al. | |
| 6,375,972 B1 | 4/2002 | Guo et al. | 424/423 |
| 6,387,367 B1 | 5/2002 | Davis-Sproul et al. | 424/93.1 |
| 6,391,297 B1 | 5/2002 | Halvorsen | |
| 6,429,013 B1 | 8/2002 | Halvorsen et al. | 435/377 |
| 6,436,704 B1 | 8/2002 | Roberts et al. | 435/366 |
| 6,497,875 B1 | 12/2002 | Sorrell et al. | 424/93.7 |
| 6,511,511 B1 | 1/2003 | Slivka et al. | |
| 6,528,245 B2 | 3/2003 | Sanchez-Ramos et al. | 435/1.1 |
| 6,534,084 B1 | 3/2003 | Vyakarnam et al. | |
| 6,555,374 B1 | 4/2003 | Gimble et al. | 435/371 |
| 6,592,623 B1 | 7/2003 | Bowlin et al. | |
| 6,599,323 B2 | 7/2003 | Melican et al. | 623/23.72 |
| 6,610,535 B1 | 8/2003 | Lu et al. | 435/325 |
| 6,638,765 B1 | 10/2003 | Rosenberg | 435/377 |
| 6,673,606 B1 | 1/2004 | Tennekoon et al. | 435/372 |
| 6,680,198 B1 | 1/2004 | Snyder et al. | 435/368 |
| 6,686,198 B1 | 2/2004 | Melton et al. | 435/377 |
| 6,703,017 B1 | 3/2004 | Peck et al. | 424/93.7 |
| 6,916,655 B2 | 7/2005 | Yasumoto et al. | |
| 7,413,734 B2 | 8/2008 | Mistry et al. | |
| 7,510,873 B2 | 3/2009 | Mistry et al. | |
| 7,524,489 B2 | 4/2009 | Messina et al. | |
| 7,560,276 B2 | 7/2009 | Harmon et al. | |
| 7,790,193 B2 | 7/2010 | Melvik et al. | |
| 7,875,272 B2 | 1/2011 | Messina et al. | |
| 7,875,273 B2 | 1/2011 | Messina et al. | |
| 8,277,796 B2 | 10/2012 | Messina et al. | |
| 8,318,483 B2 | 11/2012 | Mistry et al. | |
| 8,658,152 B2 | 2/2014 | Messina et al. | |
| 8,703,121 B2 | 4/2014 | Harris et al. | |
| 8,790,637 B2 | 7/2014 | Mistry et al. | |
| 8,815,587 B2 | 8/2014 | Harris et al. | |
| 9,234,172 B2 | 1/2016 | Mistry et al. | |
| 2001/0024824 A1 | 9/2001 | Moss et al. | 435/366 |
| 2001/0031256 A1 | 10/2001 | Edge | 424/93.7 |
| 2001/0046489 A1 | 11/2001 | Habener et al. | 424/93.21 |
| 2002/0022676 A1 | 2/2002 | He et al. | 523/113 |
| 2002/0028510 A1 | 3/2002 | Sanberg et al. | 435/368 |
| 2002/0062151 A1 | 5/2002 | Altman et al. | 623/13.7 |
| 2002/0081725 A1 | 6/2002 | Tsang et al. | 435/366 |
| 2002/0098584 A1 | 7/2002 | Palmer et al. | 435/366 |
| 2002/0119565 A1 | 8/2002 | Clarke et al. | 435/366 |
| 2002/0123141 A1 | 9/2002 | Hariri | 435/366 |
| 2002/0150986 A1 | 10/2002 | Lau | |
| 2002/0151056 A1 | 10/2002 | Sasai et al. | 435/368 |
| 2002/0160471 A1 | 10/2002 | Kisiday et al. | 435/177 |
| 2002/0160510 A1 | 10/2002 | Hariri | |
| 2002/0164307 A1 | 11/2002 | Habener et al. | 424/93.7 |
| 2002/0164791 A1 | 11/2002 | Van Der Kooy et al. | 435/366 |
| 2002/0168763 A1 | 11/2002 | Yan et al. | 435/325 |
| 2002/0182241 A1 | 12/2002 | Borenstein et al. | |
| 2002/0182728 A1 | 12/2002 | Ramiya et al. | 435/366 |
| 2002/0187550 A1 | 12/2002 | Dinsmore et al. | 435/377 |
| 2002/0192816 A1 | 12/2002 | Roberts et al. | 435/366 |
| 2003/0003574 A1 | 1/2003 | Toma et al. | 435/368 |
| 2003/0007954 A1 | 1/2003 | Naughton et al. | |
| 2003/0022369 A1 | 1/2003 | Fillmore et al. | 435/371 |
| 2003/0031657 A1 | 2/2003 | Habener et al. | 424/93.21 |
| 2003/0032178 A1 | 2/2003 | Hariri | 435/366 |
| 2003/0032179 A1 | 2/2003 | Hariri et al. | |
| 2003/0032183 A1 | 2/2003 | Sheridan | 435/370 |
| 2003/0049837 A1 | 3/2003 | Weiss et al. | 435/368 |
| 2003/0059939 A1 | 3/2003 | Page et al. | 435/366 |
| 2003/0082155 A1 | 5/2003 | Habener et al. | 424/93.21 |
| 2003/0082160 A1 | 5/2003 | Yu et al. | 424/93.21 |
| 2003/0096409 A1 | 5/2003 | Yasumoto et al. | 435/371 |
| 2003/0104997 A1 | 6/2003 | Black et al. | 514/12 |
| 2003/0109036 A1 | 6/2003 | Wu | 435/366 |
| 2003/0113910 A1 | 6/2003 | Levanduski | 435/325 |
| 2003/0118566 A1 | 6/2003 | Neuman et al. | 424/93.21 |
| 2003/0124721 A1 | 7/2003 | Cheatham et al. | 435/366 |
| 2003/0138948 A1 | 7/2003 | Fisk et al. | 435/366 |
| 2003/0138950 A1 | 7/2003 | McAlister et al. | |
| 2003/0138951 A1 | 7/2003 | Yin | 435/370 |
| 2003/0148513 A1 | 8/2003 | Sugaya et al. | 435/368 |
| 2003/0158089 A1 | 8/2003 | Gallop et al. | |
| 2003/0161818 A1 | 8/2003 | Weiss et al. | 424/93.21 |
| 2003/0162290 A1 | 8/2003 | Inoue et al. | 435/366 |
| 2003/0170215 A1 | 9/2003 | Tsang et al. | 424/93.21 |
| 2003/0175963 A1 | 9/2003 | Rosenberg | 435/375 |
| 2003/0180269 A1 | 9/2003 | Hariri | 424/93.21 |
| 2003/0186439 A1 | 10/2003 | Nakauchi et al. | 435/370 |

(56) References Cited

U.S. PATENT DOCUMENTS

| | | |
|---|---|---|
| 2003/0199447 A1 | 10/2003 | Goldman et al. .............. 514/12 |
| 2003/0203483 A1 | 10/2003 | Seshi ........................... 435/366 |
| 2003/0203484 A1 | 10/2003 | Black et al. .................. 435/368 |
| 2003/0207450 A1 | 11/2003 | Young et al. ................. 435/368 |
| 2003/0211087 A1 | 11/2003 | Goldman ................... 424/93.21 |
| 2003/0211603 A1 | 11/2003 | Earp et al. ................... 435/366 |
| 2003/0211605 A1 | 11/2003 | Lee et al. ..................... 435/368 |
| 2003/0212024 A1 | 11/2003 | Keating et al. ................ 514/44 |
| 2003/0219894 A1 | 11/2003 | Seino et al. .................. 435/370 |
| 2003/0228295 A1 | 12/2003 | Svendsen .................. 424/93.21 |
| 2003/0235563 A1 | 12/2003 | Strom et al. ............... 424/93.21 |
| 2003/0235909 A1 | 12/2003 | Hariri et al. .................. 435/372 |
| 2004/0005704 A1 | 1/2004 | Csete et al. ................... 435/368 |
| 2004/0009566 A1 | 1/2004 | Okano et al. |
| 2004/0009593 A1 | 1/2004 | Keirstead et al. ............ 435/368 |
| 2004/0014206 A1 | 1/2004 | Robl et al. .................... 435/325 |
| 2004/0014210 A1 | 1/2004 | Jessell et al. ................. 435/368 |
| 2004/0014211 A1 | 1/2004 | Ogle et al. .................... 435/368 |
| 2004/0014662 A1 | 1/2004 | Lindquist et al. .............. 514/12 |
| 2004/0028657 A1 | 2/2004 | Okano et al. |
| 2004/0028660 A1 | 2/2004 | Hariri et al. |
| 2004/0029269 A1 | 2/2004 | Goldman et al. ............. 435/368 |
| 2004/0033597 A1 | 2/2004 | Toma et al. ................... 435/368 |
| 2004/0037818 A1 | 2/2004 | Brand et al. ............... 424/93.21 |
| 2004/0048372 A1 | 3/2004 | Hariri ........................... 435/366 |
| 2004/0058412 A1 | 3/2004 | Ho et al. ....................... 435/69.1 |
| 2004/0063202 A1 | 4/2004 | Petersen et al. .............. 435/368 |
| 2004/0072344 A1 | 4/2004 | Inoue et al. ................... 435/366 |
| 2004/0136967 A1 | 7/2004 | Weiss et al. |
| 2004/0204387 A1 | 10/2004 | McLaurin |
| 2004/0224401 A1 | 11/2004 | Ludwig et al. |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0148074 A1 | 7/2005 | Davies et al. |
| 2005/0249731 A1* | 11/2005 | Aslan et al. ................. 424/144.1 |
| 2006/0094113 A1 | 5/2006 | Epstein et al. |
| 2006/0128014 A1 | 6/2006 | Haggblad et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm et al. |
| 2007/0218549 A1 | 9/2007 | Mansbridge |
| 2007/0264269 A1 | 11/2007 | Harmon et al. |
| 2007/0264713 A1 | 11/2007 | Terstegge et al. |
| 2007/0275362 A1 | 11/2007 | Edinger et al. |
| 2008/0038782 A1 | 2/2008 | Borns |
| 2008/0112939 A1 | 5/2008 | Colter et al. |
| 2008/0145934 A1 | 6/2008 | Harris et al. |
| 2008/0159994 A1 | 7/2008 | Mantalaris et al. |
| 2008/0166328 A1 | 7/2008 | Harmon et al. |
| 2008/0226595 A1 | 9/2008 | Edinger et al. |
| 2009/0186358 A1 | 7/2009 | Melville et al. |
| 2010/0215714 A1 | 6/2010 | Messina et al. |
| 2010/0210013 A1 | 8/2010 | Mistry et al. |
| 2010/0260843 A1 | 10/2010 | Messina et al. |
| 2010/0272803 A1 | 10/2010 | Mistry et al. |
| 2012/0315251 A1 | 12/2012 | Harris et al. |
| 2013/0022585 A1 | 1/2013 | Messina et al. |
| 2014/0045263 A1 | 2/2014 | Mistry et al. |
| 2014/0154226 A1 | 6/2014 | Messina et al. |
| 2015/0064781 A1 | 3/2015 | Mistry et al. |
| 2015/0374758 A1 | 12/2015 | Buensuceso et al. |

FOREIGN PATENT DOCUMENTS

| | | |
|---|---|---|
| EP | 1 302 535 | 4/2003 |
| EP | 1 312 669 | 5/2003 |
| EP | 1 316 322 | 6/2003 |
| EP | 1 405 649 | 4/2004 |
| JP | 2003-235549 | 8/2003 |
| JP | 2004-254682 | 9/2004 |
| WO | 90/11354 A1 | 10/1990 |
| WO | 92/03917 A1 | 3/1992 |
| WO | 93/04169 A1 | 3/1993 |
| WO | WO 94/25584 A1 | 11/1994 |
| WO | 95/17911 A1 | 7/1995 |
| WO | WO 95/23216 | 8/1995 |
| WO | WO 96/01316 A1 | 1/1996 |
| WO | WO 96/05309 A2 | 2/1996 |
| WO | WO 98/17791 A1 | 4/1998 |
| WO | WO 98/51317 | 11/1998 |
| WO | WO 99/03973 | 1/1999 |
| WO | WO 99/28444 | 6/1999 |
| WO | WO 00/09666 | 2/2000 |
| WO | WO 00/38762 | 7/2000 |
| WO | WO 00/46351 | 8/2000 |
| WO | WO 00/053795 A1 | 9/2000 |
| WO | 00/73421 A3 | 12/2000 |
| WO | WO 01/11011 A2 | 2/2001 |
| WO | WO 01/19379 A3 | 3/2001 |
| WO | WO 01/34775 A1 | 5/2001 |
| WO | WO 02/029971 A1 | 4/2002 |
| WO | WO 02/36751 | 5/2002 |
| WO | WO 02/46373 A1 | 6/2002 |
| WO | WO 02/059278 A2 | 8/2002 |
| WO | WO 02/061053 | 8/2002 |
| WO | WO 02/062969 A2 | 8/2002 |
| WO | WO 02/063962 A1 | 8/2002 |
| WO | WO 02/064748 A2 | 8/2002 |
| WO | WO 02/064755 A2 | 8/2002 |
| WO | WO 02/086107 A2 | 10/2002 |
| WO | WO 03/023020 A1 | 3/2003 |
| WO | WO 03/025149 A2 | 3/2003 |
| WO | WO 03/029443 A1 | 4/2003 |
| WO | WO 03/029445 A1 | 4/2003 |
| WO | 03/039489 A3 | 5/2003 |
| WO | WO 03/042405 A2 | 5/2003 |
| WO | WO 03/048336 A2 | 6/2003 |
| WO | WO 03/055992 A2 | 7/2003 |
| WO | WO 03/064601 A2 | 8/2003 |
| WO | WO 03/066832 A2 | 8/2003 |
| WO | WO 03/068937 A2 | 8/2003 |
| WO | WO 03/070922 A1 | 8/2003 |
| WO | WO 03/072728 A2 | 9/2003 |
| WO | WO 03/080822 A1 | 10/2003 |
| WO | WO 03/087333 A2 | 10/2003 |
| WO | WO 03/087392 A2 | 10/2003 |
| WO | WO 03/089619 A2 | 10/2003 |
| WO | 03/102151 A2 | 12/2003 |
| WO | WO 03/10038 A1 | 12/2003 |
| WO | WO 03/102134 A2 | 12/2003 |
| WO | WO 03/104442 A1 | 12/2003 |
| WO | WO 2004/011012 A2 | 2/2004 |
| WO | WO 2004/011621 A2 | 2/2004 |
| WO | WO 2004/016747 A2 | 2/2004 |
| WO | WO 2004/023100 A2 | 3/2004 |
| WO | WO 04/039248 A2 | 5/2004 |
| WO | 2004/072273 A1 | 8/2004 |
| WO | 2005/001076 A2 | 1/2005 |
| WO | 2005/001077 A2 | 1/2005 |
| WO | 2005/001078 A2 | 1/2005 |
| WO | 2005/001079 A2 | 1/2005 |
| WO | 2005/001080 A2 | 1/2005 |
| WO | 2005/003334 A2 | 1/2005 |

(56) References Cited

FOREIGN PATENT DOCUMENTS

| WO | WO 05/021738    | 3/2005  |
|----|-----------------|---------|
| WO | 2005/038012 A2  | 4/2005  |
| WO | WO 05/038012 A3 | 4/2005  |
| WO | 2005/042703 A2  | 5/2005  |
| WO | WO 05/038012 R  | 1/2006  |
| WO | WO 06/027229    | 3/2006  |
| WO | WO 06/036826    | 4/2006  |
| WO | 2006/071773 A2  | 7/2006  |
| WO | 2006/071777 A2  | 7/2006  |
| WO | 2006/071778 A2  | 7/2006  |
| WO | 2006/071794 A2  | 7/2006  |
| WO | 2006/071802 A2  | 7/2006  |
| WO | WO 06/083394    | 8/2006  |
| WO | WO 06/105152    | 10/2006 |
| WO | WO 07/073552    | 6/2007  |
| WO | WO 07/108003    | 9/2007  |
| WO | WO 08/045498    | 4/2008  |
| WO | WO 08/060541    | 5/2008  |

OTHER PUBLICATIONS

Salgado et al. Bone tissue engineering: state of the art and future trends. Macromol Biosci. vol. 4, No. 8, pp. 743-765, Aug. 2004.*
Eagle, H. The specific amino acid requirements of a mammalian cell (strain L) in tissue culture. J Biol Chem, vol. 214, No. 2, pp. 839-852, Jun. 1955.*
Doyle, J. Spiraling complexity, robustness, and fragility in biology, http://www.cds.caltech.edu/~doyle/CmplxNets/Bio1.pdf, available online Feb. 28, 2004.*
Unigene entry for Hs.522632, *Homo sapiens* TMP metallopeptidase inhibitor 1 (TIMP1), printed from http://www.ncbi.nlm.nih.gov/ UniGene on Oct. 12, 2006.*
Aston et al. 1986, Journal of Bone and Joint Surgery, 68B: 29-35.*
Sigma Catalog [online], 2008 [retrieved on Feb. 11, 2009]. Retrieved from the Internets URL: http://www.sigmaaldrich.com/catalog/ ProductDetail.do?N4=A5955|SIGMA&N5=Product%20No.|BRAND_ KEY&F=SPEC>, p. 1.*
Liddiard et al., 1980, Arch. Toxicol., 44: 107-112.*
Can, et al., 2007, Stem Cells, 25: 2886-2895.*
Haynesworth et al., 1992, Bone, 13: 69-80.*
Diao et al. 2008, J. Biomed. Mater. Res., 91A: 123-131.*
Deans et al., Experimental Hematology, 2000, 28:875-884.*
Lonza (Cambrex) human Mesenchymal Stem Cells, downloaded from http://www.lonza.com/products-services/bio-research/primary-and-stem-cells/adult-stem-cells-and-media/human-mesenchymal-stem-cells-media/hmsc-human-mesenchymal-stem-cells.aspx, downloaded on Jan. 31, 2014.*
Ciavarella et al., Stem Cells and Development, 2009, 18:1211-1220.*
Liddiard (Arch Toxicol, 1980, 44:107-112).*
Aboody, K.S., et al., "Neural stem cells display extensive tropism for pathology in adult brain: evidence from intracranial gliomase," *PNAS*, 2000, 97(23), 12846-12851.
Age-Related Eye Disease Study Research Group, "A randomized, placebo-controlled, clinical trial of high-dose supplementation with vitamins C and E, beta carotene, and zinc for age-related macular degeneration and vision loss," AREDS Report No. 8, *Arch. Ophthalmal*, 2001, 119, 1417-1436.
Allcock, H.R., et al., "Synthesis of poly[amino acid alkyl ester)phosphazenes][1-3]," *Macromolecule*, 1977, 10(4), 824-830.
Altman, G.H., et al., "Advanced bioreactor with controlled application of multidimensional strain for tissue engineering," *J. Biomech. Eng.*, 2002, 124, 742-749.
Altman, R.D., et al., "Radiographic assessment of progression in osteoarthritis," *Arthritis & Rheum.*, 1987, 30(11), 1214-1225.
Anseth, K.S., et al., "In situ forming degradable networks and their application in tissue engineering and drug delivery," *J. of Control Release*, 2002, 78, 199-209.

Avital, I., et al., "Isolation, characterization, and transplantation of bone marrow-derived hepatocyte stem cells," *Biochem. & Biophys. Res. Comm.*, 2001, 288, 156-164.
Azizi, S.A., et al., "Engraftment and migration of human bone marrow stromal cells implanted in the brains of albino rats—similarities to astrocyte grafts," *Proc. Natl. Acad. Sci. USA*, 1998, 95, 3908-3913.
Baker, K.A., et at., "Intrastriatal and intranigral grafting of hNT neurons in the 6-OHDA rat model of Parkinson's Disease," *Exper. Neurol.*, 2000, 162, 350-360.
Balis, F., et al., "Central nervous system pharmacology of antileukemic drugs," *Am. J. of Pediatric. Hematol. Oncol.*, 1989, 11(1), 74-86.
Balkema, G.W., et al., "Impaired visual thresholds in hypopigmented animals," *Visual Neuroscience*, 1991, 6, 577-585.
Barberi, T., et al., "Neural subtype specification of fertilization and nuclear transfer embryonic stem cells and application in parkinsonian mice," *Nature Biotechnology*, 2003, 21(10), 1200-1207.
Beck, R.W., et al., "A clinical comparison of visual field testing with a new automated perimeter, the Humphrey field analyzer, and the Goldmann perimeter," *Ophthalmology*, 1985, 92(1), 77-82.
Björklund, L.M., et al., "Embryonic stem cells develop into functional dopaminergic neurons after transplantation in a Parkinson rat model," *PNAS*, 2002, 99(4), 2344-2349.
Bouteiller, P.L., et al., "Soluble HLA-G1 at the matemo-foetal interface—a review," *Placenta*, 2003, 24 (Suppl. A), S10-S15.
Brodsky, S.V., et al., "Coagulation, fibrinolysis and angiogenesis: new insights from knockout mice," *Exp. Nephrol.*, 2002, 10, 299-306.
Brooks, P., "Inflammation as an important feature of osteoarthritis," *Bull. World Health Org.*, 2003, 81(9), 689-690.
Brown, J.A., et at, "Blockade of programmed death-1 ligands on dendritic cells enhances T cell activation and cytokine production," *The J. of Immunology*, 2003, 170, 1257-1266.
Burnstein, R.M., et al., "Differentiation and migration of long term expanded human neural progenitors in a partial lesion model of Parkinson's disease," *Intern. J. of Biochem. & Cell Biology*, 2004, 36, 702-713.
Caballero, S., et al., "The many possible roles of stem cells in age-related macular degeneration," *Graefe's Arch Clin. Exp. Ophthalmol*, 2004, 242, 85-90.
Campbell, I.K., et al., "Human articular cartilage and chondrocytes produce hemopoietic colony-stimulating factors in culture in response to IL-1[1]," *J. of Immun.*, 1991, 147, 1238-1246.
Cao, Q., et al., "Stem cell repair of central nervous system injury," *J. of Neuroscience Res.*, 2002, 68, 501-510.
Caplan, A.I., et al., "Mesenchymal stem cells: building blocks for molecular medicine in the 21st century," *Trends in Molecular Med.*, 2001, 7(6), 259-264.
Chargracui, J., et al., "Fetal liver stroma consists of cells in epithelial-to-mesenchymal transition," *Blood*, 2003, 101, 2973-2982.
Chen, D., et al., "Differential roles for bone morphogenic protein (BMP) receptor type IB and IA in differentiation and specification of mesenchymal precursor cells to osteoblast and adipocyte lineages," *J. Cell Biol.*, 1998, 142(1), 295-305.
Cheng, A., et al., "Nitric oxide acts in a positive feedback loop with BDNF to regulate neural progenitor cell proliferation and differentiation in the mammalian brain," *Dev. Biol.*, 2003, 258, 319-333.
Coumans, B., et al., "Lymphoid cell apoptosis induced by trophoblastic cells: a model of active foeto-placental tolerance," *J. of Immunological Methods*, 1999, 224, 185-196.
D'Cruz, P.M., et al., "Mutation of the receptor tyrosine kinase gene Mertk in the retinal dystrophic Rcs rat," *Hum. Mol. Genet.*, 2000, 9(4), 645-651.
Danon, D., et al., "Macrophage treatment of pressure sores in paraplegia," *J. of Wound Care*, 1998, 7(6), 281-283.
Danon, D., et al., "Treatment of human ulcers by application of macrophages prepared from a blood unit," *Exp. Gerontol.*, 1997, 32(6), 633-641.
Dimri, G.P., et al., "A biomarker that identifies senescent human cells in culture and in aging skin in vivo," *Proc. Natl. Acad. Sci. USA*, 1995, 92, 9363-9367.

(56) References Cited

OTHER PUBLICATIONS

Domb, A., et al., "Degradable polymers for site-specific drug delivery," *Polymers for Advanced Technologies*, 1992, 3, 279-292.
Doshi, S.N., et al., "Evolving role of tissue factor and its pathway inhibitor," *Critical Care Med.*, 2002, 30(5), S241-5250.
Du, Y., et al., "Functional reconstruction of rabbit conical epithelium by human limbal cells cultured on amniotic membrane," *Molecular Vision*, 2003, 9, 635-643.
Edlund, H., "Pancreatic organogenesis—developmental mechanisms and implications for therapy," *Nat. Rev. Genet.*, 2002, 3, 524-532.
Efrat, S., et al., "Cell replacement therapy for type 1 diabetes," *Trends in Molecular Medicine*, 2002, 8(7), 334-339.
Ehtesham, M., et al., "Induction of glioblastoma apoptosis using neural stem cell-mediated delivery of tumor necrosis factor-related apoptosis-inducing ligand," *Cancer Res.*, 2002, 62, 7170-7174.
Ehtesham, M., et al., "The use of interleukin 12-secretingneural stem cells for the treatment of intracranial glioma," *Cancer Res.*, 2002, 5657-5663.
Ende, N., et al., "Parkinson's disease mice and human umbilical cord blood," *J. Med.*, 2002, 33(1-4), 173-180, 1 page (Abstract).
Engstad, C.S., et al., "The effect of soluble β-1,3-glucan and lipopolysaccharide on cytokine production and coagulation activation in whole blood," *Int. Immunopharmacol.*, 2002, 2, 1585-1597.
Enzmann, V., et al., "Enhanced induction of RPE lineage markers in pluripotent neural stem cells engrafted into the adult rat subretinal space," *Investig. Ophthalmol. Visual Sci.*, 2003, 44, 5417-5422.
Fazeabas, A.T., et al., "Endometrial function: cell specific changes in the uterine environment," *Mol. & Cellular. Endo.*, 2002, 186, 143-147.
Fiegel, H.C., et al., "Liver-specific gene expression in cultured human hematopoietic stem cells," *Stem Cells*, 2003, 21, 98-104.
Fischer, D., et al., "Lens-injury-stimulated axonal regeneration throughout the optic pathway of adult rats," *Exp. Neural*, 2001, 172, 257-272.
Freed, C.R., et al., "Transplantation of embryonic dopamine neurons for severe Parkinson's disease," *N. Engl. J. Med.*, 2001, 344(10), 710-719.
Frenkel, O., et al., "Activated macrophages for treating skin ulceration: gene expression in human monocytes after hypo-osmotic shock," *Clin. Exp. Immunol.*, 2002, 128, 59-66.
Friedman, J.A., et al., "Biodegradable polymer grafts for surgical repair of the injured spinal cord," *Neurosurgery*, 2002, 51(3), 742-751.
Fukuda, K., et al., "Reprogramming of bone marrow mesenchymal stem cells into cardiomyocytes," *C.R. Biol.*, 2002, 325, 1027-1038.
Gerdes, D., et al., "Cloning and tissue expression of two putative steroid membrane receptors," *Biol. Chem.*, 1998, 379, 907-911.
Gellersen, B., et al., "Cyclic AMP and progesterone receptor crosstalk in human endometrium: a decidualizing affair " *J. of Endocrinol.*, 2003, 178, 357-372.
Gökhan, Ş et al., "Basic and clinical neuroscience applications of embryonic stem cells," *Anat. Rec. (New Anat)*, 2001, 265, 142-156.
Gosiewska, A., et al., "Development of a three-dimensional transmigration assay for testing cell-polymer interactions for tissue engineering applications," *Tissue Eng.*, 2001, 7(3), 267-277.
Gottleib, D.I., "Large-scale sources of neural stem cells," *Ann. Rev. Neurosci.*, 2002, 25, 381-407.
Halvorsen, Y.D., et al., "Extracellular matrix mineralization and osteoblast gene expression by human adipose tissue-derived stromal cells," *Tissue Eng.*, 2001, 7, 729-741.
Hanahan, D., "Heritable formation of pancreatic β-cell tumours in transgenic mice expressing recombinant insulin/simian virus 40 oncogenes," *Nature*, 1985, 315, 115-122.
Haruta, M., et al., "In vitro and in vivo characterization of pigment epithelial cells differentiated from primate embryonic stem cells," *Investig. Ophthalmol. & Visual Sci.*, 2004, 45(3), 1020-1025.
Hayflick, L., "The longevity of cultured human cells," *J. Am. Geriatr. Soc.*, 1974, 22(1), 1-12.

Hayflick, L., "The strategy of senescence," *Gerontologist*, 1974, 14(1), 37-45.
Hongpaisan, J., "Inhibition of proliferation of contaminating fibroblasts by D-valine in cultures of smooth muscle cells from human myometrium," *Cell Biol. Int.*, 2000, 24,1-7.
Hu, A., et al., "Hepatic differentiation from embryonic stem cells in vitro," *Chin. Med. J.*, 2003, 116(12), 1893-1897.
Hughes, G.C., et al., "Therapeutic angiogenesis in chronically ischemic porcine myocardium: comparative effects of bFGF and VEGF," *Ann. Thorac. Surg.*, 2004, 77, 812-818.
Hutmacher, D.W., "Scaffold design and fabrication technologies for engineering tissues—state of the art and future perspectives," *J. Biomater. Sci. Polymer Edn.*, 2001, 12(1), 107-124.
Isacson, O., et al., "Specific axon guidance factors persist in the adult brain as demonstrated by pig neuroblasts transplanted to the rat," *Neurosci.*, 1996, 75(3), 827-837.
Isacson, O., "The production and use of cells as therapeutic agents in neurodegenerative diseases," *The Lancet (Neurology)*, 2003, 2, 417-424.
Ito, Y., et al., "A quantitative assay using basement membrane extracts to study tumor angiogenesis in vivo," *Int. J. Cancer*, 1996, 67, 148-152.
Jackson, J.A., et al., "Regeneration of ischemic cardiac muscle and vascular endothelium by adult stem cells,"*J. Clin. Invest.*, 2001, 107, 1395-1402.
Janderova, L., et al., "Human mesenchymal stem cells as an in vitro model for human adipogenesis," *Obes. Res.*, 2003, 11(1), 65-74.
Jang, Y.K., et al., "Retinoic acid-mediated induction of neurons and glial cells from human umbilical cord-derived hematopoietic stem cells," *J. of Neurosci. Res.*, 2004, 75, 573-584.
Johe, K.K., et al., "Single factors direct the differentiation of stem cells from the fetal and adult central nervous system," *Genes & Devel.*, 1996, 10, 3129-3140.
Johnstone, B., et al., "In vitro chondrogenesis of bone-marrow-derived mesenchymal stem cells," *Exp. Cell Res.*, 1998, 238, 265-272.
Jones-Villeneuve, E.M., et al., "retinoic acid-induced neural differentiation of embryonal carcinoma cells," *Mol. & Cellu. Biol.*, 1983, 3(12), 2271-2279.
Kadiyala, S., et al., "Culture expanded canine mesenchymal stem cells possess osteochondrogenic potential in vivo and in vitro," *Cell Transplant*, 1997, 6(2), 125-134.
Kicic, A., et al., "Differentiation of marrow stromal cells into photoreceptors in the rat eye," *J. of Neurosci.*, 2003, 23(21), 7742-7749.
Kim, S.K., et al., "Intercellular signals regulating pancreas development and function," *Genes Dev.*, 2001, 15, 111-127.
Kim, J.-H., et al., "Dopamine neurons derived from embryonic stem cells function in an animal model of Parkinson's disease," *Nature*, 2002, 418, 50-56.
Kim, J.Y., et al., "Ocular surface reconstruction: limbal stem cell transplantation," *Ophthal. Clin. N Am.*, 2003, 16, 67-77.
Lang, K.J.D., et al., "Differentiation of embryonic stem cells to a neural fate: a route to re-building the nervous system," *J. of Neurosci. Res.*, 2004, 76, 184-192.
Le Belle, J.E., et al., "Stem cells for neurodegenerative disorders: where can we go from here?,"*BioDrugs*, 2002, 16, 389-401.
Li, A., et al., "IL-8 directly enhanced endothelial cell survival, proliferation, and matrix metalloproteinases production and regulated angiogenisis," *J. Immunol.*, 2003, 170(6), 3369-3376.
Li, L.X., et al., "Inherited retinal dystrophy in the RCS rat: prevention of photoreceptor degeneration by pigment epithelial cell transplantation," *Exp. Eye Res.*, 1988, 47, 911-917.
Li, Y., et al., "Intracerebral transplantation of bone marrow stromal cells in a 1-methyl-4-phenyl-1,2,3,6-tetrahydropyridine mouse model of Parkinson's disease," *Neuroscience Letts.*, 2001, 315, 67-70.
Li, Y., et al., "Transplanted olfactory ensheathing cells promote regeneration of cut adult rat optic nerve axons," *J. of Neuro.*, 2003, 23(21), 7783-7788.
Liu, Y.-J., et al., "Molecular and genetic mechanisms of obesity: implications for future management," *Curr. Mol. Med.*, 2003, 3, 325-340.

(56) References Cited

OTHER PUBLICATIONS

Lockhart, et al., "Expression monitoring by hybridization to high-density oligonucleotide arrays," *Nat. Biotechnol.*, 1996, 14(13), 1675-1680.

Lund, R.D., et al., "Subretinal transplantation of genetically modified human cell lines attenuates loss of visual function in dystrophic rats," *Proc. Natl. Acad. Sci. USA*, 2001, 98(17), 9942-9947.

Lund, R.D., et al., "Cell transplantation as a treatment for retinal disease," *Progress in Retinal and Eye Research*, 2001, 20(4), 415-449.

Lund, R.L., et al., "Retinal transplantation: progress and problems in clinical application," *J. Leukocyte Biol.*, 2003, 74, 151-160.

Marx, W.F., et al., "Endovascular treatment of experimental aneurysms by use of biologically modified embolic devices: coil-mediated intraaneurysamal delivery of fibroblast tissue allografts," *Am. J. Neuroradiol.*, 2001, 22, 323-333.

Mason, A.J., et al., "The hypogonadal mouse: reproductive functions restored by gene therapy," *Science*, 1986, 234, 1372-1378.

Mayer-Proschel, M., et al., "Isolation of lineage-restricted neuronal precursors from multipotent neuroepithelial stem cells," *Neuron.*, 1997, 19, 773-785.

McDonald, J.A., et al., "Diminished responsiveness of male homosexual chronic hepatitis B virus carriers with HTLV-III antibodies to recombinant α-interferon," *Hepatology*, 1987, 7(4), 719-723.

Messina, D.J., et al., "Comparison of pure and mixed populations of human fetal-derived neural progenitors transplanted into intact and adult rat brain," *Exper. Neurol.*, 2003, 184, 816-829.

Mitchell, et al., "Matrix cells from Wharton's jelly form neurons and glia," *Stem Cells*, 2003, 21, 50-60.

Moll, S., et al., "Monitoring warfarin therapy in patients with lupus anticoagulants," *Ann. Intern. Med.*, 1997, 127(3), 177-185.

Mombaerts, et al., "Creation of a large genomic deletion at the T-cell antigen receptor β-subunit locus in mouse embryonic stem cells by gene targeting," *Proc. Nat. Acad. Sci. USA*, 1991, 88, 3084-3087.

Nakamura, T., et al., "Ocular surface reconstruction using cultivated mucosal epithelial stem cells," *Cornea*, 2003, 22(Supp. 1), S75-S80.

Nicosia, R.F., et al., "Modulation of microvascular growth and morphogenesis by reconstituted basement membrane gel in three-dimensional cultures of rat aorta: a comparative study of angiogenesis in matrigal, collagen, fibrin, and plasma clot," in *Vitro Cell Dev. Biol.*, 1990, 26, 119-128.

Nishida K., et al., "Functional bioengineered corneal epithelial sheet grafts from corneal stem cells expanded ex vivo on a temperature-responsive cell culture surface," *Transplantation*, 2004, 77(3), 379-385.

Nixon, P.J., et al., "The contribution of cone responses to rat electroretinograms," *Clin. Experiment Ophthalmol.*, 2001, 29(3), 193-196.

Nusinowitz, S., et al., "Rod multifocal electroretinograms in mice," *Invest Ophthalmol Vis. Sci.*, 1999, 40(12), 2848-2858.

Oh, S.-H., et al., "Hepatocyte growth factor induces differentiation of adult rat bone marrow cells into a hepatocyte lineage in vitro," *Biochem. & Biophys. Res. Comm.*, 2000, 279, 500-504.

Okumoto, K., et al., "Differentiation of bone marrow cells into cells that express liver-specific genes in vitro: implication of the notch signals in differentiation," *Biochem. & Biophys. Res. Commun.*, 2003, 304, 691-695.

Orlic, D., et al., "Stem cells for myocardial regeneration," *Circ. Res.*, 2002, 91, 1092-1102.

Ornitz, D.M., et al., "Elastase I promoter directs expression of human growth hormone and SV40 T antigen genes to pancreatic acinar cells in transgenic mice," *Cold Spring Harbor Symp.Quant. Biol.*, 1985, vol. L, 399-409.

Osborne, N.N., et al., "Some current ideas on the pathogenesis and the role of neuroprotection in glaucomatous optic neuropathy," *Eur. J. Ophthalmol.*, 2003, 13(Supp. 3), S19-S26.

Rabbany, S.Y., et al., "Molecular pathways regulating mobilization of marrow-derived stem cells for tissue revascularization," *Trends in Molecular Med.*, 2003, 9(3), 109-117.

Rafii, S., et al., "Therapeutic stem and progenitor cell transplantation for organ vascularization and regeneration," *Nature Med.*, 2003, 9(6), 702-712.

Raman-Cueto, A., et al., "Functional recovery of paraplegic rats and motor axon regeneration in their spinal cords by olfactory ensheathing glia," *Neuron*, 2000, 25, 425-435.

Readhead, C., et al., "Expression of a myelin basic protein gene in transgenic shiverer mice: correction of the dysmyelinating phenotype," *Cell*, 1987, 48, 703-712.

Refaie, A., et al., "Experimental islet cell transplantation in rats: optimization of the transplantation site," *Trans. Proc.*, 1998, 30, 400-403.

Reubinoff, B.E., et al., "Neural progenitors from human embryonic stem cells," *Nature Biotechnology*, 2001, 19, 1134-1140.

Rickard, D.J., et al., "Induction of rapid osteoblast differentiation in rat bone marrow stromal cell cultures by dexamethasone and BMP-2," *Dev. Biol.*, 1994, 161, 218-228.

Romanov, Y.A., et al., "Searching for alternative sources of postnatal human mesenchymal stem cells," *Stem Cells*, 2003, 21, 105-110.

Rosen, E.M., et al., "HGF/SF in angiogenesis," *Ciba Found. Symp.*, 1997, 212, 215-229.

Rutherford, A., et al., "Eyeing-up stem cell transplantation," *Trends in Molecular Medicine*, 2003, 7(1), p. 11.

Sahn, D.J., et al., "Recommendations regarding quantitation in M-Mode echocardiography: results of a survey of echocardiographic measurements," *Circulation*, 1978, 58, 1072-1083.

Sakariassen, K.S., et al., "Methods and models to evaluate shear-dependent and surface reactivity-dependent antithrombotic efficacy," *Thromb. Res.*, 2001, 104, 149-174.

Salcedo, et al., "Human endothelial cells express CCR2 and respond to MCP-1: direct role of MCP-1 in angiogenesis and tumor progression," *Blood*, 2000, 96(1), 34-40.

Sauve, Y., et al., "The relationship between full field electroretinogram and perimetry-like visual thresholds in RCS rats during photoreceptor degeneration and rescue by cell transplants," *Vision Res.*, 2004, 44(1), 9-18.

Schraermeyer, U., et al., "Subretinally transplanted embryonic stem cells rescue photoreceptor cells from degeneration in the RCS rats," *Cell Transplantation*, 2001, 10, 673-680.

Schwartz, R.E., et al., "Multipotent adult progenitor cells from bone marrow differentiate into functional hepatocyte-like cells," *J. of Clin. Invest.*, 2002, 109(10), 1291-1302.

Sebire, G., et al., "*In vitro* production of IL-6,IL-1 β, and tumor necrosis factor-alpha by human embryonic microglial and neural cells," *J. Immunol.*, 1993, 150, 1517-1523.

Shani, M., "Tissue-specific expression of rat myosin light-chain 2 gene in transgenic mice," *Nature*, 1985, 314, 283-286.

Shimizu, T., et al., "Cell sheet engineering for myocardial tissue reconstruction," *Biomaterials*, 2003, 24, 2309-2316.

Siminoff, R., et al., "Properties of reptilian cutaneous mechanoreceptors," *Exp. Neurol.*, 1968, 20(3), 403-414.

Sordillo, L.M., et al., "Culture of bovine mammary epithelial cells in D-valine modified medium: selective removal of contaminating fibroblasts," *Cell Biol. Int. Rep.*, 1988, 12, 355-364.

Storch, T.G., "Oxygen concentration regulates 5-azacytidine-induced myogenesis in $C_3H/10T1/2$ cultures," *Biochim. Biophys. Acta*, 1990, 1055, 126-129.

Street, C.N., et al., "Stem cells: a promising source of pancreatic islets for transplantation in type 1 diabetes," *Curr. Top Dev. Biol.*, 2003, 58, 111-136.

Svendsen, C.N., et al., "Long-term survival of human central nervous system progenitor cells transplanted into a rat model of Parkinson's disease," *Experim. Neurol.*, 1997, 148, 135-146.

Svendsen, C.N., "The amazing astrocyte," *Nature*, 2002, 417, 29-32.

Swift, G.H., et al., "Tissue-specific expression of the rat pancreatic elastase I gene in transgenic mice," *Cell*, 1984, 38, 639-646.

Tomita, M., et al., "Bone marrow-derived stem cells can differentiate into retinal cells in injured rat retina," *Stem Cells*, 2002, 20, 279-283.

Tresco, P.A., et al., "Cellular transplants as sources for therapeutic agents," *Advanced Drug Delivery Reviews*, 2000, 42, 3-27.

(56) References Cited

OTHER PUBLICATIONS

Tsonis, P.A., et al., "Lens and retina regeneration: transdifferentiation, stem cells and clinical applications," *Experim. Eye Res.*, 2004, 78, 161-172.
Turner, J.F., "Inherited retinal dystrophy in the RCS rat: prevention of photoreceptor degeneration by pigment epithelial cell transplantation," *Exp. Eye Res.*, 1988, 47, 911-917.
Tusher, V.G., et al., "Significance analysis of microarrays applied to the ionizing radiation response," *Proc. Natl. Acad. Sci. USA*, 2001, 98(9), 5116-5121.
Van Hoffelen, S.J., et al., "Incorporation of murine brain progenitor cells into the developing mammalian retina," *Invest. Ophthalmol. Vis. Sci.*, 2003, 44, 426-434.
Vassliopoulos, G., et al., "Transplanted bone marrow regenerates liver by cell fusion," *Nature*, 2003, 422, 901-904.
Villegas-Perez, M.P., et al., "Influences of peripheral nerve grafts on the survival and regrowth of axotomized retinal ganglion cells in adult rats," *J. of Neurosci.*, 1988, 8(1), 265-280.
Von Koskull, H., et al., "Induction of cytokeratin expression in human mesenchymal cells," *J. Cell Physiol.*, 1987, 133, 321-329.
Walboomers, X.F., et al., "Cell and tissue behavior on microgrooved surfaces," *Odontology*, 2001, 89, 2-11.
Wang, D., et al., "Synthesis and characterization of a novel degradable phosphate-containing hydrogel," *Biomaterials*, 2003, 24, 3969-3980.
Wang, X., et al., "Cell fusion is the principal source of bone-marrow-derived hepatocytes," *Nature*, 2003, 422, 897-900.
Wegman, A., et al., "Nonsteroidal anti-inflammatory drugs or acetaminophen for osteoarthritis of the hip or knee? A synstematic review of evidence and guidelines," *J. Rheumatol.*, 2004, 31, 344-354.
Weiss, M.L., et al., "Transplantation of porcine umbilical cord matrix cells into the rat brain," *Exp. Neur.*, 2003, 182, 288-299.
Wobus, A.M., et al., "Retinoic acid accelerates embryonic stem cell-derived cardiac differentiation and enhances development of ventricular cardiomyocytes," *J. Mol. Cell Cardiol.*, 1997, 29, 1525-1539.
Woodbury, D., et al., "Adult rat and human bone marrow stromal cells differentiate into neurons," *J. of Neurosci. Res.*, 2000, 61, 364-370.
Xu, C., et al., "Characterization and enrichment of cardiomyocytes derived from human embryonic stem cells," *Circ. Res.*, 2002, 91, 501-508.
Yang, H., et al., "Region-specific differentiation of neural tube-derived neuronal restricted progenitor cells after heterotopic transplantation," *PNAS*, 2000, 97(24), 13366-13371.
Yip, H.K., et al., "Axonal regeneration of retinal ganglion cells: effect of trophic factors," *Prog. Retin Eye Res.*, 2000, 19(5), 559-575.
Yu, M., et al., "Mid-trimester fetal blood-derived adherent cells share characteristics similar to mesenchymal stem cells but full-term umbilical cord blood does not," *British J. of Haematology*, 2004, 124, 666-675.
Zangani, D., et al., "Multiple differentiation pathways of rat mammary stromal cells in vitro: acquisition of a fibroblast, adipocyte or endothelial phenotype is dependent on hormonal and extracellular matrix stimulation," *Differentiation*, 1999, 64, 91-101.
Zeng, B.Y., et al., "Regenerative and other responses to injury in the retinal stump of the optic nerve in adult albino rats: transaction of the intracranial optic nerve," *J. Anat.*, 1995, 186, 495-508.
Zhang, S.-C., et al., "In vitro differentiation of transplantable neural precursors from human embryonic stem cells," *Nature Biotechnology*, 2001, 19, 1129-1133.
Eblenkamp, M. et al., "Umbilical cord stromal cells (UCSC). Cells featuring osteogenic differentiation potential," *Der Orthopade*, Dec. 2004, 33(12), 1338-1345.
Fukuchi, Y. et al., "Human Placenta-Derived Cells Have Mesenchymal Stem/Progenitor Cell Potential," *Stem Cells*, Alphamed Press, Dayton Ohio, 2004, 22(5), 649-658.

Wulf, G. G. et al., "Mesengenic Progenitor Cells Derived From Human Placenta," *Tissue Engineering*, Larchmont, NY, Jul. 2004, 10(7/8), 1136-1147.
U.S. Appl. No. 11/617,346, filed Dec. 28, 2006, Kihm.
Abbas, A.K., Lichtman, A.H., *Cellular and Molecular Immunology*, 5th Ed. (2003) Saunders, Philadelphia, p. 171.
Auda-Boucher, G., et al., "Staging of the commitment of murine cardiac cell progenitors," *Dev. Bio.*, 2000, 225(1), 214-225 (Abstract 2 pages).
Bao, Z.Z.., et al., "Regulation of chamber-specific gene expression in the developing heart by Irx4," *Science*, 1999, 283(5405), 1161-1164 (Abstract 1 page).
Constantini, S., et al., "The effects of methylprednisolone and the ganglioside GM1 on acute spinal cord injury in rats," *J. Neurosurg.*, 1994, 80(1), 97-111 (Abstract 2 pages.
Dawson, T.M., et al., "Neuroprotective and neurorestorative strategies for Parkinson's disease," *Nat. Neurosci.*, 2002, 5 Suppl., 1058-1061 (Abstract 1 page).
Edelstein, M. L. et al., "Gene therapy clinical trials worldwide 1989-2004—an overview," *J. Gene Med.*, Jun. 2004, 6(6), 597-602.
Eisenhofer, G., E., et al., "Tyrosinase: a developmentally specific major determinant of peripheral dopamine," *FASEB J.*, 2003, 1248-1255.
Foley, A. et al., "Heart induction: embryology to cardiomyocyte regeneration," *Trends Cardiovasc Med.*, Apr. 2004, 14(3), 121-125.
Goodwin, H. S. et al., "Multilineage differentiation activity by cells isolated from umbilical cord blood: Expression of bone, fat and neural markers," *Biology of Blood and Marrow Transplantation*, 2001, 7, 581-588.
Hill, M. et al., "Treatment for swallowing difficulties (dysphagia) in chronic muscle disease," *Cochrane Database Syst Rev.*, 2004, (2):CD004303.
Holz, F. G. et al., "Intraocular microablation of choroidal tissue by a 308 nm AIDA excimer laser for RPE-transplantation in patients with age-related macular degeneration," *Biomed Tech (Berlin)*, Apr. 2003, 48(4), 82-85.
Ishii, M. et al., "Molecular markers distinguish bone marrow mesenchymal stem cells from fibroblasts," *Biochemical and Biophysical Research Communications*, Jun. 24, 2005, 332(1), 297-303.
Jaffe, E. A. et al., "Culture of human endothelial cells derived from umbilical veins," *J Clin Invest*, 1973, 52, 2745-2756.
Jikuhara, T. et al., "Left atrial function as a reliable predictor of exercise capacity in patients with recent myocardial infarction," *Chest*, Apr. 1997, 111(4), 922-928.
Joussen, A. M., "Cell transplantation in age related macular degeneration: current concepts and future hopes," *Graefe's Arch. Clin. Exp. Ophthalmol.*, 2004, 242, 1-2.
Klassen, H. et al., "Stem cells and retinal repair," *Prog. Retin. Eye Res.*, 2004, 23(2), 149-181 (Abstract 1 page).
Laface, D., et al., "Genetransfer into hematopoietic progenitor cells mediated by an adeno-associated virus vector," *Virology*, 1998, 162, 483-486.
Langeggen, H. et al., "HUVEC take up opsonized zymosan particles and secrete cytokines IL-6 and IL-8 in vitro," *FEMS Immunol. Med. Microbiol.*, 2003, 36, 55-61.
Le Bouteiller, P., et al., "Soluble HLA-G1 at the matemo-foetal interface—a review," *Placenta*, 2003, 24 (Suppl. A), S10-S15.
Lodie, T. A. et al., "Systematic Analysis of Reportedly Distinct Populations of Mulitpotent Bone Marrow-Derived Stem Cells Reveals a Lack of Distinction," *Tissue Engineering*, Oct. 2002, 8(5), 739-751.
Luo, D. et al., "Synthetic DNA delivery systems," *Nat. Biotechnol.*, Jan. 2000, 18(1), 33-36.
MacDonald, R.J., "Expression of the pancreatic elastase I gene in transgenic mice," *Hepatology*, 1987, 7(1), 42S-51S.
Medicetty, S. et al., "Transplantation of Human Umbilical Cord Matrix Stem Cells Alleviates Apomorphine-Induced Rotations in Parkinsonian Rats", 2003, XP-002383776, 1 page.
Medline Plus Online Medical Dictionary, definitions of "undifferentiated," and "differentiate," and "differentiation." Retrieved online Mar. 6, 2007. URL:www.nlm.nih.gov/medlineplus/mplusdictionary.html.

(56) References Cited

OTHER PUBLICATIONS

Merx, M. W. et al., "Transplantation of human umbilical vein endothelial cells improves left ventricular function in a rat model of myocardial infarction," *Basic Res. Cardiol.*, 2005, 100, 208-216.

Morgenstern, J. P., et al., "Advanced mammalian gene transfer: high titre retroviral vectors with multiple drug selection markers and a complementary helper-free packaging cell line," *Nucleic Acids Res.*, 1990, 18(12), 3587-3596.

Moulder, J. E., "Pharmacological intervention to prevent or ameliorate chronic radiation injuries," *Semin. Radiat. Oncol.*, 2003, 13, 73-84.

Nork, T. M. et al., "Swelling and Loss of Photoreceptors in Chronic and Experimental Glaucomas," *Arch. Ophthalmol.*, 2000, 118, 235-245.

Palu, G. et al., "In pursuit of new developments for gene therapy of human disease," *J. Biotechnol.*, Feb. 1999, 68(1), 1-13.

Phipps, J. A. et al., "Paired-flash identification of rod and cone dysfunction in the diabetic rat," *Investigative●Ophthalmology & Visual Science*, 2004, 45(12), 4592-4600.

Pittenger, M. F. et al., "Multilineage potential of adult human mesenchymal stem cells," *Science*, 1999, 284, 143-147 and seven pages of online supplementary material.

Reyes, M., et al., "Purification and ex vivo expansionof postnatal human marrow mesodermal progenitor cells," *Blood*, 2001, 98(9), 2615-2625.

Rezai, KA., et al., "Iris pigment epithelium transplantation," *Graefes Arch. Clin. Ophthalmol.*, 1997, 235, 558-562.

Rios, M., et al., "Catecholamine Synthesis is Mediated by Tyrosinase in the Absence of Tyrosine Hydroxylase," *J. Neurosci.*, 1999, 3519-3526.

Sethe, S. et al., "Aging of mesenchymal stem cells," *Ageing Research Reviews*, 2006, 5, 91-116.

Taylor, D. A. et al., "Regenerating functional myocardium: Improved performance after skeletal myoblast transplantation," *Nature Medicine*, Aug. 1998, 4(8), 929-933. Erratum in Nature Medicine, 4(10), 1200.

Taylor, D. A. et al., "Cardiac chimerism as a mechanism for self-repair: does it happen and if so to what degree?" *Circulation*, Jul. 2002, 106(1), 2-4.

Timmermans et al., "Stem cells for the heart, are we there yet?" *Cardiology*, 2003, 100(4), 176-185.

Tremain, N. et al., "MicroSAGE Analysis of 2,353 Expressed Genes in a Single Cell-Derived Colony of Undifferentiated Human Mesénchymal Stem Cells Reveals mRNAs of Multiple Cell Lineages," *Stem Cells*, 2001, 19, 408-418.

Vajsar, J. et al., "Walker-Warburg syndrome," *Orphanet Journal of Rare Diseases*, 2006, 1, 29.

Verma, I. M. et al., "Gene therapy—promises, problems and prospects," *Nature*, Sep. 1997, 389(6648), 239-242.

Vermot-Desroches, C. et al., "Heterogeneity of antigen expression among human umbilical cord vascular endothelial cells: identification of cell subsets by co-expression of haemopoietic antigens," *Immunol. Lett.*, 1995, 48, 1-9.

Weiss, M. L. et al., "Human umbilical cord matrix stem cells: preliminary characterization and effect of transplantation in a rodent model of Parkinson's disease," *Stem Cells*, 2006, 24, 781-792.

Xu, Y., et al., "Dopamine, in the presence of tyrosinase, covalently modifies and inactivates tyrosine hydroxylase," *J. Neurosci. Res.*, 1998, 54(5), 691-697 (Abstract, 3 pages).

Ye, Q. et al., "Recovery of Placental-Derived Adherent Cells with Mesenchymal Stem Cell Characteristics", 2001, 98(11), 147B, XP-009026843.

Yokoo, T. et al., "Stem cell gene therapy for chronic renal failure," *Curr. Gene Ther.*, 2003, 3, 387-394.

Zimmermann, S. et al., "Lack of telomerase activity in human mesenchymal stem cells," *Leukemia*, 2003, 17, 1146-1149.

Zuloff-Shani, A. et al., "Macrophage suspensions prepared from a blood unit for treatment of refractory human ulcers," *Transfus Apheresis Sci.* 2004, 30(2), 163-167.

Agbulut, O. et al., "Comparison of Human Skeletal Myoblasts and Bone Marrow-Derived CD133+ Progenitors for the Repair of Infarcted Myocardium," *Journal of the American College of Cardiology*, 2004, 44(2), 458-463.

Aldskogius, H. et al., "Strategies for repair of the deafferented spinal cord," *Brain Res. Rev.*, 2002, 40, 301-308.

Bhindi, R. et al., "Rat models of myocardial infarction," *Thromb Haemost*, 2006, 96, 602-610.

Jomura, S., et al., "Potential Treatment of Cerebral Global Ischemia with Oct. 4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.

Lindvall, O. et al., "Stem cell therapy for human neurodegenerative disorders—how to make it work," *Nature Medicine*, Jul. 2004, S42-S50.

Pittenger, M. F. et al., "Mesenchymal Stem Cells and Their Potential as Cardiac Therapeutics," *Circ. Res.*, 2004, 95, 9-20.

Qian Ye et al., "Recovery of Placental-Derived Adherent Cells with Mesenchymal Stem Cell Characteristics", *Blood*, 2001, 98(11), 147B, Abstract 4260, XP-009026843.

Yang Chen et al., "Enhancement of neovascularization with cord blood $CD133^+$ cell-derived endothelial progenitor cell transplantation," *Thromb. Haemost.*, 2004, 91(6), 1202-1212.

Bergers G. et al., "The role of pericytes in blood-vessel formation and maintenance," Neuro-Oncology, 2005, 7, 452-464.

Blakemore, W. F. et al., "Modelling Large Areas of Demyelination in the Rat Reveals the Potential and Possible Limitations of Transplanted Glial Cells for Remyelination in the CNS," GLIA, 2002, 38, 155-168.

Franc, S. et al., "Microfibrillar composition of umbilical cord matrix: characterization of fibrillin, collagen VI and intact collagen V," Placenta, 1988, 19, 95-104.

Mackay et al., "Chondrogenic differentiation of cultured human mesenchymal stem cells from marrow," Tissue Engineering, 1998, 4(4), 415-428.

Schouten, J.W. et al., "A Review and Rationale for the Use of Cellular Transplantation as a Therapeutic Strategy for Traumatic Brain Injury," Journal of Neurotrauma, 2004, 21(11), 1501-1538.

Merriam-Webster Medline Plus Online Medical Dictionary, definitions of "iliac", "ilium" ileal/ileac and "ileum", [online] [retrieved on Feb. 13, 2008]. Retrieved from the Internet: URL://www.nlm.nih.gov/medlineplus/mplusdictionary.html.

Hoynowski, S. M. et al., Characterization and differentiation of equine umbilical cord-derived matrix cells. Biochemical and Biophysical Research Communications, Aug. 2007, 362, 347-353.

Aggarwal et al., "Human Mesenchymal Stem Cells Modulate Allogeneic Immune Cell Responses," *Blood*, 2005; 105(4): 1815-1822.

Bai, M., et al., "Dimerization of the Extracellular Calcium-sensing Receptor (CaR) on the Cell Surface of CaR-Transfected HEK293 Cells," *J. Biol Chem.*, 1998; 273(36): 23605-23610.

Bradley, B.A., "The Role of HLA Matching in Transplantation," *Immunol. Lett.*, 1991; 29:55-59.

Bussolati et al., "Isolation of Renal Progenitor Cells from Adult Human Kidney," *American Journal of Pathology*, 2005; 166(2):545-555.

Carter, D et al., "Characterization of MSC Potential to Treat GVHD Using Molecular Markers Linked to MSC-Mediated Immunosuppression in Vitro," *Blood*, 2005; 106(11) part 2, Abstract No. 4322, 160B.

"Cell Lysis, p. 2" http://www.piercenet.com/obiects/view.cfm?type=Page&ID=1904ED25-8FA4-475C-8068-C2EB13D5F4E7; assessed Aug. 7, 2008.

Chen, J. et al., "Therapeutic Benefit of Intravenous Administration of Bone Marrow Stromal Cells after Cerebral Ischemia in Rats," *Stroke*, 2001; 32(4):1005-11.

Del Monte, F. et al., "Improvement in Survival and Cardiac Metabolism After Gene Transfer of Sarcoplasmic Reticulum $Ca^{2+}$-ATPase in a Rat Model of Heart Failure," *Circulation*, 2001;104:1424-1429.

Dickinson, A.M. et al., "Non-HLA Immunogenetics in Hematopoietic Stem Cell Transplantation," *Curr. Opin. Immunol.*, 2005; 17(5):517-25.

(56) References Cited

OTHER PUBLICATIONS

Fernandes;A.M. et al., "Mouse Embryonic Stem Cell Expansion in a Microcarrier-based Stirred Culture System," *Journal of Biotechnology*, 2007; 132(2): 227-236.

Gröhn, P. et al., "Collagen-Coated $BA^{2+}$-Alginate Microcarriers for the Culture of Anchorage-Dependent Mammalian Cells," *BioTechniques*, 1997; 22(5): 970-975.

Gupta, S. et al., "Isolation and Characterization of Kidney-Derived Stem Cells," *J. of Am. Soci. of Nephrol.*, 2006; 17(11):3028-40.

Herrera, M.B. et al., "Mesenchymal Stem Cells Contribute to the Renal Repair of Acute Tubular Epithelial Injury," *Int. J. Mol. Med.*, 2004; 14(6):1035-41.

Hishikawa, K. et al., "Musculin/MyoR is Expressed in Kidney Side Population Cells and Can Regulate Their Function," *Journal of Cell Biology*, 2005; 169(6):921-28.

In'T Anker, P., et al., "Isolation of Mesenchymal Stem Cells of Fetal or Maternal Origin from Human Placenta," *Stem Cells*, 2004; 22:1338-45.

Jones, J. et al., "Insulin-Like Growth Factors and their Binding Proteins: Biological Actions," *Endocrine Review*, 1995; 16(1):3-34.

Kisiday, J et al., "Self-Assembling Peptide Hydrogel Fosters Chondrocyte Extracellular Matrix Production and Cell Division: Implications For Cartilage Tissue Repair," *PNAS*, 2002; 99(15):9996-10001.

Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-1648.

Li, C.D. et al., "Mesenchymal Stem Cells Derived From Human Placenta Suppress Allogeneic Umbilical Cord Blood Lymphocyte Proliferation," *Cell Research*, 2005; 15(7):539-47.

Li, Y. et al., "Intact, Injured, Necrotic and Apoptotic Cells after Focal Cerebral Ischemia in the Rat," *J. Neurol. Sci.*, 1998; 156(2): 119-32.

Li, Y. et al., "Ultrastructural and Light Microscopic Evidence of Apoptosis after Middle Cerebral Artery Occlusion in the Rat," *Am. J. Pathol.*, 1995; 146(5): 1045-51.

Lindenlaub, T. et al., "Partial Sciatic Nerve Transection as a Model of Neuropathic Pain: A Qualitative and Quantitative Study," *PAIN*, 2000; 89(1): 97-106.

Ma, L. et al., "Human Umbilical Cord Wharton's Jelly-Derived Mesenchymal Stem Cells Differentiation into Nerve-Like Cells," *Chinese Med. Jour.*, 2005; 118(23): 1987-93.

Maeshima, A. et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-98.

Melero-Martin, J. et al., "Optimal In-Vitro Expansion of Chondroprogenitor Cells in Monolayer Culture," *Biotechnology and Bioengineering*, 2006; 93(3):519-33.

Merriam-Webster Online Dictionary 10th Edition, Definition of "Scaffold" [retrieved on Sep. 12, 2008].

Moore, A.E et al., "Parkinsonian Motor Deficits are Reflected by Proportional A9/A10 Dopamine Neuron Degeneration in the Rat," *Exp. Neurol.*, 2001; 172(2):363-76.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-06.

Oliver, J.A et al., "The Renal Papilla is a Niche for Adult Kidney Stem Cells," *J. Clin Invest.*, 2004; 114(6):795-804.

Panepucci, R.A. et al., "Comparison of Gene Expression of Umbilical Cord Vein and Bone Marrow-Derived Mesenchymal Stem Cells," *Stem Cells*, 2004; 22(7): 1263-78.

Pera, M.F. et al., "Human Embryonic Stem Cells", *J. Cell Science*, 2000; 113:5-10.

Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-33.

Plaia, T., et al., "Characterization of a New Nih-Registered Variant Human Embryonic Stem Cell Line, BG01V: A Tool For Human Embryonic Stem Cell Research," *Stem Cells*, 2006: 24(3): 531-546.

Pountos, I. et al., "Mesenchymal Stem Cell Tissue Engineering: Techniques for Isolation, Expansion and Application," *Injury*, 2007; 38(Supp. 4):S23-33.

Quaini, F. et al., "Chimerism of the Transplanted Heart," *NEJM*, 2002; 346:5-15.

Russo, E., Cultivating Policy from Cell Types, *The Scientist*, 2001; 15(11):6.

Sagrinati, C. et al., "Isolation and Characterization of Multipotent Progenitor Cells from the Bowman's Capsule of Adult Human Kidney," *Journal of American Society of Nephrology*, 2006; 17(9)2443-56.

Schallert, T. et al., "Use-Dependent Structural Events in Recovery of Function," *Brain Plasticity, Adv. Neurol.*, 1997; 73:229-38.

Schreuder, G.M et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54(4):409-37.

Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-26.

Song, H. et al., "Astroglia Induce Neurogenesis From Adult Neural Stem Cells," *Nature*, 2002; 417(6884):39-44.

Tao, W., "Application of Encapsulated Cell Technology For Retinal Degenerative Disease", *Expert. Opin. Biol. Ther.*, 2006; 6(7): 717-726.

Toma, C. et al., "Human Mesenchymal Stem Cells Differentiate to a Cardiomyocyte Phenotype in the Adult Murine Heart," *Circulation*, 2002; 105:93-98.

Turner, D., "The Human Leucocyte Antigen (HLA) System," *Vox Sang.*, 2004; 87(Suppl 1):S87-S90.

Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.

Ulloa-Montoya, F. et al., "Culture Systems for Pluripotent Stem Cells," *Journal of Bioscience and Bioengineering*, 2005; 100(1):12-27.

Wenning, G.K et al., "Neural Transplantation in Animal Models of Multiple System Atrophy: A Review," *J. Nueral Transm.*, 1999; Suppl.(55):103-13.

Wikipedia, Definition of "Iliac crest" provided by Wikipedia, the free encyclopedia; retrieved from the Internet at URL: http://en.wikipedia.org/wiki/Iliac_crest; downloaded on Dec. 18, 2007.

Williams, J.T. et al., "Cells Isolated From Adult Human Skeletal Muscle Capable of Differentiating Into Multiple Mesodermal Phenotypes," *Am. Surg.* Jan. 1999:65(1):22-6.

Wolford, L.M. et al., "Considerations in Nerve Repair," *BUMC Proceedings*, 2003; 16:152-156.

Xu, A. et al.,"Soft, Porous Poly(D,L lactide-co-glycotide) Microcarriers Designed for Ex Vivo Studies and for Transplantation of Adherent Cell Types including Progenitors," *Annals of the New York Academy of Sciences*, 2001, vol. 944: 144-159.

Yamashima, T., "Implication of Cysteine Proteases Calpain, Cathepsin and Caspase in Ischemic Neuronal Death of Primates," *Progress in Neurobiology*, 2000; 62:273-295.

Zhang, L. et al., "A Test for Detecting Long-Term Sensorimotor Dysfunction in the Mouse after Focal Cerebral Ischemia," *J. Neurosci. Methods*, 2002; 117(2):207-14.

Zhang, X. et al., "Efficient Adeno-Associated Virus-Mediated Gene Expression in Human Placenta-Derived Mesenchymal Cells," *Microbiol. Immunol.*, 2003; 47(1):109-16.

Zhang, Y. et al., "Comparison of Mesenchymal Stem Cells from Human Placenta and Bone Marrow," *Chinese Medical Journal*, 2004; 117(6):882-87.

(56) References Cited

OTHER PUBLICATIONS

Zhang, Z.G. et al., "Correlation of VEGF and Angiopoietin Expression with D-ISRuption of Blood-Brain Barrier and Angiogenesis after Focal Cerebral Ischemia," *J. Cereb. Blood Flow Metab.*, 2002; 22(4):379-92.
Correspondence from Celgene Corporation dated Sep. 15, 2008, regarding U.S. Publication No. 2005/0058631 (U.S. Appl. No. 11/315,969) and U.S. Publication No. 2006/0154366 (U.S. Appl. No. 11/315,969).
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the United States Patent and Trademark Office, Final Office Action in re: U.S. Appl. No. 11/315,898, dated Sep. 16, 2008, 13 pages.
In the United States Patent and Trademark Office, Non-Final Office Action in re: U.S. Appl. No. 11/322,372, dated Sep. 3, 2008, 45 pages.
In the United States Patent and Trademark Office, Non-Final Office Action, in re: U.S. Appl. No. 11/297,156, dated Oct. 10, 2008, 16 pages.
In the United States Patent and Trademark Office, Non-Final Office Action in re: U.S. Appl. No. 11/317,574, dated Sep. 30, 2008, 28 pages.
In the United States Patent and Trademark Office, Non-Final Office Action in re: U.S. Appl. No. 10/951,357, dated Nov. 26, 2008, 23 pages.
In the United States Patent and Trademark Office, Non-Final Office Action in re: U.S. Appl. No. 11/315,943, dated Feb. 20, 2009, 17 pages.
In the United States Patent and Trademark Office, Non-Final Office Action in re: U.S. Appl. No. 11/611,602, dated Mar. 3, 2009, 18 pages.
In the United States Patent and Trademark Office, Non-Final Office Action in re: U.S. Appl. No. 11/297,778, dated Mar. 9, 2009, 12 pages.
In the United States Patent and Trademark Office, Non-Final Office Action in re: U.S. Appl. No. 11/481,481, dated Mar. 20, 2009, 48 pages.
In the United States Patent and Trademark Office, Final Office Action in re: U.S. Appl. No. 11/315,897, dated Mar. 20, 2009, 21 pages.
In the United States Patent and Trademark Office, Non-Final Office Action in re: U.S. Appl. No. 11/481,480, dated Mar. 20, 2009, 50 pages.
In the United States Patent and Trademark Office, Final Office Action in re: U.S. Appl. No. 11/321,863, dated Feb. 12, 2009, 24 pages.
In the United States Patent and Trademark Office, Final Office Action in re: U.S. Appl. No. 11/322,003 dated Feb. 13, 2009, 24 pages.
In the United States Patent and Trademark Office, Final Office Action in re: U.S. Appl. No. 11/322,372 dated Feb. 13, 2009, 22 pages.
In the United States Patent and Trademark Office, Non-Final Office Action in re: U.S. Appl. No. 11/304,091 dated Feb. 27, 2009, 36 pages.
In the U.S. Patent and Trademark Office, Final Office Action in re: U.S. Appl. No. 11/321,863, dated Aug. 7, 2009, 15 pages.
In the U.S. Patent and Trademark Office, Final Office Action in re: U.S. Appl. No. 11/321,864, dated Aug. 17, 2009, 16 pages.
In the U.S. Patent and Trademark Office, Final Office Action in re: U.S. Appl. No. 11/321,863, dated Jan. 7, 2010, 16 pages.
In the U.S. Patent and Trademark Office, Final Office Action in re: U.S. Appl. No. 11/321,864, dated Jan. 27, 2010, 17 pages.
In the U.S. Patent and Trademark Office, Non-Final Office Action in re: U.S. Appl. No. 11/315,969, dated Jan. 27, 2010, 14 pages.
In the U.S. Patent and Trademark Office, Non-Final Office Action in re: U.S. Appl. No. 11/481,456, dated May 14, 2010, 9 pages.

(56) References Cited

OTHER PUBLICATIONS

In the U.S. Patent and Trademark Office, Non-Final Office Action in re: U.S. Appl. No. 11/481,481, dated May 13, 2010, 9 pages.
In the U.S. Patent and Trademark Office, Final Office Action in re: U.S. Appl. No. 11/315,897, dated May 14, 2010, 13 pages.
In the U.S. Patent and Trademark Office, Non-Final Office Action in re: U.S. Appl. No. 11/481,480, dated May 17, 2010, 10 pages.
In the U.S. Patent and Trademark Office, Non-Final Office Action in re: U.S. Appl. No. 11/321,864, dated Jan. 8, 2009, 18 pages.
In the U.S. Patent and Trademark Office, Non-Final Office Action in re: U.S. Appl. No. 10/877,445, dated Mar. 19, 2009, 23 pages.
In the U.S. Patent and Trademark Office, Non-Final Office Action in re: U.S. Appl. No. 11/315,898, dated Feb. 18, 2009, 18 pages.
In the U.S. Patent and Trademark Office, Non-Final Office Action in re: U.S. Appl. No. 11/317,574, dated Apr. 29, 2009, 29 pages.
In the U.S. Patent and Trademark Office, Final Office Action in re: U.S. Appl. No. 11/315,969, dated Sep. 29, 2009, 7 pages.
In the U.S. Patent and Trademark Office, Advisory Action in re: U.S. Appl. No. 11/322,372, dated May 12, 2009, 13 pages.
In the U.S. Patent and Trademark Office, Final Office Action in re: U.S. Appl. No. 11/322,372, dated Aug. 6, 2009, 13 pages.
In the U.S. Patent and Trademark Office, Final Office Action in re: U.S. Appl. No. 11/481,456, dated Oct. 9, 2009, 18 pages.
In the U.S. Patent and Trademark Office, Final Office Action in re: U.S. Appl. No. 10/877,445, dated Aug. 25, 2009, 21 pages.
In the U.S. Patent and Trademark Office, Final Office Action in re: U.S. Appl. No. 11/315,969, dated May 13, 2009, 14 pages.
In the U.S. Patent and Trademark Office, Non-Final Office Action in re: U.S. Appl. No. 11/317,574, dated Dec. 28, 2009, 26 pages.
In the U.S. Patent and Trademark Office, Non-Final Office Action in re: U.S. Appl. No. 11/315,943, dated Feb. 19, 2010, 16 pages.
In the U.S. Patent and Trademark Office, Final Office Action in re: U.S. Appl. No. 11/316,104, dated Mar. 24, 2010, 19 pages.
In the U.S. Patent and Trademark Office, Final Office Action in re: U.S. Appl. No. 10/877,445, dated Jul. 8, 2010, 21 pages.
Bruder et al., "Mesenchymal Stem Cell Surface Antigen SB-10 Corresponds to Activated Leukocyte Cell Adhesion Molecule and Is Involved in Osteogenic Differentiation," *Journal of Bone and Mineral Research*, 1998; 13(4):655-663.
Diegelmann et al., "Inhibition of Collagen Secretion from Bone and Cultured Fibroblasts by Microtubular Disruptive Drugs," *Proc., Nat. Acad. Sci.*, 1972; 69(4):892-896.
Gronthos et al., "Postnatal Human Dental Pulp Stem Cells (DPSCs) *In Vitro* and *In Vivo*," *PNAS*, 2000; 97(25): 13625-13630.
Liddiard, et al., "An Improved Method for the Preparation of Human Fetal and Adult Hepatocytes," *Arch. Toxicol.*, 1980; 44(1-3):107-112.
Wexler, S. A. et al., "Adult Bone Marrow is a Rich Source of Human Mesenchymal 'Stem' Cells but Umbilical Cord and Mobilized Adult Blood are Not," *British Journal of Haematology*, 2003; 121:368-374.
In the U.S. Patent and Trademark Office, Final Office Action in re: U.S. Appl. No. 11/321,863, dated Aug. 17, 2010, 15 pages.
In the U.S. Patent and Trademark Office, Final Office Action in re: U.S. Appl. No. 11/322,372, dated Aug. 31, 2010, 11 pages.
In the U.S. Patent and Trademark Office, Final Office Action in re: U.S. Appl. No. 11/321,864, dated Aug. 31, 2010, 7pages.
In the U.S. Patent and Trademark Office, Final Office Action in re: U.S. Appl. No. 11/315,969, dated Aug. 31, 2010, 6 pages.
In the U.S. Patent and Trademark Office, Non-Final Office Action in re: U.S. Appl. No. 11/316,104, dated Sep. 21, 2010, 13 pages.
In the U.S. Patent and Trademark Office, Final Office Action in re: U.S. Appl. No. 11/317,574, dated Oct. 6, 2010, 16 pages.
In the U.S. Patent and Trademark Office, Non-Final Office Action in re: U.S. Appl. No. 11/322,372, dated Jan. 21, 2010, 10 pages.
In the U.S. Patent and Trademark Office, Final Office Action in re: U.S. Appl. No. 11/481,481, dated Sep. 18, 2009, 11 pages.
In the U.S. Patent and Trademark Office, Advisory Action in re: U.S. Appl. No. 11/315,897, dated Jun. 30, 2009, 3 pages.
In the U.S. Patent and Trademark Office, Non-Final Office Action in re: U.S. Appl. No. 11/315,897, dated Sep. 2, 2009, 12 pages.
In the U.S. Patent and Trademark Office, Final Office Action in re: U.S. Appl. No. 11/481,480, dated Sep. 17, 2009, 12 pages.
In the U.S. Patent and Trademark Office, Final Office Action in re: U.S. Appl. No. 10/877,446, dated Jun 4, 2010, 17 pages.
In the U.S. Patent and Trademark Office, Non-Final Office Action in re: U.S. Appl. No. 11/316,104, dated Oct. 31, 2008, 15 pages.
In the U.S. Patent and Trademark Office, Final Office Action in re: U.S. Appl. No. 11/322,003, dated Feb. 13, 2009, 17 pages.
Linkhart et al., Growth Factors for Bone Growth and Repair: IGF, TGFβ and BMP[1], *Bone*, 1996; 19(Suppl 1):1S-12S.
In the U.S. Patent and Trademark Office, Non-Final Office Action in re: U.S. Appl. No. 11/481,456, dated Feb. 3, 2011, 10 pages.
In the U.S. Patent and Trademark Office, Non-Final Office Action in re: U.S. Appl. No. 11/481,481, dated Feb. 3, 2011, 10 pages.
In the U.S. Patent and Trademark Office, Non-Final Office Action in re: U.S. Appl. No. 12/389,305, dated Feb. 8, 2011, 14 pages.
In the U.S. Patent and Trademark Office, Non-Final Office Action in re: U.S. Appl. No. 11/481,480, dated Feb. 3, 2011, 10 pages.
In the U.S. Patent and Trademark Office, Final Office Action in re: U.S. Appl. No. 10/877,446, dated Nov. 2, 2011, 12 pages.
In the U.S. Patent and Trademark Offiice, Final Office Action in re: U.S.Appl. No. 12/389,305 dated Oct. 12, 2011, 12 pages.
In the U.S. Patent and Trademark Office, Final Office Action in re: U.S. Appl. No. 12/429,849, dated Mar. 20, 2012, 9 pages.
In the U.S. Patent and Trademark Office, Final Office Action in re: U.S. Appl. No. 11/481,456, dated Oct. 11, 2011, 6 pages.
In the U.S. Patent and Trademark Office, Non-Final Office Action in re: U.S. Appl. No. 12/697,081, dated Apr. 2, 2012, 8 pages.
In the U.S. Patent and Trademark Office, Non-Final Office Action in re: U.S. Appl. No. 13/605,716, dated Feb. 13, 2013, 13 pages.
Bakhshi, et al. "Mesenchymal stem cells from the Wharton's jelly of umbilical cord segments provide stromal support for the maintenance of cord blood hematopoietic stem cells during long-term ex vivo culture", *Transfusion*, 2008; 48: 2638-2644.
Cell Isolation Theory, in Tissue Dissociation Guide, Worthington Biochemical, accessible at http://www.tissuedissociation.com, accessed Aug. 8, 2007.
Draper et al., "Surface Antigens of Human Embryonic Stem Cells: Changes Upon Differentiation in Culture," *J. Anat.*, 2002; 200:249-258.
Igura et al. "Human Placental Derived Stem Cells Differentiate into Neural Cells," *Blood*, 2002; 100(11): 517A (Abstract 2021).
Kusama et al., "Growth and morphogenesis of mouse prostate epithelial cells in collagen gel matrix culture" Cell Biol Int Rep, 1989; 13:569-575.
Makino et al., "Cardiomyocytes can be generated from marrow stromal cells in vitro," J. Clin. Invest., 1999; 103:697-705.
Naughton et al., "Cells isolated from Wharton's jelly of the human umbilical cord develop a cartilage phenotype when treated with TGF-b in vitro," 1997; FASEB J 11:A19 (Abstract 108).
Seaver et al. "The chick oviduct in tissue culture. I. Initial characterization of growing primary oviduct tissue cultures," Exp. Cell Res., 1984; 155: 241-251.
Seiji, T. et al., Possibility of Regenerative Medicine Using Human Amniotic Cells, Regenerative Medicine, 2002; 1(2):79-85.
Wang, Y. et al., "Enhanced Recovery of Hematopoietic Progenitor and Stem Cells from Cultivated, Postpartum Human Placenta," Blood, 2001; 98(11): 183a (Abstract 769).
In the U.S. Patent and Trademark Office, Final Office Action in re: U.S. Appl. No. 11/317,574, dated Jul. 11, 2013, 29 pages.
In the U.S. Patent and Trademark Office, Non-Final Office Action in re: U.S. Appl. No. 11/322,372, dated Jan. 16, 2014, 17 pages.
In the U.S. Patent and Trademark Office, Non-Final Office Action in re: U.S. Appl. No. 11/321,864, dated Jan. 29, 2014, 9 pages.
In the U.S. Patent and Trademark Office, Non-Final Office Action in re: U.S. Appl. No. 11/321,863, dated Jan. 31, 2014, 17 pages.
In the U.S. Patent and Trademark Office, Non-Final Office Action in re: U.S. Appl. No. 10/876,998, dated Feb. 11, 2014, 14 pages.
In the U.S. Patent and Trademark Office, Non-Final Office Action in re: U.S. Appl. No. 12/389,305, dated Mar. 6, 2014, 37 pages.

(56) References Cited

OTHER PUBLICATIONS

In the U.S. Patent and Trademark Office, Non-Final Office Action in re: U.S. Appl. No. 11/316,104, dated Mar. 14, 2014, 11 pages.
In the U.S. Patent and Trademark Office, Non-Final Office Action in re: U.S. Appl. No. 12/389,305, dated Mar. 21, 2014, 47 pages.
In the U.S. Patent and Trademark Office, Non-Final Office Action in re: U.S. Appl. No. 10/877,446, dated Mar. 21, 2014, 21 pages.
In the U.S. Patent and Trademark Office, Non-Final Office Action in re: U.S. Appl. No. 11/316,104, dated Mar. 21, 2014, 20 pages.
In the U.S. Patent and Trademark Office, Non-Final Office Action in re: U.S. Appl. No. 11/315,969, dated Mar. 21, 2014, 15 pages.
Baksh, D. et al., "Comparison of proliferative and multilineage differentiation potential of human mesenchymal stem cells derived from umbilical cord and bone marrow." *Stem Cells*, 2007; 25: 1384-1392.
Bhatia, R. et al., "A clinically suitable ex vivo expansion culture system for LTC-IC and CFC using stroma-conditioned medium," *Exp Hematol.*, 1997; 25(9): 980-91 (Abstract only).
Covas, D.T. et al., "Isolation and culture of umbilical vein mesenchymal stem cells." *Brazilian Journal of Medical and Biological Research*, 2003; 36: 1179-1183.
Henderson, G.I. et al., "Inhibition of placental valine uptake after acute and chronic maternal ethanol consumption." *J Pharmacol Exp Therap*, 1981; 216: 465-472.
Kestendjieva, S. et al., "Characterization of mesenchymal stem cells isolated from the human umbilical cord." *Cell Biology International*, 2008; 32: 724-732.
Kocher, A. A. et al., "Neovascularization of ischemic myocardium by human bone-marrow-derived angioblasts prevents cardiomyocyte apoptosis, reduces remodeling and improves cardiac function," *Nature Medicine*, 2001; 7:430-6.
Voet D. and Voet J.G., *Biochemistry* (2d Ed., John Wiley & Sons). 1995, p. 64.
In the U.S. Patent and Trademark Office, Final Office Action in re: U.S. Appl. No. 11/317,574, dated Feb. 3, 2014, 16 pages.
In the U.S. Patent and Trademark Office, Final Office Action in re: U.S. Appl. No. 12/389,305, dated Aug. 6, 2014, 57 pages.
In the U.S. Patent and Trademark Office, Final Office Action in re: U.S. Appl. No. 10/877,446, dated Aug. 6, 2014, 35 pages.
In the U.S. Patent and Trademark Office, Final Office Action in re: U.S. Appl. No. 11/316,104, dated Aug. 6, 2014, 18 pages.
In the U.S. Patent and Trademark Office, Non-Final Office Action in re: U.S. Appl. No. 11/611,602, dated Oct. 9, 2014, 15 pages.
In the U.S. Patent and Trademark Office, Final Office Action in re: U.S. Appl. No. 11/317,574, dated Feb. 3, 2014, 12 pages.
In the U.S. Patent and Trademark Office, Final Office Action in re: U.S. Appl. No. 11/321,864, dated Nov. 3, 2014, 10 pages.
In the U.S. Patent and Trademark Office, Non-Final Office Action in re: U.S. Appl. No. 11/322,372, dated Nov. 25, 2014, 24 pages.
In the U.S. Patent and Trademark Office, Final Office Action in re: U.S. Appl. No. 11/315,969, dated Dec. 18, 2014, 30 pages.
In the U.S. Patent and Trademark Office, Final Office Action in re: U.S. Appl. No. 11/321,863, dated Jan. 31, 2014, 17 pages.
"11885—DMEM, low glucose, pyruvate." Life Technologies. Available online at <http://www.lifetechnolgies.com/us/en/home/technical-resources/media-formulation.48.html>. Accessed Jul. 31, 2014. 2 pages.
Hass, R. et al., "Different populations and sources of human mesenchymal stem cells (MSC): A comparison of adult and neonatal tissue-derived MSC," *Cell Communication and Signaling*, 2011; 9:12, p. 1-14.
Ho, A.D. et al., "Heterogeneity of mesenchymal stromal cell preparations," *Cytotherapy*, 2008;10(4):320-30.
Mattsson, J. et al. "Graft Failure after Allogenic Hematopoietic Cell Transplantation," *Biol Blood Marrow Transplant*, 2008; 14 (Supplement 1): 165-170.
Mineo, D. et al., "Combined Islet and Hematopoietic Stem Cell Allotransplantation: A Clinical Pilot Trial to Induce Chimerism and Graft Tolerance, " *American Journal of Transplantation*, 2008; 8:1262-1274.

Park, B-G et al., "Development of high density mammalian cell culture system for the production of tissue-type plasminogen activator," *Biotechnology and Bioprocess Engineering*, 2000; 5:123-129.
Pittenger, M.F. et al.; "Human mesenchymal stem cells: progenitor cells for cartilage, bone, fat and stroma," *Current Topics in Microbiology and Immunology*, 2000; 251:3-11.
Rachakatla, R. S. et al., "Development of Human Umbilical Cord Matrix Stem Cell-Based Gene Therapy for Experimental Lung Tumors," *Cancer Gene Therapy*, 2007; 14:828-835.
Secco, M. et al., "Multipotent Stem Cells from Umbilical Cord: Cord is Richer than Blood!" *Stem Cells*, 2008; 26:146-150.
Solomon, D. E., "An in vitro examination of extracellular matrix scaffold for use in wound healing," *Int. J. Path*, 2002, 93: 209-216.
Troyer, D. L. et al., "Concise Review: Wharton's Jelly-Derived Cells Are a Primitive Stromal Cell Population," *Stem Cells*, 2008; 26:591-599.
In the U.S. Patent and Trademark Office, Non-Final Office Action in re: U.S. Appl. No. 14/152,649, dated Feb. 26, 2015, 9 pages.
In the U.S. Patent and Trademark Office, Non-Final Office Action in re: U.S. Appl. No. 14/444,689, dated Mar. 24, 2015, 9 pages.
In the U.S. Patent and Trademark Office, Final Office Action in re: U.S. Appl. No. 11/317,574, dated Apr. 1, 2015, 12 pages.
In the U.S. Patent and Trademark Office, Final Office Action in re: U.S. Appl. No. 13/471,095, dated Jun. 12, 2015, 10 pages.
In the U.S. Patent and Trademark Office, Final Office Action in re: U.S. Appl. No. 14/152,649, dated Jul. 10, 2015, 7 pages.
In the U.S. Patent and Trademark Office, Final Office Action in re: U.S. Appl. No. 12/339,872, dated Aug. 3, 2015, 14 pages.
In the U.S. Patent and Trademark Office, Non-Final Office Action in re: U.S. Appl. No. 10/877,446, dated Sep. 3, 2015, 82 pages.
In the U.S. Patent and Trademark Office, Non-Final Office Action in re: U.S. Appl. No. 11/321,864, dated Sep. 2, 2015, 11 pages.
In the U.S. Patent and Trademark Office, Non-Final Office Action in re: U.S. Appl. No. 12/389,305, dated Sep. 4, 2015, 63 pages.
In the U.S. Patent and Trademark Office, Final Office Action in re: U.S. Appl. No. 11/316,104, dated Sep. 8, 2015, 63 pages.
In the U.S. Patent and Trademark Office, Non-Final Office Action in re: U.S. Appl. No. 14/152,649, dated Oct. 27, 2015, 7 pages.
Broxmeyer, H.E. et al., "Growth characteristics and expansion of human umbilical cord blood and estimation of its potential for transplantation in adults," *PNAS*, 1992; 89(9): 4109-4113.
Chen, K. et al., "Human umbilical cord mesenchymal stem cells hUC-MSCs exert immunosuppressive activities through a PGE2-dependent mechanism," *Clinical Immunology*, 2010, 135; 448-458.
Kern, S. et al., "Comparative analysis of mesenchymal stem cells from bone marrow, umbilical cord blood, or adipose tissue," *Stem Cells*, 2006; 24(5):1294-301.
Otsuka, A. et al. "Lipopolysaccharide augments HLA-A,B,C molecule expression but inhibits interferon-gamma-induced HLA-DR molecule expression on cultured human endothelial cells," *Immunology*, 1991; 73; 428-432.
Xu, Y et al., "Umbilical Cord-Derived Mesenchymal Stem Cells Isolated by a Novel Explantation Technique Can Differentiate into Functional Endothelial Cells and Promote Revascularization," *Stem Cells and Development*, 2010, 19(10): 1511-1522.
Zhao, Q.H. et al., "Biological characteristics of human umbilical cord-derived mesenchymal stem cells and their differentiation into chondrogenic and osteogenic cells," *Zhonghua Yi Xue Za Zhi.*, 2011;91(5):317-21 (Abstract only).
In the U.S. Patent and Trademark Office, Final Office Action in re: U.S. Appl. No. 11/321,864, dated Dec. 22, 2015, 15 pages.
In the U.S. Patent and Trademark Office, Non-Final Office Action in re: U.S. Appl. No. 11/317,574, dated Jan. 6, 2015, 11 pages.
In the U.S. Patent and Trademark Office, Final Office Action in re: U.S. Appl. No. 11/322,372, dated Jan. 6, 2015, 27 pages.
Mankikar, S.D., "Stem Cells: A New Paradigm in Medical Therapeutics," *Journal of Long-Term Effects of Medical Implants*, 2010; 20:219-250.
In the U.S. Patent and Trademark Office, Final Office Action in re: U.S. Appl. No. 12/337,439, dated Mar. 17, 2016 29 pages.
In the U.S. Patent and Trademark Office, Final Office Action in re: U.S. Appl. No. 11/351,969, dated Apr. 21, 2016 20 pages.

(56) References Cited

OTHER PUBLICATIONS

In the U.S. Patent and Trademark Office, Final Office Action in re: U.S. Appl. No. 12/389,305, dated May 24, 2016 21 pages.
In the U.S. Patent and Trademark Office, Final Office Action in re: U.S. Appl. No. 11/316,104, dated May 24, 2016 24 pages.
In the U.S. Patent and Trademark Office, Non-Final Office Action in re: U.S. Appl. No. 10/877,446, dated May 24, 2016 36 pages.
In the U.S. Patent and Trademark Office, Non-Final Office Action in re: U.S. Appl. No. 11/322,372, dated May 31, 2016, 29 pages.
In the U.S. Patent and Trademark Office, Final Office Action in re: U.S. Appl. No. 11/317,574, dated May 31, 2016, 18 pages.
In the U.S. Patent and Trademark Office, Final Office Action in re: U.S. Appl. No. 14/152,649, dated Jun. 14, 2016, 6 pages.
In the U.S. Patent and Trademark Office, Final Office Action in re: U.S. Appl. No. 11/317,574, dated Jul. 7, 2016, 9 pages.
Baksh, D. et al., "Adult mesenchymal stem cells: characterization, differentiation, and application in cell and gene therapy", *J Cell Mol Med.*, 2004; 8(3):301-16.
Lu, L.L. et al., "Isolation and characterization of human umbilical cord mesenchymal stem cells with hematopoiesis-supportive function and other potentials," *Haematologica*, 2006; 91(8):1017-26.
Naughton, B.A. et al., "Hematopoiesis on nylon mesh templates. I. Long-term culture of rat bone marrow cells," *Journal of Medicine*, 1987; 18(3-4):219-50.
Wakitani, S. et al., "Mesenchymal cell-based repair of large, full-thickness defects of articular cartilage", *J Bone Joint Surg Am*, 1994; 76(4): 579-592.
Weiss, M.L. et al., "Stem Cells in the Umbilical Cord," *Stem Cell Rev.*, 2006; 2(2):155-162.
In the U.S. Patent and Trademark Office, Final Office Action in re: U.S. Appl. No. 13/722,849, dated Jul. 28, 2016, 18 pages.
In the U.S. Patent and Trademark Office, Final Office Action in re: U.S. Appl. No. 12/337,439, dated Aug. 19, 2016, 36 pages.
In the U.S. Patent and Trademark Office, Final Office Action in re: U.S. Appl. No. 14/018,842, dated Oct. 20, 2016, 17 pages.
In the U.S. Patent and Trademark Office, Non-Final Office Action in re: U.S. Appl. No. 12/339,872, dated Nov. 3, 2016, 15 pages.
In the U.S. Patent and Trademark Office, Non-Final Office Action in re: U.S. Appl. No. 11/321,863, dated Nov. 9, 2016, 28 pages.
In the U.S. Patent and Trademark Office, Non-Final Office Action in re: U.S. Appl. No. 11/315,969, dated Nov. 9, 2016, 19 pages.
In the U.S. Patent and Trademark Office, Non-Final Office Action in re: U.S. Appl. No. 11/321,864, dated Nov. 14, 2016, 20 pages.
In the U.S. Patent and Trademark Office, Final Office Action in re: U.S. Appl. No. 11/871,045, dated Nov. 17, 2016, 14 pages.
In the U.S. Patent and Trademark Office, Non-Final Office Action in re: U.S. Appl. No. 13/471,095, dated Nov. 22, 2016, 15 pages.
In the U.S. Patent and Trademark Office, Non-Final Office Action in re: U.S. Appl. No. 12/642,775, dated Nov. 23, 2016, 50 pages.
In the U.S. Patent and Trademark Office, Final Office Action in re: U.S. Appl. No. 12/642,774, dated Dec. 9, 2016, 11 pages.
Ding et al., "Enhancement of neuroplasticity through upregulation of $\beta$1-integrin in human umbilical cord-derived stromal cell implanted stroke model," Neurobiology of Disease, 2007; 27:339-353.
Aldskogius, H. et al., "Strategies for repair of the deafferented spinal cord," *Brain Res. Rev.*, 2002, 20, 301-308.
Armulik A et al., "Endothelial/Pericyte Interactions," *Circ. Res.*, 2005, 97, 512-23.
Bergers G. et al., "The role of pericytes in blood-vessel formation and maintenance," *Neuro-Oncology*, 7, 452-464 2005.
Daley, G. Q. et al., "Realistic Prospects for Stem Cell Therapeutics," *Hematol.*, 2003, 398-418.
Kawata, M. et al., "Transcriptional control of HLA-A,B,C antigen in human placental cytotrophoblast isolated using trophoblast- and HLA-specific monoclonal antibodies and the fluorescence-activated cell sorter," *J. Exp. Med.*, Sep. 1984, 160, 633-651.
Kirschstein, R. et al., "Can stem cells repair a damaged heart?" *Stem Cells: Scientific Progress and Future Research Directions*, 2001, 87-92.
Lindvall, O. et al., "Stem cell therapy for human neurodegenerative disorders—how to make it work," *Nature Medicine*, Jul. 2004, 542-550.
Nishishita, T. et al., "A potential pro-angiogenic cell therapy with human placenta-derived mesenchymal cells," *Biochemical and Biophysical Research Communications*, 2004, 325, 24-31.
Rehman, J. et al., "Secretion of Angiogenic and Antiapoptotic Factors by Human Adipose Stromal Cells," *Circulation*, 2004, 109, 1292-1298.
Roskams, A. J. et al., "Directing stem cells and progenitor cells on the stage of spinal cord injury," *Exp. Neurol.*, 2005, 193, 267-272.
Urbich, C. et al., "Endothelial Progenitor Cells,", *Circ. Res.*, 2004, 95, 343-353.
Yang Chen et al., "Enhancement of neovascularization with cord blood CD133$^+$ cell-derived endothelial progenitor cell transplantation," *Thrombosis and Haemostasis*, Jun. 2004, 91(6), 1202-1212.

\* cited by examiner

CARTILAGE AND BONE REPAIR AND REGENERATION USING POSTPARTUM-DERIVED CELLS

CROSS-REFERENCE TO RELATED APPLICATIONS

This application claims benefit under 35U.S.C 119(e) of U.S. Provisional Application No. 60/483,264, filed Jun. 27, 2003, the entire contents of which are incorporated by reference herein.

This application is also related to the following commonly-owned, co-pending applications, the entire contents of each of which are incorporated by reference herein: U.S. application Ser. No. 10/877,012, filed Jun. 25, 2004, U.S. application Ser. No. 10/877,446, filed Jun. 25, 2004, U.S. application Ser. No. 10/877,269, filed Jun. 25, 2004, U.S. application Ser. No. 10/877,445, filed Jun. 25, 2004, U.S. application Ser. No. 10/877,541, filed Jun. 25, 2004, U.S. application Ser. No. 10/877,009, filed Jun. 25, 2004 and U.S. Provisional Application No. 60/555,908, filed Mar. 24, 2004.

FIELD OF THE INVENTION

This invention relates to the field of mammalian cell biology and cell culture. In particular, the invention relates to cells derived from postpartum tissue having the potential to differentiate into chondrogenic and osteogenic lineages, and methods of preparation and use of those postpartum tissue-derived cells, including cell-based therapies for conditions of bone and cartilage.

BACKGROUND OF THE INVENTION

Diseases and conditions of bone and cartilage affect a large portion of the population. Three types of cartilage are present in mammals and include: hyaline cartilage, fibro-cartilage, and elastic cartilage. Hyaline cartilage consists of a gristly mass having a firm, elastic consistency, is translucent and pearly blue in color. Hyaline cartilage is predominantly found on the articulating surfaces of articulating joints. It is found also in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. The collagenous fibers are arranged in bundles, with the cartilage cells located between the bundles. Fibrocartilage is found commonly in the annulus fibrosis of the invertebral disc, tendonous and ligamentous insertions, menisci, the symphysis pubis, and insertions of joint capsules. Elastic cartilage also is similar to hyaline cartilage except that it contains fibers of elastin. It is more opaque than hyaline cartilage and is more flexible and pliant. These characteristics are defined in part by the elastic fibers embedded in the cartilage matrix. Typically, elastic cartilage is present in the pinna of the ears, the epiglottis, and the larynx.

The surfaces of articulating bones in mammalian joints are covered with articular cartilage. The articular cartilage prevents direct contact of the opposing bone surfaces and permits the near frictionless movement of the articulating bones relative to one another. Two types of articular cartilage defects are commonly observed in mammals and include full-thickness and partial-thickness defects. The two types of defects differ not only in the extent of physical damage but also in the nature of repair response each type of lesion elicits.

Full-thickness articular cartilage defects include damage to the articular cartilage, the underlying subchondral bone tissue, and the calcified layer of cartilage located between the articular cartilage and the subchondral bone. Full-thickness defects typically arise during severe trauma of the joint or during the late stages of degenerative joint diseases, for example, during osteoarthritis. Since the subchondral bone tissue is both innervated and vascularized, damage to this tissue is often painful. The repair reaction induced by damage to the subchondral bone usually results in the formation of fibrocartilage at the site of the full-thickness defect. Fibrocartilage, however, lacks the biomechanical properties of articular cartilage and fails to persist in the joint on a long term basis.

Partial-thickness articular cartilage defects are restricted to the cartilage tissue itself. These defects usually include fissures or clefts in the articulating surface of the cartilage. Partial-thickness defects are caused by mechanical arrangements of the joint which in turn induce wearing of the cartilage tissue within the joint. In the absence of innervation and vasculature, partial-thickness defects do not elicit repair responses and therefore tend not to heal. Although painless, partial-thickness defects often degenerate into full-thickness defects.

Cartilage may develop abnormally or may be damaged by disease, such as rheumatoid arthritis or osteoarthritis, or by trauma, each of which can lead to physical deformity and debilitation. Whether cartilage is damaged from trauma or congenital anomalies, its successful clinical regeneration is often poor at best, as reviewed by Howell, et al. Osteoarthritis: Diagnosis and Management, 2nd ed., (Philadelphia, W. B. Saunders, 1990) and Kelley, et al. Textbook of Rheumatology, 3rd ed., (Philadelphia, W. B. Saunders, 1989).

Bone conditions also are widespread. For example, there generally are two types of bone conditions: non-metabolic bone conditions, such as bone fractures, bone/spinal deformation, osteosarcoma, myeloma, bone dysplasia and scoliosis, and metabolic bone conditions, such as osteoporosis, osteomalacia, rickets, fibrous osteitis, renal bone dystrophy and Paget's disease of bone. Osteoporosis, a metabolic bone condition, is a systemic disease characterized by increased bone fragility and fracturability due to decreased bone mass and change in fine bone tissue structure, its major clinical symptoms including spinal kyphosis, and fractures of dorsolumbar bones, vertebral centra, femoral necks, lower end of radius, ribs, upper end of humerus, and others. In bone tissue, bone formation and destruction due to bone resorption occur constantly. Upon deterioration of the balance between bone formation and bone destruction due to bone resorption, a quantitative reduction in bone occurs. Traditionally, bone resorption suppressors such as estrogens, calcitonin and bisphosphonates have been mainly used to treat osteoporosis.

Bone grafting is often used for the treatment of bone conditions. Indeed, more than 1.4 million bone grafting procedures are performed in the developed world annually. Most of these procedures are administered following joint replacement surgery or during trauma surgical reconstruction. The success or failure of bone grafting is dependent upon a number of factors including the vitality of the site of the graft, the graft processing, and the immunological compatibility of the engrafted tissue.

In view of the prevalence of bone and cartilage conditions, novel sources of bone and cartilage tissue for therapeutic, diagnostic, and research uses are in high demand.

SUMMARY OF THE INVENTION

The invention is generally directed to postpartum-derived cells which are derived from postpartum tissue which is substantially free of blood and which is capable of self-renewal and expansion in culture and having the potential to differentiate into a cell of osteocyte or chondrocyte phenotypes.

In some embodiments, the present invention provides cells derived from human postpartum tissue substantially free of blood, capable of self-renewal and expansion in culture, having the potential to differentiate into a cell of an osteogenic or chondrogenic phenotype; requiring L-valine for growth; capable of growth in about 5% to about 20% oxygen; and further having at least one of the following characteristics:

production of at least one of GCP-2, tissue factor, vimentin, and alpha-smooth muscle actin;

lack of production of at least one of NOGO-A, GRO-alpha or oxidized low density lipoprotein receptor, as detected by flow cytometry;

production of at least one of CD10, CD13, CD44, CD73, CD90, PDGFr-alpha, PD-L2 and HLA-A, B, C;

lack of production of at least one of CD31, CD34, CD45, CD80, CD86, CD117, CD141, CD178, B7-H2, HLA-G, and HLA-DR, DP, DQ, as detected by flow cytometry;

expression, which relative to a human cell that is a fibroblast, a mesenchymal stem cell, or an iliac crest bone marrow cell, is increased for at least one of interleukin 8; reticulon 1;

chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; tumor necrosis factor, alpha-induced protein 3 or expression, which relative to a human cell that is a fibroblast, a mesenchymal stem cell, or an iliac crest bone marrow cell, is increased for at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113;

expression, which relative to a human cell that is a fibroblast, a mesenchymal stem cell, or an iliac crest bone marrow cell, is reduced for at least one of: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; and insulin-like growth factor binding protein 2, 36 kDa;

secretion of at least one of MCP-1, IL-6, IL-8, GCP-2, HGF, KGF, FGF, HB-EGF, BDNF, TPO, MIP1a, RANTES, and TIMP1;

lack of secretion of at least one of TGF-beta2, ANG2, PDGFbb, MIP1b, I309, MDC, and VEGF, as detected by ELISA; and the ability to undergo at least 40 population doublings in culture.

In certain embodiments, the postpartum-derived cell is an umbilical cord-derived cell. In other embodiments, it is a placenta-derived cell. In specific embodiments, the cell has all identifying features of any one of: cell type PLA 071003 (P8) (ATCC Accession No. PTA-6074); cell type PLA 071003 (P11) (ATCC Accession No. PTA-6075); cell type PLA 071003 (P16) (ATCC Accession No. PTA-6079); cell type UMB 022803 (P7) (ATCC Accession No. PTA-6067); or cell type UMB 022803 (P17) (ATCC Accession No. PTA-6068). The postpartum-derived cells of the invention are preferably human cells.

The cells may be induced to differentiate to an osteogenic or chondrogenic phenotype. Methods for inducing differentiation of postpartum-derived cells of the invention are contemplated. For example, the cells may be induced to differentiate to a cell having an osteogenic or chondrogenic phenotype. Methods of inducing differentiation of the cells of the invention preferably involve exposing the cells to one or more differentiation-inducing agents. Osteogenesis inducing agents of the invention include bone morphogenic proteins (e.g., BMP-2, BMP-4) and transforming growth factor (TGF)-beta1, and combinations thereof. Chondrogenesis inducing agents of the invention include TGF-beta3, GDF-5, and a combination thereof. The invention includes the differentiation-induced cells and populations, compositions, and products thereof. Differentiation-induced cells of an osteogenic lineage preferably express at least one osteogenic lineage marker (e.g., osteocalcin, bone sialoprotein, alkaline phosphatase). Differentiation of PPDCs to an osteogenic lineage may be assessed by any means known in the art, for example but not limited to, measurement of mineralization (e.g., von Kossa staining). Differentiation-induced cells of a chondrogenic lineage preferably express at least one chondrogenic lineage marker (e.g., glycosaminoglycan, type II collagen). Differentiation of PPDCs to a chondrogenic lineage may be assessed by any means known in the art, for example but not limited to, Safranin-O or hematoxylin/eosin staining.

Populations of PPDCs are provided by the invention. The PPDCs may be differentiation-induced or undifferentiated.

In some embodiments, a population of postpartum-derived cells is mixed with another population of cells. In some embodiments, the cell population is heterogeneous. A heterogeneous cell population of the invention may comprise at least about 5%, 10%, 20%, 30%, 40%, 50%, 60%, 70%, 80%, 90%, or 95% undifferentiated or differentiation-induced PPDCs of the invention. The heterogeneous cell populations of the invention may further comprise bone marrow cells, stem cells, chondroblasts, chondrocytes, osteoblasts, osteocytes, osteoclasts, bone lining cells, or other bone or cartilage cell progenitors. Cell populations of the invention may be substantially homogeneous, i.e., comprises substantially only PPDCs (preferably at least about 96%, 97%, 98%, 99% or more PPDCs). The homogeneous cell population of the invention may comprise umbilical cord- or placenta-derived cells. Homogeneous populations of placenta-derived cells may be of neonatal or maternal lineage. Homogeneity of a cell population may be achieved by any method known in the art, for example, by cell sorting (e.g., flow cytometry), bead separation, or by clonal expansion.

The invention also provides heterogeneous and homogeneous cell cultures containing undifferentiated or differentiation-induced postpartum-derived cells of the invention.

Some embodiments of the invention provide a matrix for implantation into a patient seeded with one or more postpartum-derived cells of the invention or containing or treated with a cell lysate, conditioned medium, or extracellular matrix thereof. The PPDCs may be differentiation-induced or undifferentiated. The matrix may contain or be treated with one or more bioactive factors including anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine.

Also encompassed within the scope of the invention are PPDC-products, including extracellular matrices of PPDCs, cell lysates (e.g., soluble cell fractions) of PPDCs, and PPDC-conditioned medium.

In some embodiments the invention provides compositions of PPDCs and one or more bioactive factors, for example, but not limited to growth factors, chondrogenic or osteogenic differentiation inducing factors, anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine).

Pharmaceutical compositions of the postpartum-derived cells, extracellular matrix produced thereby, cell lysates thereof, and PPDC-conditioned medium are included within the scope of the invention. The pharmaceutical compositions preferably include a pharmaceutically acceptable carrier or excipient. The pharmaceutical compositions are preferably for treating bone or cartilage conditions as defined herein.

The invention further provides in some aspects methods of regenerating bone or cartilage tissue in a patient in need thereof by administering cells, matrices, or PPDC-products of the invention into a patient are provided.

Further provided by the invention are methods for treating a condition such as a bone or cartilage condition in a patient by administering one or more postpartum-derived cells, PPDC populations, matrices, cell lysates, a combination of cell lysate and extracellular matrix, conditioned medium, or compositions of the invention. The PPDCs, whether differentiated or undifferentiated, or a combination thereof, extracellular matrix produced thereby, cell lysates thereof, a combination of cell lysate and extracellular matrix, matrices (e.g., scaffolds), conditioned medium, and compositions of the invention may be used in the treatment of bone or cartilage tissue conditions, for example, but not limited to congenital defects, bone fractures, meniscal injuries or defects, bone/spinal deformation, osteosarcoma, myeloma, bone dysplasia and scoliosis, osteoporosis, periodontal disease, dental bone loss, osteomalacia, rickets, fibrous osteitis, renal bone dystrophy, spinal fusion, spinal disc reconstruction or removal, Paget's disease of bone, meniscal injuries, rheumatoid arthritis, osteoarthritis, or a traumatic or surgical injury to cartilage or bone.

Also provided by the invention are kits comprising the postpartum-derived cells, PPDC-conditioned medium, lysate, and/or extracellular matrices of the invention. The kits of the invention may further contain at least one component of a matrix, a second cell type, a hydrating agent, a ell culture substrate, a differentiation-inducing agent, cell culture media, and instructions, for example, for culture of the cells or administration of the cells and/or cell products.

In some embodiments, the invention provides methods for identifying compounds that modulate chondrogenesis or osteogenesis of a postpartum-derived cell comprising contacting a cell of the invention with said compound and monitoring the cell for a marker of chondrogenesis or osteogenesis. Also provided are methods for identifying compound toxic to a postpartum-derived cell of the invention by contacting said cell with said compound and monitoring survival of said cell.

Other features and advantages of the invention will be apparent from the detailed description and examples that follow.

DETAILED DESCRIPTION OF ILLUSTRATIVE EMBODIMENTS

Definitions

Various terms used throughout the specification and claims are defined as set forth below.

Stem cells are undifferentiated cells defined by their ability at the single cell level to both self-renew and differentiate to produce progeny cells, including self-renewing progenitors, non-renewing progenitors and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent—able to give rise to all embryonic and extraembryonic cell types; (2) pluripotent—able to give rise to all embryonic cell types; (3) multipotent—able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood); (4) oligopotent—able to give rise to a more restricted subset of cell lineages than multipotent stem cells; and (5) unipotent—able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself and, under normal circumstances, differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated or differentiation-induced cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In a broad sense, a progenitor cell is a cell that has the capacity to create progeny that are more differentiated than itself and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoetic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, cell that give rise to the lining of the intestine, and cells that give rise to pancreogenic and splanchogenic cells.

The cells of the invention are referred to herein as postpartum-derived cells (PPDCs). Subsets of the cells of the present invention are referred to as placenta-derived cells (PDCs) or umbilical cord-derived cells (UDCs). PPDCs of the invention encompass undifferentiated and differentiation-induced cells. In addition, the cells may be described as being stem or progenitor cells, the latter term being used in the broad sense. The term derived is used to indicate that the cells have been obtained from their biological source and grown or otherwise manipulated in vitro (e.g., cultured in a growth medium to expand the population and/or to produce a cell line). The in vitro manipulations of postpartum-derived cells and the unique features of the postpartum-derived cells of the present invention are described in detail below.

Various terms are used to describe cells in culture. Cell culture refers generally to cells taken from a living organism and grown under controlled condition ("in culture"). A primary cell culture is a culture of cells, tissues or organs taken directly from organisms and before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

A conditioned medium is a medium in which a specific cell or population of cells has been cultured, and then removed. While the cells are cultured in the medium, they secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a trophic factor is defined as a substance that promotes survival, growth, proliferation, maturation, differentiation, and/or maintenance of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term Growth medium refers to a culture medium sufficient for expansion of postpartum-derived cells. The culture medium of Growth medium preferably contains Dulbecco's Modified Essential Media (DMEM). More preferably, Growth medium contains glucose. Growth medium preferably contains DMEM-low glucose (DMEM-LG) (Invitrogen, Carlsbad, Calif.). Growth medium preferably contains about 15% (v/v) serum (e.g., fetal bovine serum, defined bovine serum). Growth medium preferably contains at least one antibiotic agent and/or antimycotic agent (e.g., penicillin, streptomycin, amphotericin B, gentamicin, nystatin; preferably, 50 units/milliliter penicillin G sodium and 50 micrograms/milliliter streptomycin sulfate). Growth medium preferably contains 2-mercaptoethanol (Sigma, St. Louis Mo.). Most preferably, Growth medium contains DMEM-low glucose, serum, 2-mercaptoethanol, and an antibiotic agent.

As used herein, standard growth conditions refers to standard atmospheric conditions comprising about 5% $CO_2$, a temperature of about 35-39° C., more preferably 37° C., and a relative humidity of about 100%.

The term isolated refers to a cell, cellular component, or a molecule that has been removed from its native environment.

The term about refers to an approximation of a stated value within a range of ±10%.

Bone condition (or injury or disease) is an inclusive term encompassing acute and chronic and metabolic and non-metabolic conditions, disorders or diseases of bone. The term encompasses conditions caused by disease or trauma or failure of the tissue to develop normally. Examples of bone conditions include but are not limited to congenital bone defects, bone fractures, meniscal injuries or defects, bone/spinal deformation, osteosarcoma, myeloma, bone dysplasia and scoliosis, osteoporosis, periodontal disease, dental bone loss, osteomalacia, rickets, fibrous osteitis, renal bone dystrophy, spinal fusion, spinal disc reconstruction or removal, and Paget's disease of bone.

Cartilage condition (or injury or disease) is an inclusive term encompassing acute and chronic conditions, disorders, or diseases of cartilage. The term encompasses conditions including but not limited to congenital defects, meniscal injuries, rheumatoid arthritis, osteoarthritis, or a traumatic or surgical injury to cartilage.

The term treating (or treatment of) a bone or cartilage condition refers to ameliorating the effects of, or delaying, halting or reversing the progress of, or delaying or preventing the onset of, a bone or cartilage condition as defined herein.

The term effective amount refers to a concentration of a reagent or pharmaceutical composition, such as a growth factor, differentiation agent, trophic factor, cell population or other agent, that is effective for producing an intended result, including cell growth and/or differentiation in vitro or in vivo, or treatment of a bone or cartilage condition as described herein. With respect to growth factors, an effective amount may range from about 1 nanogram/milliliter to about 1 microgram/milliliter. With respect to PPDCs as administered to a patient in vivo, an effective amount may range from as few as several hundred or fewer to as many as several million or more. In specific embodiments, an effective amount may range from $10^3$-$10^{11}$. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or pharmaceutical composition to achieve its intended result.

The term patient or subject refers to animals, including mammals, preferably humans, who are treated with the pharmaceutical compositions or in accordance with the methods described herein.

The term matrix as used herein refers to a support for the PPDCs of the invention, for example, a scaffold (e.g., VICRYL, PCL/PGA, or RAD16) or supporting medium (e.g., hydrogel, extracellular membrane protein (e.g., MATRIGEL (BD Discovery Labware, Bedford, Mass.)).

The term pharmaceutically acceptable carrier (or medium), which may be used interchangeably with the term biologically compatible carrier or medium, refers to reagents, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds). As used herein, the term biodegradable describes the ability of a material to be broken down (e.g., degraded, eroded, dissolved) in vivo. The term includes degradation in vivo with or without elimination (e.g., by resorption) from the body. The semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or by breakdown and elimination through natural pathways.

Several terms are used herein with respect to cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

The following abbreviations are used herein:
ANG2 (or Ang2) for angiopoietin 2;
APC for antigen-presenting cells;
BDNF for brain-derived neurotrophic factor;
bFGF for basic fibroblast growth factor;
bid (BID) for "bis in die" (twice per day);
BSP for bone sialoprotein;
CK18 for cytokeratin 18;
CXC ligand 3 for chemokine receptor ligand 3;
DAP1 for 4'-6-Diamidino-2-phenylindole-2HCl;
DMEM for Dulbecco's Minimal Essential Medium;
DMEM:lg (or DMEM:Lg, DMEM:LG) for DMEM with low glucose;
EDTA for ethylene diamine tetraacetic acid;
EGF (or E) for epidermal growth factor;
EPO for erythropoietin;
FACS for fluorescent activated cell sorting;
FBS for fetal bovine serum;
FGF (or F) for fibroblast growth factor;
GCP-2 for granulocyte chemotactic protein-2;
GDF-5 for growth and differentiation factor 5;
GFAP for glial fibrillary acidic protein;
HB-EGF for heparin-binding epidermal growth factor;
HCAEC for Human coronary artery endothelial cells;
HGF for hepatocyte growth factor;
hMSC for Human mesenchymal stem cells;
HNF-1alpha for hepatocyte-specific transcription factor;
HUVEC for Human umbilical vein endothelial cells;
I309 for a chemokine and the ligand for the CCR8 receptor and is responsible for chemoattraction of TH2 type T-cells;
IGF for insulin-like growth factor;
IL-6 for interleukin-6;
IL-8 for interleukin 8;
K19 for keratin 19;
K8 for keratin 8;
KGF for keratinocyte growth factor;
MCP-1 for monocyte chemotactic protein 1;
MDC for macrophage-derived chemokine;
MIP1alpha for macrophage inflammatory protein 1alpha;
MIP1 beta for macrophage inflammatory protein 1 beta;
MMP for matrix metalloprotease (MMP);
MSC for mesenchymal stem cells;
NHDF for Normal Human Dermal Fibroblasts;
NPE for Neural Progenitor Expansion media;
OxLDLR for oxidized low density lipoprotein receptor;
PBMC for peripheral blood mononuclear cell;
PBS for phosphate buffered saline;
PDC for placenta-derived cell;
PDGFbb for platelet derived growth factor;
PDGFr-alpha for platelet derived growth factor receptor alpha;
PD-L2 for programmed-death ligand 2;
PE for phycoerythrin;
PO for "per os" (by mouth);
PPDC for postpartum-derived cell;
Rantes (or RANTES) for regulated on activation, normal T cell expressed and secreted;
rb for rabbit;
rh for recombinant human;
SC for subcutaneously;
SCID for severe combined immunodeficiency;
SDF-1alpha for stromal-derived factor 1alpha;
SHH for sonic hedgehog;
SMA for smooth muscle actin;

SOP for standard operating procedure;
TARC for thymus and activation-regulated chemokine;
TCP for tissue culture plastic;
TGFbeta2 for transforming growth factor beta2;
TGFbeta-3 for transforming growth factor beta-3;
TIMP1 for tissue inhibitor of matrix metalloproteinase 1;
TPO for thrombopoietin;
TuJ1 for BIII Tubulin;
UDC for umbilical cord-derived cell;
VEGF for vascular endothelial growth factor;
vWF for von Willebrand factor; and
alphaFP for alpha-fetoprotein.

Description

Various patents and other publications are cited herein and throughout the specification, each of which is incorporated by reference herein in its entirety.

In one aspect, the invention provides postpartum-derived cells (PPDCs) derived from postpartum tissue substantially free of blood. The PPDCs may be derived from placenta of a mammal including but not limited to human. The cells are capable of self-renewal and expansion in culture. The postpartum-derived cells have the potential to differentiate into cells of other phenotypes. The invention provides, in one of its several aspects cells that are derived from umbilical cord, as opposed to umbilical cord blood. The invention also provides, in one of its several aspects, cells that are derived from placental tissue.

The cells have been characterized as to several of their cellular, genetic, immunological, and biochemical properties. For example, the cells have been characterized by their growth by their cell surface markers, by their gene expression, by their ability to produce certain biochemical trophic factors, and by their immunological properties.

Derivation and Expansion of Postpartum-Derived Cells (PPDCs)

According to the methods described herein, a mammalian placenta and umbilical cord are recovered upon or shortly after termination of either a full-term or pre-term pregnancy, for example, after expulsion after birth. Postpartum tissue can be obtained from any completed pregnancy, full-term or less than full-term, whether delivered vaginally, or through other means, for example, Cessarian section. The postpartum tissue may be transported from the birth site to a laboratory in a sterile container such as a flask, beaker, culture dish, or bag. The container may have a solution or medium, including but not limited to a salt solution, such as, for example, Dulbecco's Modified Eagle's Medium (DMEM) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4-10° C. prior to extraction of PPDCs. It is even more preferable that the tissue not be frozen prior to extraction of PPDCs.

Isolation of PPDCs preferably occurs in an aseptic environment. Blood and debris are preferably removed from the postpartum tissue prior to isolation of PPDCs. For example, the postpartum tissue may be washed with buffer solution, such as but not limited to phosphate buffered saline. The wash buffer also may comprise one or more antimycotic and/or antibiotic agents, such as but not limited to penicillin, streptomycin, amphotericin B, gentamicin, and nystatin.

In some aspects of the invention, the different cell types present in postpartum tissue are fractionated into subpopulations from which the PPDCs can be isolated. This may be accomplished using techniques for cell separation including, but not limited to, enzymatic treatment to dissociate postpartum tissue into its component cells, followed by cloning and selection of specific cell types, for example but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and flow cytometry, for example, fluorescence activated cell sorting (FACS).

In a preferred embodiment, postpartum tissue comprising a whole placenta or a fragment or section thereof is disaggregated by mechanical force (mincing or shear forces), enzymatic digestion with single or combinatorial proteolytic enzymes, such as a matrix metalloprotease and/or neutral protease, for example, collagenase, trypsin, dispase, LIBERASE (Boehringer Mannheim Corp., Indianapolis, Ind.), hyaluronidase, and/or pepsin, or a combination of mechanical and enzymatic methods. For example, the cellular component of the postpartum tissue may be disaggregated by methods using collagenase-mediated dissociation. Enzymatic digestion methods preferably employ a combination of enzymes, such as a combination of a matrix metalloprotease and a neutral protease. The matrix metalloprotease is preferably a collagenase. The neutral protease is preferably thermolysin or dispase, and most preferably is dispase. More preferably, enzymatic digestion of postpartum tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Collagenase may be type 1, 2, 3, or 4. Other enzymes known in the art for cell isolation include papain, deoxyribonucleases, serine proteases, such as trypsin, chymotrypsin, or elastase, that may be used either on their own or in combination with other enzymes such as matrix metalloproteases, mucolytic enzymes, and neutral proteases. Serine proteases are preferably used consecutively following use of other enzymes. The temperature and period of time tissues or cells are in contact with serine proteases is particularly important. Serine proteases may be inhibited by alpha 2 microglobulin in serum and therefore the medium used for digestion is usually serum-free. EDTA and DNAse are commonly used in enzyme digestion procedures to increase the efficiency of cell recovery. The degree of dilution of the digestion may also greatly affect the cell yield as cells may be trapped within the viscous digest. The LIBERASE (Boehringer Mannheim Corp., Indianapolis, Ind.) Blendzyme (Roche) series of enzyme combinations are very useful and may be used in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In more preferred embodiments, the tissue is incubated at 37° C. during the enzyme treatment of the disintegration step.

Postpartum tissue comprising the umbilical cord and placenta may be used without separation. Alternatively, the umbilical cord may be separated from the placenta by any means known in the art. In some embodiments of the invention, postpartum tissue is separated into two or more sections, such as umbilical cord and placenta. In some embodiments of the invention, placental tissue is separated into two or more sections, each section consisting predominantly of either neonatal, neonatal and maternal, or maternal aspect. The separated sections then are dissociated by mechanical and/or enzymatic dissociation according to the methods described herein. Cells of neonatal or maternal lineage may be identified by any means known in the art, for example, by karyotype analysis or in situ hybridization for the Y-chromosome. Karyotype analysis also may be used to identify cells of normal karyotype.

Isolated cells or postpartum tissue from which PPDCs grow out may be used to initiate, or seed, cell cultures. Cells are transferred to sterile tissue culture vessels either uncoated or coated with extracellular matrix or ligands such as laminin, collagen, gelatin, fibronectin, ornithine, vitronectin, and extracellular membrane protein (e.g., MATRIGEL (BD Discovery Labware, Bedford, Mass.)). PPDCs are cultured in any culture medium capable of sustaining growth of the cells such as, but not limited to, DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), DMEM/F12, RPMI 1640, advanced DMEM (Gibco), DMEM/MCDB201 (Sigma), and CELL-GRO FREE. The culture medium may be supplemented with one or more components including, for example, serum (e.g., fetal bovine serum (FBS), preferably about 2-15% (v/v); equine serum (ES); human serum (HS)); beta-mercaptoethanol (BME), preferably about 0.001% (v/v); one or more growth factors, for example, platelet-derived growth factor (PDGF), insulin-like growth factor-1 (IGF-1), leukemia inhibitory factor (LIF), epidermal growth factor (EGF), basic fibroblast growth factor (bFGF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination. The culture medium preferably comprises Growth medium (DMEM-low glucose, serum, BME, an antimycotic agent, and an antibiotic agent).

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25 to about 40° C., more preferably about 35° C. to about 39° C., and more preferably are cultured at 37° C. The cells are preferably cultured in an incubator. The medium in the culture vessel can be static or agitated, for example, using a bioreactor. PPDCs preferably are grown under low oxidative stress (e.g., with addition of glutathione, ascorbic acid, catalase, tocopherol, N-acetylcysteine). "Low oxidative stress", as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

The culture medium is changed as necessary, for example, by carefully aspirating the medium from the dish, for example, with a pipette, and replenishing with fresh medium. Incubation is continued until a sufficient number or density of cells accumulate in the dish. The original explanted tissue sections may be removed and the remaining cells trypsinized using standard techniques or using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be PPDCs.

After culturing the cells or tissue fragments for a sufficient period of time, PPDCs will have grown out, either as a result of migration from the postpartum tissue or cell division, or both. In some embodiments of the invention, PPDCs are passaged, or removed to a separate culture vessel containing fresh medium of the same or a different type as that used initially, where the population of cells can be mitotically expanded. PPDCs are preferably passaged up to about 100% confluence, more preferably about 70 to about 85% confluence. The lower limit of confluence for passage is understood by one skilled in the art. The placenta-derived cells of the invention may be utilized from the first subculture (passage 0) to senescence. The preferable number of passages is that which yields a cell number sufficient for a given application. In certain embodiments, the cells are passaged 2 to 25 times, preferably 4 to 20 times, more preferably 8 to 15 times, more preferably 10 or 11 times, and most preferably 11 times. Cloning and/or subcloning may be performed to confirm that a clonal population of cells has been isolated.

Cells of the invention may be cryopreserved and/or stored prior to use.

Characterization of PPDCs

PPDCs may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes including but not limited to vimentin, desmin, alpha-smooth muscle actin, cytokeratin 18, von Willebrand factor, CD34, GROalpha, GCP-2, oxidized low density lipoprotein receptor 1, and NOGO-A), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PPDC-conditioned medium, for example, by Enzyme Linked ImmunoSorbent Assay (ELISA)), antibody analysis (e.g., ELISA; antibody staining for cell surface markers including but not limited to CD10, CD13, CD31, CD34, CD44, CD45, CD73, CD80, CD86, CD90, CD117, CD141, CD178, platelet-derived growth factor receptor alpha (PDGFr-alpha), HLA class I antigens (HLA-A, HLA-B, HLA-C), HLA class II antigens (HLA-DP, HLA-DQ, HLA-DR), B7-H2, and PD-L2), mixed lymphocyte reaction (e.g., as measure of stimulation of allogeneic PBMCs), and/or other methods known in the art.

PPDCs can undergo at least 40 population doublings in culture. Population doubling may be calculated as [ln (cell final/cell initial)/ln 2]. Doubling time may be calculated as (time in culture (h)/population doubling).

Undifferentiated PPDCs preferably produce of at least one of NOGO-A, GCP-2, tissue factor, vimentin, and alpha-smooth muscle actin; more preferred are cells which produce each of GCP-2, tissue factor, vimentin, and alpha-smooth muscle actin. In some embodiments, two, three, four, or five of these factors are produced by the PPDCs.

In some embodiments, PPDCs lack production of at least one of NOGO-A, GRO-alpha, or oxidized low density lipoprotein receptor, as detected by flow cytometry. In some embodiments, PPDCs lack production of at least two or three of these factors.

PPDCs may comprise at least one cell surface marker of CD10, CD13, CD44, CD73, CD90, PDGFr-alpha, PD-L2 and HLA-A,B,C. PPDCs preferably produce each of these surface markers. PPDCs may be characterized in their lack of production of at least one of CD31, CD34, CD45, CD80, CD86, CD117, CD141, CD178, B7-H2, HLA-G, and HLA-DR, DP, DQ, as detected by flow cytometry. PPDCs preferably lack production of each of these surface markers.

In some embodiments, PPDCs exhibit expression, which relative to a human cell that is a fibroblast, a mesenchymal stem cell, or an iliac crest bone marrow cell, is increased for at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3; or at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113. Preferred PPDCs express, relative to a human cell that is a fibroblast, a mesenchymal stem cell, or an iliac crest bone marrow cell, increased levels of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3; or increased levels of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113. In PPDCs wherein expression, relative to a human cell that is a fibroblast, a mesenchymal stem cell, or an iliac crest bone marrow cell, is increased for at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3, increased relative levels of at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113 are preferably not present. In PPDCs wherein expression, relative to a human cell that is a fibroblast, a mesenchymal stem cell, or an iliac crest bone marrow cell, is increased for at least one of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113, increased relative levels of at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3 are preferably not present.

PPDCs may have expression, which relative to a human cell that is a fibroblast, a mesenchymal stem cell, or an iliac crest bone marrow cell, is reduced for at least one of: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; and insulin-like growth factor binding protein 2, 36 kDa; the skilled artisan will appreciate that the expression of a wide variety of genes is conveniently characterized on a gene array, for example on a Affymetrix GENECHIP.

PPDCs may secrete a variety of biochemically active factors, such as growth factors, chemokines, cytokines and the like. Preferred cells secrete at least one of MCP-1, IL-6, IL-8, GCP-2, HGF, KGF, FGF, HB-EGF, BDNF, TPO, MIP1a, RANTES, and TIMP1. PPDCs may be characterized in their lack of secretion of at least one of TGF-beta2, ANG2, PDGFbb, MIP1b, 1309, MDC, and VEGF, as detected by ELISA. These and other characteristics are available to identify and characterize the cells, and distinguish the cells of the invention from others known in the art.

In preferred embodiments, the cell comprises two or more of the foregoing characteristics. More preferred are those cells comprising, three, four, or five or more of the characteristics. Still more preferred are those postpartum-derived cells comprising six, seven, or eight or more of the characteristics. Still more preferred presently are those cells comprising all nine of the claimed characteristics.

Also presently preferred are cells that produce at least two of GCP-2, NOGO-A, tissue factor, vimentin, and alpha-smooth muscle actin. More preferred are those cells producing three, four, or five of these proteins.

The skilled artisan will appreciate that cell markers are subject to vary somewhat under vastly different growth conditions, and that generally herein described are characterizations in Growth Medium, or variations thereof. Postpartum-derived cells that produce of at least one, two, three, or four of CD10, CD13, CD44, CD73, CD90, PDGFr-alpha, PD-L2 and HLA-A,B,C are preferred. More preferred are those cells producing five, six, or seven of these cell surface markers. Still more preferred are postpartum-derived cells that can produce eight, nine, or ten of the foregoing cell surface marker proteins.

PPDCs that lack of production of at least one, two, three, or four of the proteins CD31, CD34, CD45, CD80, CD86, CD117, CD141, CD178, B7-H2, HLA-G, and HLA-DR,DP, DQ, as detected by flow cytometry are preferred. PPDCs lacking production of at least five, six, seven, or eight or more of these markers are preferred. More preferred are cells which lack production of at least nine or ten of the cell surface markers. Most highly preferred are those cells lacking production of eleven, twelve, or thirteen of the foregoing identifying proteins.

Presently preferred cells produce each of CD10, CD13, CD44, CD73, CD90, PDGFr-alpha, and HLA-A,B,C, and do not produce any of CD31, CD34, CD45, CD117, CD141, or HLA-DR,DP,DQ, as detected by flow cytometry.

It is preferred that postpartum-derived cells exhibit expression, which relative to a human cell that is a fibroblast, a mesenchymal stem cell, or an iliac crest bone marrow cell, is increased for at least one of at least one, two, or three of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3; or at least one, two, or three of C-type lectin superfamily member A2, Wilms tumor 1, aldehyde dehydrogenase 1 family member A2, renin, oxidized low density lipoprotein receptor 1, protein kinase C zeta, clone IMAGE:4179671, hypothetical protein DKFZp564F013, downregulated in ovarian cancer 1, and clone DKFZp547K1113. More preferred are those cells which exhibit elevated relative expression of four or five, and still more preferred are cell capable of increased relative expression of six, seven, or eight of the foregoing genes of the respective gene sets. Most preferably, the cells exhibit expression, which relative to a human cell that is a fibroblast, a mesenchymal stem cell, or an iliac crest bone marrow cell, is increased for a combination of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; tumor necrosis factor, alpha-induced protein 3 or a combination of C-type lectin superfamily member A2, Wilms tumor 1, aldehyde dehydrogenase 1 family member A2, renin, oxidized low density lipoprotein receptor 1, protein kinase C zeta, clone IMAGE: 4179671, hypothetical protein DKFZp564F013, downregulated in ovarian cancer 1, and clone DKFZp547K1113.

For some embodiments, preferred are cells, which relative to a human cell that is a fibroblast, a mesenchymal stem cell, or an iliac crest bone marrow cell, have reduced expression for at least one of the genes corresponding to: short stature homeobox 2; heat shock 27 kDa protein 2; chemokine (C-X-C motif) ligand 12 (stromal cell-derived factor 1); elastin; cDNA DKFZp586M2022 (from clone DKFZp586M2022); mesenchyme homeobox 2; sine oculis homeobox homolog 1; crystallin, alpha B; dishevelled associated activator of morphogenesis 2; DKFZP586B2420 protein; similar to neuralin 1; tetranectin; src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7; hypothetical gene BC008967; collagen, type VIII, alpha 1; tenascin C; iroquois homeobox protein 5; hephaestin; integrin, beta 8; synaptic vesicle glycoprotein 2; cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2; KIAA1034 protein; early growth response 3; distal-less homeobox 5; hypothetical protein F1120373; aldo-keto reductase family 1, member C3 (3-alpha hydroxysteroid dehydrogenase, type II); biglycan; fibronectin 1; proenkephalin; integrin, beta-like 1 (with EGF-like repeat domains); cDNA clone EUROIMAGE 1968422; EphA3; KIAA0367 protein; natriuretic peptide receptor C/guanylate cyclase C (atrionatriuretic peptide receptor C); hypothetical protein FLJ14054; cDNA DKFZp564B222 (from clone DKFZp564B222); vesicle-associated membrane protein 5; EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; and insulin-like growth factor binding protein 2, 36 kDa. More preferred are cells that have, relative to human fibroblasts, mesenchymal stem cells, or iliac crest bone marrow cells, reduced expression of at least 5, 10, 15 or 20 genes corresponding to those listed above. Presently more preferred are cell with reduced expression of at least 25, 30, or 35 of the genes corresponding to the listed sequences. Also more preferred are those postpartum-derived cells having expression that is reduced, relative to that of a human fibroblast, a mesenchymal stem cell, or an iliac crest bone marrow cell, of genes corresponding to 35 or more, 40 or more, or even all of the sequences listed.

Secretion of certain growth factors and other cellular proteins can make cells of the invention particularly useful. Preferred postpartum-derived cells secrete at least one, two, three or four of MCP-1, IL-6, IL-8, GCP-2, HGF, KGF, FGF, HB-EGF, BDNF, TPO, MIP1a, RANTES, and TIMP1. Cells which secrete five, six, seven or eight of the listed proteins are also preferred. Cells which can secrete at least nine, ten, eleven or more of the factors are more preferred, as are cells which can secrete twelve or more, or even all thirteen of the proteins in the foregoing list.

While secretion of such factors is useful, PPDCs can also be characterized by their lack of secretion of factors into the medium. Postpartum-derived cells that lack secretion of at least one, two, three or four of TGF-beta2, ANG2, PDGFbb, MIP1b, 1309, MDC, and VEGF, as detected by ELISA, are presently preferred for use. Cells that are characterized in their lack secretion of five or six of the foregoing proteins are more preferred. Cells which lack secretion of all seven of the factors listed above are also preferred.

Examples of placenta-derived cells of the invention were deposited with the American Type Culture Collection (ATCC, Manassas, Va.) and assigned ATCC Accession Numbers as follows: (1) strain designation PLA 071003 (P8)

was deposited Jun. 15, 2004 and assigned Accession No. PTA-6074; (2) strain designation PLA 071003 (P11) was deposited Jun. 15, 2004 and assigned Accession No. PTA-6075; and (3) strain designation PLA 071003 (P16) was deposited Jun. 16, 2004 and assigned Accession No. PTA-6079.

Examples of umbilical cord-derived cells of the invention were deposited with the American Type Culture Collection (ATCC, Manassas, Va.) on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

PPDCs can be isolated. The invention also provides compositions of PPDCs, including populations of PPDCs. In some embodiments, the cell population is heterogeneous. A heterogeneous cell population of the invention may comprise at least about 5%, 10%, 20%, 30%, 40%, 50%, 60%, 70%, 80%, 90%, or 95% PPDCs of the invention. In some embodiments, the heterogeneous cell populations of the invention may further comprise bone marrow cells, stem cells, chondroblasts, chondrocytes, and/or progenitor cells. In some embodiments, the heterogeneous cell populations of the invention may further comprise bone marrow cells, stem cells, osteoblasts, osteocytes, osteoclasts, bone lining cells, and/or progenitor cells. In some embodiments, the population is substantially homogeneous, i.e., comprises substantially only PPDCs (preferably at least about 96%, 97%, 98%, 99% or more PPDCs). The homogeneous cell population of the invention may comprise umbilical cord- or placenta-derived cells. Homogeneous populations of umbilical cord-derived cells may be free of cells of maternal lineage. Homogeneous populations of placenta-derived cells may be of neonatal or maternal lineage. Homogeneity of a cell population may be achieved by any method known in the art, for example, by cell sorting (e.g., flow cytometry), bead separation, or by clonal expansion.

Methods of the invention further include methods for producing a population of postpartum-derived cells by expanding a cell of the invention in culture. The postpartum-derived cells of the invention preferably expand in the presence of from about 5% to about 20% oxygen. The postpartum-derived cells of the invention preferably are expanded in culture medium such as but not limited to Dulbecco's modified Eagle's medium (DMEM), mesenchymal stem cell growth medium, advanced DMEM (Gibco), DMEM/MCDB201 (Sigma), RPMI1640, CELL-GRO FREE, advanced DMEM (Gibco), DMEM/MCDB201 (Sigma), Ham's F10 medium, Ham's F12 medium, DMEM/F12, Iscove's modified Dulbecco's medium, or Eagle's basal medium. The culture medium preferably contains low or high glucose, about 2%-15% (v/v) serum, betamercaptoethanol, and an antibiotic agent. The culture medium may contain at least one of fibroblast growth factor, platelet-derived growth factor, vascular endothelial growth factor, and epidermal growth factor. The cells of the invention may be grown on an uncoated or coated surface. Surfaces for growth of the cells may be coated for example with gelatin, collagen (e.g., native or denatured), fibronectin, laminin, ornithine, vitronectin, or extracellular membrane protein (e.g., MATRIGEL). In some embodiments, a population of postpartum-derived cells is mixed with another population of cells.

Culture of PPDCs in a Chondrogenic Medium

PPDCs may be induced to differentiate into a chondrogenic lineage by subjecting them to differentiation-inducing cell culture conditions. PPDCs may be cultured in a chondrogenic medium comprising specific exogenous chondrogenic growth factors (e.g., in culture), such as, for example, one or more of GDF-5 or transforming growth factor beta3 (TGF-beta3), with or without ascorbate.

Preferred chondrogenic medium is supplemented with an antibiotic agent, amino acids including proline and glutamine, sodium pyruvate, dexamethasone, ascorbic acid, and insulin/tranferrin/selenium. Chondrogenic medium is preferably supplemented with sodium hydroxide and/or collagen. Most preferably, chondrogenic culture medium is supplemented with collagen. The cells may be cultured at high or low density. Cells are preferably cultured in the absence of serum.

Culture of PPDCs in an Osteogenic Medium

PPDCs may be induced to differentiate into an osteogenic lineage by subjecting them to differentiation-inducing cell culture conditions. In some embodiments, PPDCs are cultured in osteogenic medium such as, but not limited to, media (e.g., DMEM-low glucose) containing about $10^{-7}$ molar and about $10^{-9}$ molar dexamethasone in combination with about 10 micromolar to about 50 micromolar ascorbate phosphate salt (e.g., ascorbate-2-phosphate) and between about 10 nanomolar and about 10 millimolar beta-glycerophosphate. The medium preferably includes serum (e.g., bovine serum, horse serum). Osteogenic medium also may comprise one or more antibiotic/antimycotic agents. The osteogenic medium is preferably supplemented with transforming growth factor-beta (e.g., TGF-beta1) and/or bone morphogenic protein (e.g., BMP-2, BMP-4, or a combination thereof; most preferably BMP-4)

Assessment of Differentiation

PPDCs may be induced to differentiate to an ectodermal, endodermal, or mesodermal lineage. Methods to characterize differentiated cells that develop from the PPDCs of the invention, include, but are not limited to, histological, morphological, biochemical and immunohistochemical methods, or using cell surface markers, or genetically or molecularly, or by identifying factors secreted by the differentiated cell, and by the inductive qualities of the differentiated PPDCs.

Chondrogenic differentiation may be assessed, for example, by Safranin-O staining for glycosaminoglycan expression by the cells or hematoxylin/eosin staining or by detection of a chondrogenic lienage marker (e.g., sulfated glycosaminoglycans and proteoglycans, keratin, chondroitin, Type II collagen) in the culture or more preferably in the cells themselves.

PPDCs may be analyzed for an osteogenic phenotype by any method known in the art, e.g., von Kossa staining or by detection of osteogenic markers such as osteocalcin, bone sialoprotein, alkaline phosphatase, osteonectin, osteopontin, type I collagen, bone morphogenic proteins, and/or core binding factor al in the culture or more preferably in the cells themselves.

Methods of Using PPDCs or Components or Products Thereof.

Genetic Engineering of PPDCs

The cells of the invention can be engineered using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with DNA controlled by or in operative association with, one or more appropriate expression control elements such as promoter or enhancer sequences, transcription terminators, polyadenylation sites, among others, and a selectable marker.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines.

This method can be advantageously used to engineer cell lines which express the gene product.

Any promoter may be used to drive the expression of the inserted gene. For example, viral promoters include, but are not limited to, the CMV promoter/enhancer, SV 40, papillomavirus, Epstein-Barr virus or elastin gene promoter. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary.

Inducible promoters include, but are not limited to, those associated with metallothionein and heat shock proteins.

The cells of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a chondrocyte or osteocyte can be reduced or knocked out using a number of techniques including, for example, inhibition of expression by inactivating the gene completely (commonly termed "knockout") using the homologous recombination technique. Usually, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.* 88:3084).

Antisense, small interfering RNA, DNAzymes and ribozyme molecules which inhibit expression of the target gene can also be used in accordance with the invention to reduce the level of target gene activity. For example, antisense RNA molecules which inhibit the expression of major histocompatibility gene complexes (HLA) have been shown to be most versatile with respect to immune responses. Still further, triple helix molecules can be utilized in reducing the level of target gene activity.

These techniques are described in detail by L. G. Davis et al. (eds), 1994, BASIC METHODS IN MOLECULAR BIOLOGY, 2nd ed., Appleton & Lange, Norwalk, Conn., which is incorporated herein by reference.

IL-1 is a potent stimulator of cartilage resorption and of the production of inflammatory mediators by chondrocytes (Campbell et al., 1991, *J. Immun.* 147: 1238). Using any of the foregoing techniques, the expression of IL-1 can be knocked out or knocked down in the cells of the invention to reduce the risk of resorption of implanted cartilage or the production of inflammatory mediators by the cells of the invention. Likewise, the expression of MHC class II molecules can be knocked out or knocked down in order to reduce the risk of rejection of the implanted tissue.

Once the cells of the invention have been genetically engineered, they may be directly implanted into the patient to allow for the treatment of a bone or cartilage condition, for example, rheumatoid or joint disease, or to produce an anti-inflammatory gene product such as, for example, peptides or polypeptides corresponding to the idiotype of neutralizing antibodies for GM-CSF, TNF, IL-1, IL-2, or other inflammatory cytokines.

Alternatively, the genetically engineered cells may be used to produce new tissue in vitro, which is then implanted in the subject, as described herein.

Secretion of Trophic Factors

The secretion of growth factors by PPDCs may provide trophic support for a second cell type in vitro or in vivo. PPDCs may secrete, for example, at least one of monocyte chemotactic protein 1 (MCP-1), interleukin-6 (IL6), interleukin 8 (IL-8), GCP-2, hepatocyte growth factor (HGF), keratinocyte growth factor (KGF), fibroblast growth factor (FGF), heparin binding epidermal growth factor (HB-EGF), brain-derived neurotrophic factor (BDNF), thrombopoietin (TPO), macrophage inflammatory protein 1 alpha (MIP1a), RANTES, and tissue inhibitor of matrix metalloproteinase 1 (TIMP1), which can be augmented by a variety of techniques, including ex vivo cultivation of the cells in chemically defined medium.

In some aspects of the invention, a population of PPDCs supports the survival, proliferation, growth, maintenance, maturation, differentiation, or increased activity of cells including stem cells, such as embryonic stem cells, bone marrow cells, chondrocytes, chondroblasts, and mixtures thereof. In some aspects of the invention, a population of PPDCs supports cells including stem cells, such as embryonic stem cells, bone marrow cells, osteoblasts, osteocytes, osteoclasts, bone lining cells, and mixtures thereof. In some aspects of the invention, a population of PPDCs supports cells including stem cells, such as embryonic stem cells, bone marrow cells, chondrocytes, chondroblasts, osteoblasts, osteocytes, osteoclasts, bone lining cells, and mixtures thereof. In other embodiments, the population is substantially homogeneous, i.e., comprises substantially only PPDCs (preferably at least about 96%, 97%, 98%, 99% or more PPDCs).

PPDCs have the ability to support survival, growth, and differentiation of other cell types in co-culture. In some embodiments, PPDCs are co-cultured in vitro to provide trophic support to other cells, including but not limited to stem cells, osteocytes, osteoblasts, osteoclasts, bone lining cells, chondrocytes, chondroblasts, and/or bone marrow cells, or combinations thereof. For co-culture, it may be desirable for the PPDCs and the desired other cells to be co-cultured under conditions in which the two cell types are in contact. This can be achieved, for example, by seeding the cells as a heterogeneous population of cells in culture medium or onto a suitable culture substrate. Alternatively, the PPDCs can first be grown to confluence and employed as a substrate for the second desired cell type in culture. In this latter embodiment, the cells may further be physically separated, e.g., by a membrane or similar device, such that the other cell type may be removed and used separately following the co-culture period. In other embodiments, the desired other cells are cultured in contact with the conditioned medium, extracellular matrix, and/or cell lysate of the PPDCs. Use of PPDCs in co-culture to promote expansion and differentiation of other cell types may find applicability in research and in clinical/therapeutic areas. For instance, PPDC co-culture may be utilized to facilitate growth and differentiation of cells of a given phenotype in culture, for example, chondrocytes or osteocytes, for basic research purposes or for use in drug screening assays, for example. PPDC co-culture may also be utilized for ex vivo expansion of cells of an osteogenic or chondrogenic phenotype for later administration for therapeutic purposes. For example, cells may be harvested from an individual, expanded ex vivo in co-culture with PPDCs, then returned to that individual (autologous transfer) or another individual (syngeneic or allogeneic transfer). In these embodiments, it will be appreciated that, following ex vivo expansion, the mixed population of cells comprising the PPDCs could be administered to a patient in need of treatment, for example, of a bone or cartilage condition as described herein. Alternatively, in situations where autologous transfer is appropriate or desirable, the co-cultured cell populations may be physically separated in culture, enabling removal of the autologous cells for administration to the patient.

Conditioned Medium of PPDCs

Another embodiment of the invention features use of PPDCs for production of conditioned medium, either from undifferentiated PPDCs or from PPDCs incubated under conditions that stimulate differentiation into a chondrogenic or osteogenic lineage. Such conditioned media are contemplated for use in in vitro or ex vivo culture of cells, for example, stem or progenitor cells, including but not limited to bone marrow cells, osteoblasts, osteocytes, osteoclasts, bone lining cells, chondroblasts, and chondrocytes, or in vivo to support transplanted cells comprising homogeneous or heterogeneous populations of PPDCs and/or stem cells, osteocytes, osteoblasts, osteoclasts, bone lining cells, chondrocytes, chondroblasts, and bone marrow cells, for example.

Therapeutic Applications of PPDCs

PPDCs of the invention may be used to treat patients requiring the repair or replacement of cartilage or bone tissue resulting from disease or trauma or failure of the tissue to develop normally, or to provide a cosmetic function, such as to augment facial or other features of the body. Treatment may entail the use of the cells of the invention to produce new cartilage tissue or bone tissue. For example, the undifferentiated or chondrogenic differentiation-induced cells of the invention may be used to treat a cartilage condition, for example, rheumatoid arthritis or osteoarthritis or a traumatic or surgical injury to cartilage. As another example, the undifferentiated or osteogenic differentiation-induced cells of the invention may be used to treat bone conditions, including metabolic and non-metabolic bone diseases. Examples of bone conditions include meniscal tears, spinal fusion, spinal disc removal, spinal reconstruction, bone fractures, bone/spinal deformation, osteosarcoma, myeloma, bone dysplasia, scoliosis, osteoporosis, periodontal disease, dental bone loss, osteomalacia, rickets, fibrous osteitis, renal bone dystrophy, and Paget's disease of bone.

The cells of the invention may be administered alone or as admixtures with other cells. Cells that may be administered in conjunction with PPDCs include, but are not limited to, other multipotent or pluripotent cells or chondrocytes, chondroblasts, osteocytes, osteoblasts, osteoclasts, bone lining cells, stem cells, or bone marrow cells. The cells of different types may be admixed with the PPDCs immediately or shortly prior to administration, or they may be co-cultured together for a period of time prior to administration.

The PPDCs may be administered with other beneficial drugs or biological molecules (growth factors, trophic factors). When PPDCs are administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the cells may be co-administered with scar inhibitory factor as described in U.S. Pat. No. 5,827,735, incorporated herein by reference.

In one embodiment, PPDCs are administered as undifferentiated cells, i.e., as cultured in Growth Medium. Alternatively, PPDCs may be administered following exposure in culture to conditions that stimulate differentiation toward a desired phenotype, for example, a chondrogenic or osteogenic phenotype.

The cells of the invention may be surgically implanted, injected, delivered (e.g., by way of a catheter or syringe), or otherwise administered directly or indirectly to the site in need of repair or augmentation. The cells may be administered by way of a matrix (e.g., a three-dimensional scaffold). The cells may be administered with conventional pharmaceutically acceptable carriers. Routes of administration of the cells of the invention or compositions or components (e.g., ECM, cell lysate, conditioned medium) thereof include intramuscular, ophthalmic, parenteral (including intravenous), intraarterial, subcutaneous, oral, and nasal administration. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration.

When cells are administered in semi-solid or solid devices, surgical implantation into a precise location in the body is typically a suitable means of administration. Liquid or fluid pharmaceutical compositions, however, may be administered to a more general location (e.g., throughout a diffusely affected area, for example), from which they migrate to a particular location, e.g., by responding to chemical signals.

Other embodiments encompass methods of treatment by administering pharmaceutical compositions comprising PPDC cellular components (e.g., cell lysates or components thereof) or products (e.g., extracellular matrix, trophic and other biological factors produced naturally by PPDCs or through genetic modification, conditioned medium from PPDC culture). Again, these methods may further comprise administering other active agents, such as anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine), local anesthetics, and scar inhibitory factor as described in U.S. Pat. No. 5,827,735, incorporated herein by reference.

Dosage forms and regimes for administering PPDCs or any of the other pharmaceutical compositions described herein are developed in accordance with good medical practice, taking into account the condition of the individual patient, e.g., nature and extent of the condition being treated, age, sex, body weight and general medical condition, and other factors known to medical practitioners. Thus, the effective amount of a pharmaceutical composition to be administered to a patient is determined by these considerations as known in the art.

In some embodiments of the invention, it may not be necessary or desirable to immunosuppress a patient prior to initiation of cell therapy with PPDCs. In addition, PPDCs have been shown not to stimulate allogeneic PBMCs in a mixed lymphocyte reaction. Accordingly, transplantation with allogeneic, or even xenogeneic, PPDCs may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. PPDCs may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, PPDCs may be genetically modified to reduce their immunogenicity.

Survival of transplanted PPDCs in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the target tissue, and examining it visually or through a microscope. Alternatively, cells can be treated with stains that are specific for cells of a specific lineage. Transplanted cells can also be identified by prior incorporation of tracer dyes such as rhodamine- or fluorescein-labeled microspheres, fast blue, bisbenzamide, ferric microparticles, or genetically introduced reporter gene products, such as beta-galactosidase or beta-glucuronidase.

Functional integration of transplanted PPDCs into a subject can be assessed by examining restoration of the function that was damaged or diseased, for example, restoration of joint or bone function, or augmentation of function.

Compositions and Pharmaceutical Compositions

Compositions of PPDCs and related products (e.g., extracellular matrix, lysate, soluble cell fraction, conditioned medium), including for example pharmaceutical compositions, are included within the scope of the invention. Compositions of the invention may include one or more bioactive factors, for example but not limited to a growth factor, a differentiation-inducing factor, a cell survival factor such as caspase inhibitor, an anti-inflammatory agent such as p38 kinase inhibitor, or an angiogenic factor such as VEGF or bFGF. Some examples of bioactive factors include PDGFbb, EGF, bFGF, IGF-1, and LIF. In some embodiments, undifferentiated or differentiation-induced PDPCs are cultured in contact with the bioactive factor. In some embodiments, undifferentiated PPDCs remain undifferentiated upon contact with the bioactive factor. In other embodiments, the bioactive factor induces differentiation of the PPDCs.

Pharmaceutical compositions of the invention may comprise homogeneous or heterogeneous populations of PPDCs, extracellular matrix or cell lysate thereof, or conditioned medium thereof in a pharmaceutically acceptable carrier. Pharmaceutically acceptable carriers for the cells of the invention include organic or inorganic carrier substances suitable which do not deleteriously react with the cells of the invention or compositions or components thereof. To the extent they are biocompatible, suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences ($17^{th}$ Ed., Mack Pub. Co., Easton, Pa.) and WO 96/05309, each of which are incorporated by reference herein.

The dosage (e.g., the number of cells to be administered) and frequency of administration of the pharmaceutical compositions of the invention will depend upon a number of factors, including but not limited to, the nature of the condition to be treated, the extent of the symptoms of the condition, characteristics of the patient (e.g., age, size, gender, health).

For example but not by way of limitation, PPDCs, extracellular matrix or cell lysates thereof, conditioned medium, compositions, and matrices produced according to the invention can be used to repair or replace damaged or destroyed cartilage tissue, to augment existing cartilage tissue, to introduce new or altered tissue, to modify artificial prostheses, or to join biological tissues or structures. For example, some embodiments of the invention would include (i) hip prostheses coated with replacement cartilage tissue constructs grown in three-dimensional cultures; (ii) knee reconstruction with cartilage tissue constructs; (iii) prostheses of other joints requiring reconstruction and/or replacement of articular cartilage; and (iv) cosmetic reconstruction with cartilage tissue constructs.

For example, the evaluation of internal derangements of articular cartilage in for example, the knee, hip, elbow, ankle and the glenohumeral joint, may be performed by arthroscopic techniques. In some embodiments, the injured or deteriorated portion of cartilage tissue is removed, for example, by arthroscopic surgery, followed by cartilage grafting. Cartilage tissue constructs may also be employed in reconstructive surgery for different types of joints. Detailed procedures have been described in Resnick, D., and Niwayama, G., (eds), 1988, Diagnosis of Bone and Joint Disorders, 2d ed., W. B. Sanders Co., which is incorporated herein by reference.

Repair or replacement of damaged cartilage may be enhanced by fixation of the implanted cells and/or cartilage tissue at the site of repair. Various methods can be used to fix the new cells and/or cartilage tissue in place, including: patches derived from biocompatible tissues, which can be placed over the site; bioabsorbable sutures or other fasteners, e.g., pins, staples, tacks, screws and anchors; non-absorbable fixation devices, e.g., sutures, pins, screws and anchors; adhesives.

As another example but not by way of limitation, PPDCs, extracellular matrix or cell lysates thereof, conditioned medium, and the bone tissue produced according to the invention can be used to repair or replace damaged or destroyed bone tissue, to augment existing bone tissue, to introduce new or altered tissue, or to modify artificial prostheses. The cells of the invention may be administered alone, in a pharmaceutically acceptable carrier, or seeded on or in a matrix as described herein.

Use of PPDCs for Transplantation

The treatment methods of the subject invention involve the implantation of PPDCs or trans-differentiated cells into individuals in need thereof. The cells of the present invention may be allogeneic or autologous and may be delivered to the site of therapeutic need or "home" to the site.

The cells of the present invention may be differentiated in vitro prior to implantation in a patient. In vitro differentiation allows for controlled application of bioactive factors.

The cells of the present invention may be induced to differentiate in situ or may be introduced in vivo to provide trophic support to endogenous cells. The appropriate cell implantation dosage in humans can be determined from existing information relating to either the activity of the cells or the density of cells for bone or cartilage replacement. This information is also useful in calculating an appropriate dosage of implanted material. Additionally, the patient can be monitored to determine if additional implantation can be made or implanted material reduced accordingly.

To enhance the differentiation, survival or activity of implanted cells, additional bioactive factors may be added including growth factors, anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine), and local anesthetics. To enhance vascularization and survival of transplanted bone tissue, angiogenic factors such as VEGF, PDGF or bFGF can be added either alone or in combination with endothelial cells or their precursors including CD34+, CD34+/CD117+ cells.

Alternatively, PPDCs to be transplanted may be genetically engineered to express such growth factors, antioxidants, antiapoptotic agents, anti-inflammatory agents, or angiogenic factors.

PPDCs can be used to treat diseases or conditions of bone or cartilage or to augment or replace bone or cartilage. The disease or conditions to be treated include but are not limited to osteoarthritis, osteoporosis, rheumatoid arthritis, chondrosis deformans, dental and oral cavity disease (e.g., tooth fracture and defects), joint replacement, congenital abnormalities, bone fracture, and tumors (benign and malignant).

One or more other components may be added to transplanted cells, including selected extracellular matrix components, such as one or more types of collagen known in the art, and/or growth factors, platelet-rich plasma, and drugs. Alternatively, the cells of the invention may be genetically engineered to express and produce for growth factors. Details on genetic engineering of the cells of the invention are provided infra. Bioactive factors which may be usefully incorporated into the cell formulation include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPOXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine), and local anesthetics. For example, the cells may be co-administered with scar inhibitory factor as described in U.S. Pat. No. 5,827,735, incorporated herein by reference.

Formulation of PPDCs for Transplantation

In a non-limiting embodiment, a formulation comprising the cells of the invention is prepared for administration directly to the site where the production of new cartilage or bone tissue is desired. For example, and not by way of limitation, the cells of the invention may be suspended in a hydrogel solution for injection. Examples of suitable hydrogels for use in the invention include self-assembling peptides, such as RAD16. Alternatively, the hydrogel solution containing the cells may be allowed to harden, for instance in a mold, to form a matrix having cells dispersed therein prior to implantation. Or, once the matrix has hardened, the cell formations may be cultured so that the cells are mitotically expanded prior to implantation. The hydrogel is an organic polymer (natural or synthetic) which is cross-linked via covalent, ionic, or hydrogen bonds to create a three-dimensional open-lattice structure which entraps water molecules to form a gel. Examples of materials which can be used to form a hydrogel include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the support for the PPDCs of the invention is biodegradable.

In some embodiments of the invention, the formulation comprises an in situ polymerizable gel, as described, for example, in U.S. Patent Application Publication 2002/0022676; Anseth et al., J. Control Release, 78(1-3): 199-209 (2002); Wang et al., Biomaterials, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is crosslinked with dissolved multivalent cations in aqueous media at room temperature or below to form hydrogel matrices.

Biodegradable polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl.

Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., *Macromolecule* 10:824 (1977). Methods of synthesis of the hydrogel materials, as well as methods for preparing such hydrogels, are known in the art.

Other components may also be included in the formulation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation of tissue or its physicochemical characteristics, or as support for the viability of the cells, or inhibition of inflammation or rejection. The cells may be covered by an appropriate wound covering to prevent cells from leaving the site. Such wound coverings are known as those of skill in the art.

Formulation of a Cartilage or Bone Tissue Patch

Culture or co-cultures of PPDCs in a pre-shaped well enables the manufacture of a tissue patch of pre-determined thickness and volume. The volume of the resulting tissue patch is dependent upon the volume of the well and upon the number of PPDCs in the well. Tissue of optimal pre-determined volume may be prepared by routine experimentation by altering either or both of the aforementioned parameters.

The cell contacting surface of the well may be coated with a molecule that discourages adhesion of PPDCs to the cell contacting surface. Preferred coating reagents include silicon based reagents i.e., dichlorodimethylsilane or polytetrafluoroethylene based reagents, i.e., TEFLON. Procedures for coating materials with silicon based reagents, specifically dichlorodimethylsilane, are well known in the art. See for example, Sambrook et al. (1989) "Molecular Cloning A Laboratory Manual", Cold Spring Harbor Laboratory Press, the disclosure of which is incorporated by reference herein. It is appreciated that other biocompatible reagents that prevent the attachment of cells to the surface of the well may be useful in the practice of the instant invention.

Alternatively, the well may be cast from a pliable or moldable biocompatible material that does not permit attachment of cells per se. Preferred materials that prevent such cell attachment include, but are not limited to, agarose, glass, untreated cell culture plastic and polytetrafluoroethylene, i.e., TEFLON. Untreated cell culture plastics, i.e., plastics that have not been treated with or made from materials that have an electrostatic charge are commercially available, and may be purchased, for example, from Falcon Labware, Becton-Dickinson, Lincoln Park, N.J. The aforementioned materials, however, are not meant to be limiting. It is appreciated that any other pliable or moldable biocompatible material that inherently discourages the attachment of PPDCs may be useful in the practice of the instant invention.

The size and shape of the well may be determined by the size and shape of the tissue defect to be repaired. For example, it is contemplated that the well may have a cross-sectional surface area of 25 cm$^2$. This is the average cross-sectional surface area of an adult, human femoral chondyle. Accordingly, it is anticipated that a single piece of cartilage may be prepared in accordance with the invention in order to resurface the entire femoral chondyle. The depth of the well is preferably greater than about 0.3 cm and preferably about 0.6 cm in depth. The thickness of natural articular cartilage in an adult articulating joint is usually about 0.3 cm. Accordingly, the depth of the well should be large enough to permit a cartilage patch of about 0.3 cm to form. The well should be deep enough to contain culture medium overlaying the tissue patch.

It is contemplated that a tissue patch prepared in accordance with the invention may be "trimmed" to a pre-selected size and shape by a surgeon performing surgical repair of the damaged tissue. Trimming may be performed with the use of a sharp cutting implement, i.e., a scalpel, a pair of scissors or an arthroscopic device fitted with a cutting edge, using procedures well known in the art.

The pre-shaped well may be cast in a block of agarose gel under aseptic conditions. Agarose is an economical, biocompatible, pliable and moldable material that can be used to cast pre-shaped wells, quickly and easily. As mentioned above, the dimensions of the well may dependent upon the size of the resulting tissue plug that is desired.

A pre-shaped well may be prepared by pouring a hot solution of molten LT agarose (BioRad, Richmond, Calif.) into a tissue culture dish containing a cylinder, the cylinder having dimensions that mirror the shape of the well to be formed. The size and shape of the well may be chosen by the artisan and may be dependent upon the shape of the tissue defect to be repaired. Once the agarose has cooled and solidified around the cylinder, the cylinder is carefully removed with forceps. The surface of the tissue culture dish that is exposed by the removal of the cylinder is covered with molten agarose. This seals the bottom of the well and provides a cell adhesive surface at the base of the well. When the newly added molten LT agarose cools and solidifies, the resulting pre-shaped well is suitable for culturing, and inducing the differentiation of PPDCs. It is appreciated, however, that alternative methods may be used to prepare a pre-shaped well useful in the practice of the invention.

PPDCs in suspension may be seeded into and cultured in the pre-shaped well. The PPDCs may be induced to differentiate to a chondrogenic or osteogenic phenotype in culture in the well or may have been induced to differentiate prior to seeding in the well. The cells may be diluted by the addition of culture medium to a cell density of about $1\times10^5$ to $1\times10^9$ PPDCs per milliliter.

The cells may form a cohesive plug of cells. The cohesive plug of cells may be removed from the well and surgically implanted into the tissue defect. It is anticipated that undifferentiated PPDCs may differentiate in situ thereby to form tissue in vivo.

Cartilage and bone defects may be identified inferentially by using computer aided tomography (CAT scanning); X-ray examination, magnetic resonance imaging (MRI), analysis of synovial fluid or serum markers or by any other procedures known in the art. Defects in mammals also are readily identifiable visually during arthroscopic examination orduring open surgery of the joint. Treatment of the defects can be effected during an arthroscopic or open surgical procedure using the methods and compositions disclosed herein.

Accordingly, once the defect has been identified, the defect may be treated by the following steps of (1) surgically implanting at the pre-determined site a tissue patch prepared by the methodologies described herein, and (2) permitting the tissue patch to integrate into pre-determined site.

The tissue patch optimally has a size and shape such that when the patch is implanted into the defect, the edges of the implanted tissue contact directly the edges of the defect. In addition, the tissue patch may be fixed in place during the surgical procedure. This can be effected by surgically fixing the patch into the defect with biodegradable sutures and/or by applying a bioadhesive to the region interfacing the patch and the defect.

In some instances, damaged tissue may be surgically excised prior the to implantation of the patch of tissue.

Transplantation of PPDCs Using Scaffolds

The cells of the invention or co-cultures thereof may be seeded onto or into a three-dimensional scaffold and implanted in vivo, where the seeded cells will proliferate on the framework and form a replacement cartilage or bone tissue in vivo in cooperation with the cells of the patient.

In some aspects of the invention, the matrix comprises decellularized tissue, such as extracellular matrix, cell lysates (e.g., soluble cell fractions), or combinations thereof, of the PPDCs. In some embodiments, the matrix is biodegradable. In some aspects of the invention, the matrix comprises natural or synthetic polymers. Matrices of the invention include biocompatible scaffolds, lattices, self-assembling structures and the like, whether biodegradable or not, liquid or solid. Such matrices are known in the arts of cell-based therapy, surgical repair, tissue engineering, and wound healing. Preferably the matrices are pretreated (e.g., seeded, inoculated, contacted with) with the cells, extracellular matrix, conditioned medium, cell lysate, or combination thereof, of the invention. More preferably the matrices are populated with cells in close association to the matrix or its spaces. In some aspects of the invention, the cells adhere to the matrix. In some embodiments, the cells are contained within or bridge interstitial spaces of the matrix. Most preferred are those seeded matrices wherein the cells are in close association with the matrix and which, when used therapeutically, induce or support ingrowth of the patient's cells and/or proper angiogenesis. The seeded matrices can be introduced into a patient's body in any way known in the art, including but not limited to implantation, injection, surgical attachment, transplantation with other tissue, injection, and the like. The matrices of the invention may be configured to the shape and/or size of a tissue or organ in vivo.

For example, but not by way of limitation, the scaffold may be designed such that the scaffold structure: (1) supports the seeded cells without subsequent degradation; (2) supports the cells from the time of seeding until the tissue transplant is remodeled by the host tissue; (2) allows the seeded cells to attach, proliferate, and develop into a tissue structure having sufficient mechanical integrity to support itself in vitro, at which point, the scaffold is degraded. A review of scaffold design is provided by Hutmacher, *J. Biomat. Sci. Polymer Edn.*, 12(1):107-124 (2001).

Scaffolds of the invention can be administered in combination with any one or more growth factors, cells, for example stem cells, bone marrow cells, chondrocytes, chondroblasts, osteocytes, osteoblasts, osteoclasts, bone lining cells, or their precursors, drugs or other components described above that stimulate tissue formation or otherwise enhance or improve the practice of the invention. The PPDCs to be seeded onto the scaffolds may be genetically engineered to express growth factors or drugs.

The cells of the invention can be used to produce new tissue in vitro, which can then be implanted, transplanted or otherwise inserted into a site requiring tissue repair, replacement or augmentation in a patient.

In a non-limiting embodiment, the cells of the invention are used to produce a three-dimensional tissue construct in vitro, which is then implanted in vivo. As an example of the production of three-dimensional tissue constructs, see U.S. Pat. No. 4,963,489, which is incorporated herein by reference. For example, the cells of the invention may be inoculated or "seeded" onto a three-dimensional framework or scaffold, and proliferated or grown in vitro to form a living tissue that can be implanted in vivo.

The cells of the invention can be grown freely in a culture vessel to sub-confluency or confluency, lifted from the culture and inoculated onto a three-dimensional framework. Inoculation of the three-dimensional framework with a high concentration of cells, e.g., approximately $10^6$ to $5 \times 10^7$ cells per milliliter, will result in the establishment of the three-dimensional support in relatively shorter periods of time.

Examples of scaffolds which may be used in the present invention include nonwoven mats, porous foams, or self assembling peptides. Nonwoven mats may, for example, be formed using fibers comprised of a synthetic absorbable copolymer of glycolic and lactic acids (PGA/PLA), sold under the tradename VICRYL (Ethicon, Inc., Somerville, N.J.). Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, are also possible scaffolds. Hydrogels such as self-assembling peptides (e.g., RAD16) may also be used. These materials are frequently used as supports for growth of tissue.

The three-dimensional framework may be made of ceramic materials including, but not limited to: mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS (University of Florida, Gainesville, Fla.), and mixtures thereof. There are a number of suitable porous biocompatible ceramic materials currently available on the commercial market such as SURGIBON (Unilab Surgibone, Inc., Canada), ENDOBON (Merck Biomaterial France, France), CEROS (Mathys, A. G., Bettlach, Switzerland), and INTERPORE (Interpore, Irvine, Calif., United States), and mineralized collagen bone grafting products such as HEALOS (Orquest, Inc., Mountain View, Calif.) and VITOSS, RHAKOSS, and CORTOSS (Orthovita, Malvern, Pa.). The framework may be a mixture, blend or composite of natural and/or synthetic materials. In some embodiments, the scaffold is in the form of a cage. In a preferred embodiment, the scaffold is coated with collagen.

According to a preferred embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling.

In another preferred embodiment the cells of the invention are seeded onto foam scaffolds that may be composite structures. In addition, the three-dimensional framework may be molded into a useful shape, such as that of the external portion of the ear, a bone, joint or other specific structure in the body to be repaired, replaced or augmented.

In another preferred embodiment, the cells of the invention are seeded onto a framework comprising a prosthetic device for implantation into a patient, as described in U.S. Pat. No. 6,200,606, incorporated herein by reference. As described therein, a variety of clinically useful prosthetic devices have been developed for use in bone and cartilage grafting procedures. (see e.g. Bone Grafts and Bone Substitutions. Ed. M. B. Habal & A. H. Reddi, W. B. Saunders Co., 1992). For example, effective knee and hip replacement devices have been and continue to be widely used in the clinical environment. Many of these devices are fabricated using a variety of inorganic materials having low immunogenic activity, which safely function in the body. Examples of synthetic materials which have been tried and proven include titanium alloys, calcium phosphate, ceramic hydroxyapatite, and a variety of stainless steel and cobalt-chrome alloys. These materials provide structural support and can form a scaffolding into which host vascularization and cell migration can occur. The present invention provides a source of cells which may be used to "seed" such prosthetic devices. In the preferred embodiment PPDCs are first mixed with a carrier material before application to a device. Suitable carriers well known to those skilled in the art include, but are not limited to, gelatin, fibrin, collagen, starch, polysaccharides, saccharides, proteoglycans, synthetic polymers, calcium phosphate, or ceramics.

The framework may be treated prior to inoculation of the cells of the invention in order to enhance cell attachment. For example, prior to inoculation with the cells of the invention, nylon matrices could be treated with 0.1 molar acetic acid and incubated in polylysine, PBS, and/or collagen to coat the nylon. Polystyrene could be similarly treated using sulfuric acid.

In addition, the external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some embodiments, the scaffold is comprised of or is treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the scaffold non-thrombogenic. Such treatments include anti-thrombotic agents such as heparin, and treatments which alter the surface charge of the material such as plasma coating.

In some embodiments, the surface of the scaffold is textured. For example, in some aspects of the invention, the scaffold is provided with a groove and ridge pattern. The grooves are preferably less than about 500 microns, more preferably less than about 100 microns, and most preferably between about 10 nanometers and 10 microns. Such "microgrooves" allow the cells to align and/or migrate guided by the surface grooves. See, e.g., Odontology. 2001;89(1):2-11. The textured scaffold may be used, for example, as a dental implant.

In some embodiments, it is important to re-create in culture the cellular microenvironment found in vivo, such that the extent to which the cells of the invention are grown prior to implantation in vivo or use in vitro may vary. In addition, growth factors, chondrogenic differentiation inducing agents, osteogenic inducing agents, and angiogenic factors may be added to the culture medium prior to, during, or subsequent to inoculation of the cells to trigger differentiation and tissue formation by the PPDCs or co-cultures thereof.

The three-dimensional framework may be modified so that the growth of cells and the production of tissue thereon is enhanced, or so that the risk of rejection of the implant is reduced. Thus, one or more biologically active compounds, including, but not limited to, anti-inflammatories, immunosuppressants or growth factors, may be added to the framework.

Therapeutic Uses for Extracellular Matrix or Cell Lysate Derived from PPDCs

As an alternative to implanting the cells of the invention, or living tissue produced therefrom, a subject in need of tissue repair, replacement, or augmentation may benefit from the administration of a component or product of PPDCs, such as the extracellular matrix (ECM) or cell lysate produced by those cells.

In some embodiments, after the cells of the invention have been cultured in vitro, such as, for example, by using a three-dimensional scaffold system described herein, such that a desired amount of ECM has been secreted onto the framework. Once ECM is secreted onto the framework, the cells may be removed. The ECM may be processed for further use, for example, as an injectable preparation.

In some embodiments, the cells are killed and cellular debris (e.g., cellular membranes) is removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure. Once the cells have been killed, the cellular membranes may be disrupted and cellular debris removed by treatment with a mild detergent rinse, such as EDTA, CHAPS or a zwitterionic detergent. An advantage to using a mild detergent rinse is that it solubilizes membrane-bound proteins, which are often highly antigenic.

Alternatively, the tissue can be enzymatically digested and/or extracted with reagents that break down cellular membranes. Example of such enzymes include, but are not limited to, hyaluronidase, dispase, proteases, and nucleases (for example, deoxyribonuclease and ribonuclease). Examples of detergents include non-ionic detergents such as, for example, alkylaryl polyether alcohol (TRITON® X-100), octylphenoxy polyethoxy-ethanol (Rohm and Haas Philadelphia, Pa.), BRIJ-35, a polyethoxyethanol lauryl ether (Atlas Chemical Co., San Diego, Calif.), polysorbate 20 (TWEEN 20®), a polyethoxyethanol sorbitan monolaureate (Rohm and Haas), polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain.

Scaffolds comprising the ECm may be used therapeutically as described above. Alternatively, ECM may be collected from the scaffold. The collection of the ECM can be accomplished in a variety of ways, depending, for example, on whether the scaffold is biodegradable or non-biodegradable. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM or cell lysate produced by the cells of the invention.

Once the ECM has been collected, it may be processed further. The ECM can be homogenized to fine particles using techniques well known in the art such as, for example, by sonication, so that they can pass through a surgical needle. ECM components can be crosslinked, if desired, by gamma irradiation. Preferably, the ECM can be irradiated between 0.25 to 2 mega rads to sterilize and crosslink the ECM. Chemical crosslinking using agents that are toxic, such as glutaraldehyde, is possible but not generally preferred.

Cell lysates prepared from the populations of the postpartum-derived cells also have many utilities. In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods. Use of soluble cell fractions in vivo allows the beneficial intracellular milieu to be used in a patient without triggering rejection or an adverse response. Methods of lysing cells are well-known in the art and include various means of mechanical disruption, enzymatic disruption, or chemical disruption, or combinations thereof. Such cell lysates may be prepared from cells directly in their growth medium and thus containing secreted growth factors and the like, or may be prepared from cells washed free of medium in, for example, PBS or other solution. Washed cells may be resuspended at concentrations greater than the original population density if preferred. Cell lysates prepared from populations of postpartum-derived cells may be used as is, further concentrated, by for example, ultrafiltration or lyophilization, or even dried, partially purified, combined with pharmaceutically acceptable carriers or diluents as are known in the art, or combined with other compounds such as biologicals, for example pharmaceutically useful protein compositions. Cell lysates may be used in vitro or in vivo, alone or for example, with cells. The cell lysates, if introduced in vivo, may be introduced locally at a site of treatment, or remotely to provide, for example needed cellular growth factors to a patient.

The amounts and/or ratios of proteins may be adjusted by mixing the ECM or cell lysate produced by the cells of the invention with ECM or cell lysate of one or more other cell types. In addition, biologically active substances such as proteins, growth factors and/or drugs, can be incorporated into the ECM or cell lysate preparation. Exemplary biologically active substances include anti-inflammatory agents and growth factors which promote healing and tissue repair. Cells may be co-administered with the ECM or cell lysates of the invention. ECM or cell lysate of PPDCs may be formulated for administration as described above for PPDCs.

The above described process for preparing injectable ECM or cell lysate is preferably carried out under sterile conditions using sterile materials. The processed ECM or cell lysate in a pharmaceutically acceptable carrier can be injected intradermally or subcutaneously to treat bone or cartilage conditions, for example, by augmenting tissue or repairing or correcting congenital anomalies, acquired defects or cosmetic defects.

Use of PPDCs for In Vitro Screening of Drug Efficacy or Toxicity

The cells and tissues of the invention may be used in vitro to screen a wide variety of compounds for effectiveness and cytotoxicity of pharmaceutical agents, growth/regulatory factors, anti-inflammatory agents. To this end, the cells of the invention, or tissue cultures described above, are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the number of living cells in vitro, e.g., by total cell counts, and differential cell counts. This may be accomplished using standard cytological and/or histological techniques, including the use of immunocytochemical techniques employing antibodies that define type-specific cellular antigens. The effect of various drugs on the cells of the invention either in suspension culture or in the three-dimensional system described above may be assessed.

The cells and tissues of the invention may be used as model systems for the study of physiological or pathological conditions. For example, joints that are immobilized suffer relatively quickly in a number of respects. The metabolic activity of chondrocytes appears affected as loss of proteoglycans and an increase in water content are soon observed. The normal white, glistening appearance of the cartilage changes to a dull, bluish color, and the cartilage thickness is reduced. However, the amount of this change that is due to nutritional deficiency versus the amount due to upset in the stress-dependent metabolic homeostasis is not yet clear. The cells and tissues of the invention may be used to determine the nutritional requirements of cartilage under different physical conditions, e.g., intermittent pressurization, and by pumping action of nutrient medium into and out of the cartilage construct. This may be especially useful in studying underlying causes for age-related or injury-related decrease in tensile strength of, for example, articular cartilage, e.g., in the knee, that predispose the weakened cartilage to traumatic damage.

The cells and tissues of the invention may also be used to study the mechanism of action of cytokines, growth factors and inflammatory mediators, e.g., IL-1, TNF and prostaglandins. In addition, cytotoxic and/or pharmaceutical agents can be screened for those that are most efficacious for a particular patient, such as those that reduce or prevent resorption of cartilage or bone otherwise enhance the balanced growth thereof. Agents that prove to be efficacious in vitro could then be used to treat the patient therapeutically.

Use of PPDCs to Produce Biological Molecules

In a further embodiment, the cells of the invention can be cultured in vitro to produce biological products in high yield. For example, such cells, which either naturally produce a particular biological product of interest (e.g., a growth factor, regulatory factor, or peptide hormone), or have been genetically engineered to produce a biological product, could be clonally expanded using, for example, the three-dimensional culture system described above. If the cells excrete the biological product into the nutrient medium, the product can be readily isolated from the spent or conditioned medium using standard separation techniques, e.g., such as differential protein precipitation, ion-exchange chromatography, gel filtration chromatography, electrophoresis, and high performance liquid chromatography. A "bioreactor" may be used to take advantage of the flow method for feeding, for example, a three-dimensional culture in vitro.

Essentially, as fresh media is passed through the three-dimensional culture, the biological product is washed out of the culture and may then be isolated from the outflow, as above.

Alternatively, a biological product of interest may remain within the cell and, thus, its collection may require that the cells be lysed. The biological product may then be purified using any one or more of the above-listed techniques.

Kits

The PPDCs and components and products thereof can conveniently be employed as part of a kit, for example, for culture or implantation. Accordingly, the invention provides a kit including the PPDCs and additional components, such as a matrix (e.g., a scaffold), hydrating agents (e.g., physiologically-compatible saline solutions, prepared cell culture media), cell culture substrates (e.g., culture dishes, plates, vials, etc.), cell culture media (whether in liquid or powdered form), antibiotic compounds, hormones, and the like. While the kit can include any such components, preferably it includes all ingredients necessary for its intended use. If desired, the kit also can include cells (typically cryopreserved), which can be seeded into the lattice as described herein.

In another aspect, the invention provides kits that utilize the PPDCs, PPDC populations, components and products of PPDCs in various methods for augmentation, regeneration, and repair as described above. In some embodiments, the kits may include one or more cell populations, including at least PPDCs and a pharmaceutically acceptable carrier (liquid, semi-solid or solid). The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) PPDCs or components or products of PPDCs, (2) reagents for practicing the in vitro method, (3) other cells or cell populations, as appropriate, and (4) instructions for conducting the in vitro method.

Cryopreservation and Banking PPDCs

PDCs of the invention can be cryopreserved and maintained or stored in a "cell bank". Cryopreservation of cells of the invention may be carried out according to known methods. For example, but not by way of limitation, cells may be suspended in a "freeze medium" such as, for example, culture medium further comprising 0 to 95 percent FBS and 0 to 10 percent dimethylsulfoxide (DMSO), with or without 5 to 10 percent glycerol, at a density, for example, of about 0.5 to $10 \times 10^6$ cells per milliliter. The cryopreservation medium may comprise cryopreservation agents including but not limited to methylcellulose. The cells are dispensed into glass or plastic ampoules that are then sealed and transferred to the freezing chamber of a controlled rate freezer. The optimal rate of freezing may be determined empirically. A programmable rate freezer for example, can give a change in temperature of −1 to −10° C. per minute. The preferred cryopreservation temperature is about −80° C. to about −180° C., more preferably is about −90° C. to about −160° C., and most preferably is about −125 to about −140° C. Cryopreserved cells preferably are transferred to liquid nitrogen prior to thawing for use. In some embodiments, for example, once the ampoules have reached about −90° C., they are transferred to a liquid nitrogen storage area. Cryopreserved cells can be stored for a period of years.

The cryopreserved cells of the invention constitute a bank of cells, portions of which can be "withdrawn" by thawing and then used as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as DMEM conditioned with 10 percent FBS.

In yet another aspect, the invention also provides for banking of tissues, cells, cellular components and cell populations of the invention. As discussed above, the cells are readily cryopreserved. The invention therefore provides methods of cryopreserving the cells in a bank, wherein the cells are stored frozen and associated with a complete characterization of the cells based on immunological, biochemical and genetic properties of the cells. The cells so frozen can be used for autologous, syngeneic, or allogeneic therapy, depending on the requirements of the procedure and the needs of the patient. Preferably, the information on each cryopreserved sample is stored in a computer, which is searchable based on the requirements of the surgeon, procedure and patient with suitable matches being made based on the characterization of the cells or populations. Preferably, the cells of the invention are grown and expanded to the desired quantity of cells and therapeutic cell compositions are prepared either separately or as co-cultures, in the presence or absence of a matrix or support. While for some applications it may be preferable to use cells freshly prepared, the remainder can be cryopreserved and banked by freezing the cells and entering the information in the computer to associate the computer entry with the samples. Even where it is not necessary to match a source or donor with a recipient of such cells, for immunological purposes, the bank system makes it easy to match, for example, desirable biochemical or genetic properties of the banked cells to the therapeutic needs. Upon matching of the desired properties with a banked sample, the sample is retrieved, and readied for therapeutic use. Cell lysates or components prepared as described herein may also be preserved (e.g., cryopreserved, lyophilized) and banked in accordance with the present invention.

The following examples describe several aspects of embodiments of the invention in greater detail. These examples are provided to further illustrate, not to limit, aspects of the invention described herein.

EXAMPLES

Example 1

Derivation of Cells from Postpartum Tissues

The objective of this study was to derive populations of cells from placental and umbilical cord tissues. Postpartum umbilical cord and placenta were obtained upon birth of either a full term or pre-term pregnancy. Cells were harvested from 5 separate donors of umbilical cord and placental tissue. Different methods of cell isolation were tested for their ability to yield cells with: 1) the potential to differentiate into cells with different phenotypes, or 2) the potential to provide critical trophic factors useful for other cells and tissues.

Methods & Materials

Umbilical cord cell derivation. Umbilical cords were obtained from National Disease Research Interchange (NDRI, Philadelphia, Pa.). The tissues were obtained following normal deliveries. The cell isolation protocol was performed aseptically in a laminar flow hood. To remove blood and debris, the umbilical cord was washed in phosphate buffered saline (PBS; Invitrogen, Carlsbad, Calif.) in the presence of antimycotic and antibiotic (100 Units/milliliter penicillin, 100 micrograms/milliliter streptomycin, 0.25 micrograms/milliliter amphotericin B (Invitrogen Carlsbad, Calif.)). The tissues were then mechanically dissociated in 150 $cm^2$ tissue culture plates in the presence of 50 milliliters of medium (DMEM-Low glucose or DMEM-High glucose; Invitrogen) until the tissue was minced into a fine pulp. The chopped tissues were transferred to 50 milliliter conical tubes (approximately 5 grams of tissue per tube). The tissue was then digested in either DMEM-Low glucose medium or DMEM-High glucose medium, each containing antimycotic and antibiotic (100 Units/milliliter penicillin, 100 micrograms/milliliter streptomycin, 0.25 micrograms/milliliter amphotericin B (Invitrogen)) and digestion enzymes. In some experiments, an enzyme mixture of collagenase and dispase was used ("C:D;" collagenase (Sigma, St Louis, Mo.), 500 Units/milliliter; and dispase (Invitrogen), 50 Units/milliliter in DMEM-Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, and the supernatant was aspirated. The pellet was resuspended in 20 milliliters of Growth medium (DMEM-Low glucose (Invitrogen), 15 percent (v/v) fetal bovine serum (FBS; defined bovine serum; Lot #AND18475;

Hyclone, Logan, Utah), 0.001% (v/v) 2-mercaptoethanol (Sigma), 100 Units/milliliter of penicillin, 100 microgram/milliliter streptomycin, 0.25 microgram/milliliter amphotericin B (Invitrogen, Carlsbad, Calif.). The cell suspension was filtered through a 70-micrometer nylon cell strainer (BD Biosciences). An additional 5 milliliter rinse comprising Growth medium was passed through the strainer. The cell suspension was then passed through a 40-micrometer nylon cell strainer (BD Biosciences) and chased with a rinse of an additional 5 milliliters of Growth medium.

The filtrate was resuspended in Growth medium (total volume 50 milliliters) and centrifuged at 150×g for 5 minutes. The supernatant was aspirated, and the cells were resuspended in 50 milliliters of fresh Growth medium. This process was repeated twice more.

Upon the final centrifugation supernatant was aspirated and the cell pellet was resuspended in 5 milliliters of fresh Growth medium. The number of viable cells was determined using Trypan Blue staining. Cells were then cultured under standard conditions.

The cells isolated from umbilical cord cells were seeded at 5,000 cells/cm$^2$ onto gelatin-coated T-75 cm$^2$ flasks (Corning Inc., Corning, N.Y.) in Growth medium (DMEM-Low glucose (Invitrogen), 15 percent (v/v) defined bovine serum (Hyclone, Logan, Utah; Lot #AND18475), 0.001 percent (v/v) 2-mercaptoethanol (Sigma), 100 Units/milliliter penicillin, 100 micrograms/milliliter streptomycin, 0.25 micrograms/milliliter amphotericin B (Invitrogen)). After about 2-4 days, spent medium was aspirated from the flasks. Cells were washed with PBS three times to remove debris and blood-derived cells. Cells were then replenished with Growth medium and allowed to grow to confluence (about 10 days from passage 0 to passage 1). On subsequent passages (from passage 1 to 2, etc.), cells reached sub-confluence (75-85 percent confluence) in 4-5 days. For these subsequent passages, cells were seeded at 5000 cells/cm$^2$. Cells were grown in a humidified incubator with 5 percent carbon dioxide and 20 percent oxygen at 37° C.

Placental Cell Isolation. Placental tissue was obtained from NDRI (Philadelphia, Pa.). The tissues were from a pregnancy and were obtained at the time of a normal surgical delivery. Placental cells were isolated as described for umbilical cord cell isolation.

The following example applies to the isolation of separate populations of maternal-derived and neonatal-derived cells from placental tissue.

The cell isolation protocol was performed aseptically in a laminar flow hood. The placental tissue was washed in phosphate buffered saline (PBS; Invitrogen, Carlsbad, Calif.) in the presence of antimycotic and antibiotic (100 U/milliliter penicillin, 100 microgram/milliliter streptomycin, 0.25 microgram/milliliter amphotericin B; Invitrogen) to remove blood and debris. The placental tissue was then dissected into three sections: top-line (neonatal side or aspect), mid-line (mixed cell isolation neonatal and maternal or villous region), and bottom line (maternal side or aspect).

The separated sections were individually washed several times in PBS with antibiotic/antimycotic to further remove blood and debris. Each section was then mechanically dissociated in 150 cm$^2$ tissue culture plates in the presence of 50 milliliters of DMEM-Low glucose (Invitrogen) to a fine pulp. The pulp was transferred to 50 milliliter conical tubes. Each tube contained approximately 5 grams of tissue. The tissue was digested in either DMEM-Low glucose or DMEM-High glucose medium containing antimycotic and antibiotic (100 Units/milliliter penicillin, 100 micrograms/milliliter streptomycin, 0.25 micrograms/milliliter amphotericin B (Invitrogen)) and digestion enzymes. In some experiments an enzyme mixture of collagenase and dispase ("C:D") was used containing collagenase (Sigma, St Louis, Mo.) at 500 Units/milliliter and dispase (Invitrogen) at 50 Units/milliliterin DMEM-Low glucose medium. In other experiments a mixture of collagenase, dispase, and hyaluronidase (C:D:H) was used (collagenase, 500 Units/milliliter; dispase, 50 Units/milliliter; and hyaluronidase (Sigma), 5 Units/milliliter in DMEM-Low glucose). The conical tubes containing the tissue, medium, and digestion enzymes were incubated for 2 h at 37° C. in an orbital shaker (Environ, Brooklyn, N.Y.) at 225 rpm.

After digestion, the tissues were centrifuged at 150×g for 5 minutes, the resultant supernatant was aspirated off. The pellet was resuspended in 20 milliliter of Growth medium (DMEM-Low glucose (Invitrogen), 15% (v/v) fetal bovine serum (FBS; defined bovine serum; Lot #AND18475; Hyclone, Logan, Utah), 0.001% (v/v) 2-mercaptoethanol (Sigma, St. Louis, Mo.), antibiotic/antimycotic (100 U/milliliter penicillin, 100 microgram/milliliter streptomycin, 0.25 microgram/milliliter amphotericin B; Invitrogen)). The cell suspension was filtered through a 70 micrometer nylon cell strainer (BD Biosciences), chased by a rinse with an additional 5 milliliters of Growth medium. The total cell suspension was passed through a 40 micrometer nylon cell strainer (BD Biosciences) followed with an additional 5 milliliters of Growth medium as a rinse.

The filtrate was resuspended in Growth medium (total volume 50 milliliters) and centrifuged at 150×g for 5 minutes. The supernatant was aspirated and the cell pellet was resuspended in 50 milliliters of fresh Growth medium. This process was repeated twice more. After the final centrifugation, supernatant was aspirated and the cell pellet was resuspended in 5 milliliters of fresh Growth medium. A cell count was determined using the Trypan Blue Exclusion test. Cells were then cultured at standard conditions.

LIBERASE (Boehringer Mannheim Corp., Indianapolis, Ind.) Cell Isolation. Cells were isolated from umbilical cord in DMEM-Low glucose medium with LIBERASE (Boehringer Mannheim Corp., Indianapolis, Ind.) (2.5 milligrams per milliliter, Blendzyme 3; Roche Applied Sciences, Indianapolis, Ind.) and hyaluronidase (5 Units/milliliter, Sigma). Digestion of the tissue and isolation of the cells was as described for other protease digestions above using a LIBERASE (Boehringer Mannheim Corp., Indianapolis, Ind.)/hyaluronidase mixture in place of the C:D or C:D:H enzyme mixture. Tissue digestion with LIBERASE (Boehringer Mannheim Corp., Indianapolis, Ind.) resulted in the isolation of cell populations from postpartum tissues that expanded readily.

Cell isolation using other enzyme combinations. Procedures were compared for isolating cells from the umbilical cord using differing enzyme combinations. Enzymes compared for digestion included: i) collagenase; ii) dispase; iii) hyaluronidase; iv) collagenase:dispase mixture (C; D); v) collagenase:hyaluronidase mixture (C:H); vi) dispase:hyaluronidase mixture (D:H); and vii) collagenase:dispase:hyaluronidase mixture (C:D:H). Differences in cell isolation utilizing these different enzyme digestion conditions were observed (Table 1-1).

Isolation of cells from residual blood in the cords. Attempts were made to isolate pools of cells from umbilical cord by different approaches. In one instance umbilical cord was sliced and washed with Growth medium to dislodge the blood clots and gelatinous material. The mixture of blood, gelatinous material, and Growth medium was collected and centrifuged at 150×g. The pellet was resuspended and seeded onto gelatin-coated flasks in Growth medium. From these experiments a cell population was isolated that readily expanded.

Isolation of cells from Cord Blood. Cells have also been isolated from cord blood samples attained from NDRI. The isolation protocol used here was that of International Patent Application PCT/US2005/29971 by Ho et al. Samples (50 milliliter and 10.5 milliliters, respectively) of umbilical cord blood (NDRI, Philadelphia Pa.) were mixed with lysis buffer (filter-sterilized 155 millimolar ammonium chloride, 10 millimolar potassium bicarbonate, 0.1 millimolar EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The soluble cell fraction was centrifuged (10 minutes at 200 x g). The cell pellet was resuspended in complete minimal essential medium (Gibco, Carlsbad Calif.) containing 10 percent fetal bovine serum (Hyclone, Logan Utah), 4 millimolar glutamine (Mediatech Herndon, Va.), 100 Units penicillin per 100 milliliters and 100 micrograms streptomycin per 100 milliliters (Gibco, Carlsbad, Calif.). The resuspended cells were centrifuged (10 minutes at 200 x g), the supernatant was aspirated, and the cell pellet was washed in complete medium. Cells were seeded directly into either T75 flasks (Corning, NY), T75 laminin-coated flasks, or T175 fibronectin-coated flasks (both Becton Dickinson, Bedford, Mass.).

Isolation of postpartum-derived cells using different enzyme combinations and growth conditions. To determine whether cell populations can be isolated under different conditions and expanded under a variety of conditions immediately after isolation, cells were digested in Growth medium with or without 0.001 percent (v/v) 2-mercaptoethanol (Sigma, St. Louis, Mo.), using the enzyme combination of C:D:H, according to the procedures provided above. Placenta-derived cells so isolated were seeded under a variety of conditions. All cells were grown in the presence of penicillin/streptomycin. (Table 1-2).

Isolation of postpartum-derived cells using different enzyme combinations and growth conditions. In all conditions, cells attached and expanded well between passage 0 and 1 (Table 1-2). Cells in conditions 5 to 8 and 13 to 16 were demonstrated to proliferate well up to 4 passages after seeding at which point they were cryopreserved. All cells were banked.

Results

Cell isolation using different enzyme combinations. The combination of C:D:H provided the best cell yield following isolation and generated cells which expanded for many more generations in culture than the other conditions (Table 1-1). An expandable cell population was not attained using collagenase or hyaluronidase alone. No attempt was made to determine if this result is specific to the collagen that was tested.

Isolation of postpartum-derived cells using different enzyme combinations and growth conditions. Cells attached and expanded well between passage 0 and 1 under all conditions tested for enzyme digestion and growth (Table 1-2). Cells in experimental conditions 5-8 and 13-16 proliferated well up to 4 passages after seeding, at which point they were cryopreserved. All cells were banked.

Isolation of cells from residual blood in the cords. Nucleated cells attached and grew rapidly. These cells were analyzed by flow cytometry and were similar to cells obtained by enzyme digestion.

Isolation of cells from Cord Blood. The preparations contained red blood cells and platelets. No nucleated cells attached and divided during the first 3 weeks. The medium was changed 3 weeks after seeding and no cells were observed to attach and grow.

Summary. Populations of cells can be isolated from umbilical cord and placental tissue most efficiently using the enzyme combination collagenase (a matrix metalloprotease), dispase (neutral protease), and hyaluronidase (a mucolytic enzyme which breaks down hyaluronic acid). LIBERASE (Boehringer Mannheim Corp., Indianapolis, Ind.), which is a Blendzyme, may also be used. In the present study Blendzyme 3 which is collagenase (4 Wunsch units/g) and thermolysin (1714 casein Units/g) was also used together with hyaluronidase to isolate cells. These cells expand readily over many passages when cultured in Growth medium on gelatin-coated plastic.

Postpartum-derived cells were isolated from residual blood in the cords but not from cord blood. The presence of cells in blood clots washed from the tissue that adhere and grow under the conditions used may be due to cells being released during the dissection process.

TABLE 1-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key: + = good, ++ = very good, +++ = excellent, X = no success

TABLE 1-2

Isolation and culture expansion of postpartum-derived cells under varying conditions:

| Condition | Medium | 15% FBS | BME | Gelatin | 20% O2 | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/mL) |
| 6 | DMEM-Lg | N (2%) | Y | N (Laminin) | N (5%) | EGF/FGF (20 ng/mL) |

TABLE 1-2-continued

Isolation and culture expansion of postpartum-derived cells under varying conditions:

| Condition | Medium | 15% FBS | BME | Gelatin | 20% O2 | Growth Factors |
|---|---|---|---|---|---|---|
| 7 | DMEM-Lg | N (2%) | Y | N (Fibronectin) | Y | PDGF/VEGF |
| 8 | DMEM-Lg | N (2%) | Y | N (Fibronectin) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/mL) |
| 14 | DMEM-Lg | N (2%) | N | N (Laminin) | N (5%) | EGF/FGF (20 ng/mL) |
| 15 | DMEM-Lg | N (2%) | N | N (Fibronectin) | Y | PDGF/VEGF |
| 16 | DMEM-Lg | N (2%) | N | N (Fibronectin) | N (5%) | PDGF/VEGF |

REFERENCE

1. HO, Tony, W.; KOPEN, Gene, C. RIGHTER, William, F.; RUTKOWSKI, J., Lynn; HERRING, W., Joseph; RAGAGLIA, Vanessa; WAGNER, Joseph, WO2003025149 A2 CELL POPULATIONS WHICH CO-EXPRESS CD49C AND CD90, NEURONYX, INC. Application No. PCT/US02/29971, Filed 20020920, A2 Published 20030327, A3 Published 20031218.

Example 2

Evaluation of Growth Media for Postpartum-Derived Cells

Several cell culture media were evaluated for their ability to support the growth of placenta-derived cells. The growth of placenta-derived cells in normal (20%) and low (5%) oxygen was assessed after 3 days using the MTS colorimetric assay.

Methods & Materials

Placenta-derived cells at passage 8 (P8) were seeded at $1\times10^3$ cells/well in 96 well plates in Growth medium (DMEM-low glucose (Gibco, Carlsbad Calif.), 15% (v/v) fetal bovine serum (Cat. #SH30070.03; Hyclone, Logan, Utah), 0.001% (v/v) betamercaptoethanol (Sigma, St. Louis, Mo.), 50 Units/milliliter penicillin, 50 micrograms/milliliter streptomycin (Gibco)). After 8 hours, the medium was changed as described in Table 2-1, and cells were incubated in normal (20%, v/v) or low (5%, v/v) oxygen at 37° C., 5% $CO_2$ for 48 hours. MTS was added to the culture medium (CELLTITER 96 AQueous One Solution Cell Proliferation Assay, Promega, Madison, Wis.) for 3 hours and the absorbance measured at 490 nanometers (Molecular Devices, Sunnyvale Calif.).

TABLE 2-1

| Culture medium | | |
|---|---|---|
| Culture Medium | Supplier | Added fetal bovine serum % (v/v) |
| DMEM-low glucose | Gibco Carlsbad CA | 0, 2, 10 |
| DMEM-high glucose | Gibco | 0, 2, 10 |
| RPMI 1640 | Mediatech, Inc. Herndon, VA | 0, 2, 10 |
| Cell gro-free (Serum-free, Protein-free) | Mediatech, Inc. | — |
| Ham's F10 | Mediatech, Inc. | 0, 2, 10 |
| MSCGM (complete with serum) | Cambrex, Walkersville, MD | 0, 2, 10 |
| Complete-serum free w/albumin | Mediatech, Inc. | — |
| Growth medium | NA | — |
| Ham's F12 | Mediatech, Inc. | 0, 2, 10 |
| Iscove's | Mediatech, Inc. | 0, 2, 10 |
| Basal Medium Eagle's | Mediatech, Inc. | 0, 2, 10 |
| DMEM/F12 (1:1) | Mediatech, Inc. | 0, 2, 10 |

Results

Standard curves for the MTS assay established a linear correlation between an increase in absorbance and an increase in cell number. The absorbance values obtained were converted into estimated cell numbers and the change (%) relative to the initial seeding was calculated.

The Effect of Serum. The addition of serum to media at normal oxygen conditions resulted in a reproducible dose-dependent increase in absorbance and thus the viable cell number. The addition of serum to complete MSCGM resulted in a dose-dependent decrease in absorbance. In the media without added serum, cells grew in Cellgro, Ham's F10, and DMEM.

The Effect of Oxygen. Reduced oxygen appeared to increase the growth rate of cells in Growth Medium, Ham's F10, and MSCGM.

In decreasing order of growth, the media resulting in the best growth of the cells were Growth medium>MSCGM>Iscove's+10% FBS=DMEM-HG+10% FBS=Ham's F12+10% FBS=RPMI 1640+10% FBS.

Summary. Postpartum-derived cells may be grown in a variety of culture media in normal or low oxygen. Short-term growth of placenta-derived cells was determined in 12 basal media with 0, 2, and 10% (v/v) serum in 5% or 20% $O_2$. In general placenta-derived cells did not grow in serum-free conditions with the exceptions of Ham's F10 and Cellgro-free, which are also protein-free. Growth in these serum-free media was approximately 25-33% of the maximal growth observed with Growth medium containing 15% serum. This study demonstrates that placenta-derived cells may be grown in serum-free conditions and that Growth medium is one of several media (10% serum in Iscove's, RPMI or Ham's F12 media) that can be used to grow placenta-derived cells.

The most promising serum-free media was CELLGRO-FREE, a serum and protein-free medium without hormones or growth factors, which is designed for the growth of mammalian cells in vitro (Mediatech product information).

Complete-serum free medium also developed for serum-free culture was not as effective in supporting growth of the placenta-derived cells. Complete-serum free was developed by Mediatech, based on a 50/50 mix of DMEM/F12 with smaller percentages of RPMI 1640 and McCoy's 5A. This medium also contains selected trace elements and high molecular weight carbohydrates, extra vitamins, a non-animal protein source, and a small amount of BSA (1 gram/liter). It does not contain any insulin, transferrin, cholesterol, or growth or attachment factors. It is bicarbonate buffered for use with 5% $CO_2$. Originally designed for hybridomas and suspension cell lines, it may be suitable for some anchorage dependent cell lines.

Example 3

Growth of Postpartum-Derived Cells in Medium Containing D-Valine

It has been reported that medium containing D-valine instead of the normal L-valine isoform can be used to selectively inhibit the growth of fibroblast-like cells in culture (Hongpaisan, 2000; Sordillo et al., 1988). The growth of postpartum-derived cells in medium containing D-valine in the absence of L-valine was evaluated.

Methods & Materials

Placenta-derived cells (P3), fibroblasts (P9), and umbilical cord-derived cells (P5) were seeded at $5 \times 10^3$ cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a Modified Growth medium (DMEM with D-valine (special order Gibco), 15% (v/v) dialyzed fetal bovine serum (Hyclone, Logan, Utah), 0.001% (v/v) beta-mercaptoethanol (Sigma), 50 Units/milliliter penicillin, 50 microgram/milliliter streptomycin (Gibco)).

Results

Placenta-derived, umbilical cord-derived, and fibroblast cells seeded in the D-valine-containing medium did not proliferate, unlike cells seeded in Growth medium containing dialyzed serum. Fibroblasts changed morphologically, increasing in size and changing shape. All of the cells died and eventually detached from the flask surface after 4 weeks.

Summary. Postpartum-derived cells require L-valine for cell growth and for long-term viability. L-valine is preferably not removed from the growth medium for postpartum-derived cells.

REFERENCES

Hongpaisan J. (2000) Inhibition of proliferation of contaminating fibroblasts by D-valine in cultures of smooth muscle cells from human myometrium. *Cell Biol Int.* 24:1-7.

Sordillo L M, Oliver S P, Akers R M. (1988) Culture of bovine mammary epithelial cells in D-valine modified medium: selective removal of contaminating fibroblasts. *Cell Biol Int Rep.* 12:355-64.

Example 4

Cryopreservation Media for Postpartum-Derived Cells

The objective of this study was to determine a suitable cryopreservation medium for the cryopreservation of postpartum-derived cells.

Methods & Materials

Placenta-derived cells grown in Growth medium (DMEM-low glucose (Gibco, Carlsbad Calif.), 15% (v/v) fetal bovine serum (Cat. #SH30070.03, Hyclone, Logan, Utah), 0.001% (v/v) betamercaptoethanol (Sigma, St. Louis, Mo.), 50 Units/milliliter penicillin, 50 microgram/milliliter streptomycin (Gibco)), in a gelatin-coated T75 flask were washed with phosphate buffered saline (PBS; Gibco) and trypsinized using 1 milliliter Trypsin/EDTA (Gibco). The trypsinization was stopped by adding 10 milliliter Growth medium. The cells were centrifuged at 150×g, supernatant removed, and the cell pellet was resuspended in 1 milliliter Growth medium. An aliquot of cell suspension, 60 microliter, was removed and added to 60 microliter □trypan blue (Sigma). The viable cell number was estimated using a hemocytometer. The cell suspension was divided into four equal aliquots each containing $88 \times 10^4$ cells each. The cell suspension was centrifuged and resuspended in 1 milliliter of each media below and transferred into Cryovials (Nalgene).

1.) Growth medium+10% (v/v) DMSO (Hybrimax, Sigma, St. Louis, Mo.)
2.) Cell Freezing medium w/DMSO, w/methylcellulose, serum-free (C6295, Sigma, St. Louis, Mo.)
3.) Cell Freezing medium serum-free (C2639, Sigma, St. Louis, Mo.)
4.) Cell Freezing Medium w/glycerol (C6039, Sigma, St. Louis, Mo.)

The cells were cooled at approximately 1° C./min overnight in a −80° C. freezer using a "Mr Frosty" freezing container according to the manufacturer's instructions (Nalgene, Rochester, N.Y.). Vials of cells were transferred into liquid nitrogen for 2 days before thawing rapidly in a 37° C. water bath. The cells were added to 10 milliliter Growth medium and centrifuged before the cell number and viability was estimated as before. Cells were seeded onto gelatin-coated flasks at 5,000 cells/cm$^2$ to determine whether the cells would attach and proliferate.

Results

The initial viability of the cells to be cryopreserved was assessed by trypan blue staining to be 100%.

There was a commensurate reduction in cell number with viability for C6295 due to cells lysis. The viable cells cryopreserved in all four solutions attached, divided, and produced a confluent monolayer within 3 days. There was no discernable difference in estimated growth rate.

Summary. The cryopreservation of cells is one procedure available for preparation of a cell bank or a cell product. Four cryopreservation mixtures were compared for their ability to protect human placenta-derived cells from freezing damage. Dulbecco's modified Eagle's medium (DMEM)

and 10% (v/v) dimethylsulfoxide (DMSO) is the preferred medium of those compared for cryopreservation of placenta-derived cells.

Example 5

Growth Characteristics of Postpartum-Derived Cells

The cell expansion potential of postpartum-derived cells was compared to other populations of isolated stem cells. The art of cell expansion to senescence is referred to as Hayflick's limit (Hayflick L. The longevity of cultured human cells. *J. Am. Geriatr. Soc.* 22(1): 1-12, 1974; Hayflick L. The strategy of senescence. *Gerontologist* 14(1):37-45), 1974). Postpartum-derived cells are highly suited for therapeutic use because they can be readily expanded to sufficient cell numbers.

Materials and Methods

Gelatin-coating flasks. Tissue culture plastic flasks were coated by adding 20 milliliter 2% (w/v) porcine gelatin (Type B: 225 Bloom; Sigma, St Louis, Mo.) to a T75 flask (Corning, Corning, N.Y.) for 20 minutes at room temperature. After removing the gelatin solution, 10 milliliter phosphate-buffered saline (PBS) (Invitrogen, Carlsbad, Calif.) were added and then aspirated.

Comparison of expansion potential of postpartum-derived cells to other cell populations. For comparison of growth expansion potential, the following cell populations were utilized: i) Mesenchymal stem cells (MSC; Cambrex, Walkersville, Md.); ii) Adipose-derived cells (U.S. Pat. No. 6,555,374 B1; U.S. Patent Application Publication No. US2004/0058412); iii) Normal dermal skin fibroblasts (cc-2509 lot #9F0844; Cambrex, Walkersville, Md.); iv) Umbilical cord-derived cells; and v) Placenta-derived cells. Cells were initially seeded at 5,000 cells/cm$^2$ on gelatin-coated T75 flasks in DMEM-Low glucose growth medium ((Invitrogen, Carlsbad, Calif.), with 15% (v/v) defined bovine serum (Hyclone, Logan, Utah; Lot #AND18475), 0.001% (v/v) 2-mercaptoethanol (Sigma, St. Louis, Mo.), 100 Units/milliliter penicillin, 100 micrograms/milliliter streptomycin, 0.25 micrograms/milliliter amphotericin B; Invitrogen, Carlsbad, Calif.). For subsequent passages, cell cultures were treated as follows. After trypsinization, viable cells were counted after Trypan Blue staining. Cell suspension (50 microliters) was combined with Trypan Blue (50 microliters, Sigma, St. Louis Mo.). Viable cell numbers were estimated using a hemocytometer.

Following counting, cells were seeded at 5,000 cells/cm$^2$ onto gelatin-coated T 75 flasks in 25 milliliter of fresh Growth medium. Cells were grown under standard atmosphere with 5% carbon dioxide at 37° C. The growth medium was changed twice per week. When cells reached about 85 percent confluence, they were passaged; this process was repeated until the cells reached senescence.

At each passage, cells were trypsinized and counted. The viable cell yield, population doubling[ln(cell final/cell initial)/ln 2] and doubling time (time in culture (h)/population doubling) were calculated. For the purposes of determining optimal cell expansion, the total cell yield per passage was determined by multiplying the total yield for the previous passage by the expansion factor for each passage (i.e., expansion factor=cell final/cell initial).

Expansion potential of cell banks at low density. The expansion potential of cells banked at passage 10 was also tested. A different set of conditions was used. Normal dermal skin fibroblasts (cc-2509 lot #9F0844; Cambrex, Walkersville, Md.), umbilical cord-derived cells, and placenta-derived cells were tested. These cell populations had been banked at passage 10 previously, having been seeded at 5,000 cells/cm$^2$ and grown to confluence at each passage to that point. The effect of cell density on the cell populations following cell thaw at passage 10 was determined. Cells were thawed under standard conditons, counted using Trypan Blue staining. Thawed cells were then seeded at 1,000 cells/cm$^2$ in Growth medium (DMEM-Low glucose (Invitrogen, Carlsbad, Calif.) with 15 percent (v/v) defined bovine serum (Hyclone, Logan, Utah; Lot #AND18475), 0.001 percent 2-mercaptoethanol (Sigma, St. Louis, Mo.), antibiotic/antimycotic (100 Units/milliliter penicillin, 100 micrograms/milliliter streptomycin, 0.25 micrograms/milliliter amphotericin B (Invitrogen, Carlsbad, Calif.)). Cells were grown under standard atmospheric conditions at 37° C. Growth medium was changed twice a week and cells were passaged as they reached about 85% confluence. Cells were subsequently passaged until senescence, i.e., until they could not be expanded any further. Cells were trypsinized and counted at each passage. The cell yield, population doubling (ln(cell final/cell initial)/ln 2) and doubling time (time in culture (h)/population doubling) were calculated. The total cell yield per passage was determined by multiplying total yield for the previous passage by the expansion factor for each passage (i.e., expansion factor=cell final/cell initial).

Expansion of postpartum-derived cells at low density from initial cell seeding. The expansion potential of freshly isolated postpartum-derived cell cultures under low cell seeding conditions was tested in another experiment. Umbilical cord- and placenta-derived cells were isolated as described herein. Cells were seeded at 1000 cells/cm$^2$ and passaged as described above until senescence. Cells were grown under standard atmospheric conditions at 37° C. Growth medium was changed twice per week. Cells were passaged as they reached about 85% confluence. At each passage, cells were trypsinized and counted by Trypan Blue staining. The cell yield, population doubling (ln(cell final/cell initial)/ln 2), and doubling time (time in culture (h)/population doubling) were calculated for each passage. The total cell yield per passage was determined by multiplying the total yield for the previous passage by the expansion factor for each passage (i.e., expansion factor=cell final/cell initial). Cells were grown on gelatin- and non-gelatin-coated flasks.

Expansion of Clonal Neonatal or Maternal Placenta-derived Cells. Cloning may be used in order to expand a population of neonatal or maternal cells successfully from placental tissue. Following isolation of three different cell populations from the placenta (neonatal aspect, maternal aspect, and villous region), these cell populations are expanded under standard growth conditions and then karyotyped to reveal the identity of the isolated cell populations. By isolating the cells from a mother who delivers a boy, it is possible to distinguish between the male and female chromosomes by performing metaphase spreads. These experiments can be used to demonstrate that top-line cells are karyotype positive for neonatal phenotype, mid-line cells are karyotype positive for both neonatal and maternal phenotypes, and bottom-line cells are karyotype positive for maternal cells.

Expansion of cells in low oxygen culture conditions. It has been demonstrated that low $O_2$ cell culture conditions can improve cell expansion in certain circumstances (Csete, Marie; Doyle, John; Wold, Barbara J.; McKay, Ron; Studer, Lorenz. Low oxygen culturing of central nervous system progenitor cells. US20040005704). In order to determine if cell expansion of postpartum-derived cells could be improved by altering cell culture conditions, cultures of umbilical cord-derived cells were grown in low oxygen conditions. Cells were seeded at 5,000 cells/cm² in Growth medium on gelatin-coated flasks. Cells were initially cultured under standard atmospheric conditions through passage 5, at which point they were transferred to low oxygen (5% $O_2$) culture conditions.

Evaluation of other growth conditions. In other experiments, postpartum-derived cells were expanded on non-coated, collagen-coated, fibronectin-coated, laminin-coated, and extracellular membrane protein (e.g., MATRIGEL (BD Discovery Labware, Bedford, Mass.))-coated plates. Cultures have been demonstrated to expand well on these different matrices.

Results

Comparison of expansion potential of postpartum-derived cells vs. other stem cell and non-stem cell populations. Both umbilical cord-derived and placenta-derived cells expanded for greater than 40 passages generating cell yields of >1E17 cells in 60 days. In contrast, MSCs and fibroblasts senesced after <25 days and <60 days, respectively. Although both adipose-derived and omental cells expanded for almost 60 days, they generated total cell yields of 4.5E12 and 4.24E13 respectively. Thus, when seeded at 5,000 cells/cm² under the experimental conditions utilized, postpartum-derived cells expanded much better than the other cell types grown under the same conditions (Table 5-1).

Expansion of potential of cell banks at low density. Umbilical cord-derived, placenta-derived, and fibroblast cells expanded for greater than 10 passages generating cell yields of >1E11 cells in 60 days (Table 5-2). After 60 days under these conditions, the fibroblasts became senescent, whereas the umbilical cord-derived and placenta-derived cell populations senesced after 80 days, completing >50 and >40 population doublings, respectively.

Expansion of postpartum-derived cells at low density from initial cell seeding. Postpartum-derived cells were seeded at low density (1,000 cells/cm²) on gelatin-coated and uncoated plates or flasks. Growth potential of these cells under these conditions was good. The cells expanded readily in a log phase growth. The rate of cell expansion was similar to that observed when postpartum-derived cells were seeded at 5,000 cells/cm² on gelatin-coated flasks in Growth medium. No differences were observed in cell expansion potential between culturing on either uncoated flasks or gelatin-coated flasks. However, cells appeared phenotypically much smaller on gelatin-coated flasks, and more, larger cell phenotypes were observed on uncoated flasks.

Expansion of Clonal Neonatal or Maternal Placenta-Derived Cells. A clonal neonatal or maternal cell population can be expanded from placenta-derived cells isolated from the neonatal aspect or the maternal aspect, respectively, of the placenta. Cells are serially diluted and then seeded onto gelatin-coated plates in Growth medium for expansion at 1 cell/well in 96-well gelatin coated plates. From this initial cloning, expansive clones are identified, trypsinized, and reseeded in 12-well gelatin-coated plates in Growth medium and then subsequently passaged into T25 gelatin-coated flasks at 5,000 cells/cm² in Growth medium. Subcloning is performed to ensure that a clonal population of cells has been identified. For subcloning experiments, cells are trypsinized and reseeded at 0.5 cells/well. The subclones that grow well are expanded in gelatin-coated T25 flasks at 5,000 cells cm²/flask. Cells are passaged at 5,000 cells cm²/T75 flask. The growth characteristics of a clone may be plotted to demonstrate cell expansion. Karyotyping analysis can confirm that the clone is either neonatal or maternal.

Expansion of cells in low oxygen culture conditions. Postpartum-derived cells expanded well under the reduced oxygen conditions. Culturing under low oxygen conditions does not appear to have a significant effect on cell expansion for postpartum-derived cells. Standard atmospheric conditions have already proven successful for growing sufficient numbers of cells, and low oxygen culture is not required for the growth of postpartum-derived cells.

Summary. Commercially viable cell products must be able to be produced in sufficient quantities to provide therapeutic treatment to patients in need of the treatment. Postpartum-derived cells can be expanded in culture for such purposes. Comparisons were made of the growth of postpartum-derived cells in culture to that of other cell populations including mesenchymal stem cells. The data demonstrated that postpartum-derived cell lines as developed herein can expand for greater than 40 doublings to provide sufficient cell numbers, for example, for pre-clinical banks. Furthermore, these postpartum-derived cell populations can be expanded well at low or high density. This study has demonstrated that mesenchymal stem cells, in contrast, cannot be expanded to obtain large quantities of cells.

The current cell expansion conditions of growing isolated postpartum-derived cells at densities of about 5,000 cells/cm² in Growth medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1,000 cells/cm²). Postpartum-derived cell expansion in low oxygen conditions also facilitates cell expansion, although no incremental improvement in cell expansion potential has yet been observed when utilizing these conditions for growth. Presently, culturing postpartum-derived cells under standard atmospheric conditions is preferred for generating large pools of cells. However, when the culture conditions are altered, postpartum-derived cell expansion can likewise be altered. This strategy may be used to enhance the proliferative and differentiative capacity of these cell populations.

Under the conditions utilized, while the expansion potential of MSC and adipose-derived cells is limited, postpartum-derived cells expand readily to large numbers.

REFERENCES

1) Hayflick L. The longevity of cultured human cells. *J Am Geriatr Soc.* 1974 January;22(1): 1-12.
2) Hayflick L. The strategy of senescence. *Gerontologist.* 1974 February;14(1):37-45.
3) Patent US20040058412
4) Patent US20040048372
6) Csete, Marie; (Ann Arbor, Mich.); Doyle, John; (South Pasadena, Calif.); Wold, Barbara J.; (San Marino, Calif.); McKay, Ron; (Bethesda, Md.); Studer, Lorenz; (New York, N.Y.). Low oxygen culturing of central nervous system progenitor cells. US20040005704.

TABLE 5-1

Growth characteristics for different cell populations grown to senescence

| Cell Type | Senescence | Total Population Doublings | Total Cell Yield |
| --- | --- | --- | --- |
| MSC | 24 days | 8 | 4.72 E7 |
| Adipose-derived cells | 57 days | 24 | 4.5 E12 |

TABLE 5-1-continued

Growth characteristics for different cell populations grown to senescence

| Cell Type | Senescence | Total Population Doublings | Total Cell Yield |
|---|---|---|---|
| (Artecel, U.S. Pat. No. 6,555,374) Fibroblasts | 53 days | 26 | 2.82 E13 |
| Umbilical cord-derived cells | 65 days | 42 | 6.15 E17 |
| Placenta-derived cells | 80 days | 46 | 2.49 E19 |

TABLE 5-2

Growth characteristics for different cell populations using low density growth expansion from passage 10 to senescence

| Cell Type | Senescence | Total Population Doublings | Total Cell Yield |
|---|---|---|---|
| Fibroblast (P10) | 80 days | 43.68 | 2.59 E11 |
| Umbilical cord-derived cells (P10) | 80 days | 53.6 | 1.25 E14 |
| Placenta-derived cells (P10) | 60 days | 32.96 | 6.09 E12 |

Example 6

Karyotype Analysis of PPDCs

Cell lines used in cell therapy are preferably homogeneous and free from any contaminating cell type. Human cells used in cell therapy should have a normal chromosome number (46) and structure. To identify postpartum-derived placental and umbilical cord cell lines that are homogeneous and free from cells of non-postpartum tissue origin, karyotypes of cell samples were analyzed.

Materials and Methods

PPDCs from postpartum tissue of a male neonate were cultured in Growth medium (DMEM-low glucose (Gibco Carlsbad, Calif.), 15% (v/v) fetal bovine serum (FBS) (Hyclone, Logan, Utah), 0.001% (v/v) betamercaptoethanol (Sigma, St. Louis, Mo.), and 50 Units/milliliter penicillin, 50 micrograms/milliliter streptomycin (Gibco, Carlsbad, Calif.)). Postpartum tissue from a male neonate (X, Y) was selected to allow distinction between neonatal-derived cells and maternal-derived cells (X, X). Cells were seeded at 5,000 cells per square centimeter in Growth medium in a T25 flask (Corning, Corning, N.Y.) and expanded to about 80% confluence. A T25 flask containing cells was filled to the neck with Growth medium. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted by the cytogenetics laboratory staff as exhibiting a normal appearance. Three of the sixteen cell lines analyzed exhibited a heterogeneous phenotype (XX and XY) indicating the presence of cells derived from both neonatal and maternal origins (Table 6-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin.

TABLE 6-1

Karyotype results of PPDCs.

| Tissue | passage | Metaphase cells counted | Metaphase cells analyzed | Number of karyotypes | ISCN Karyotype |
|---|---|---|---|---|---|
| Placenta | 22 | 20 | 5 | 2 | 46, XX |
| Umbilical | 23 | 20 | 5 | 2 | 46, XX |
| Umbilical | 6 | 20 | 5 | 2 | 46, XY |
| Placenta | 2 | 20 | 5 | 2 | 46, XX |
| Umbilical | 3 | 20 | 5 | 2 | 46, XX |
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-N C1 | 1 | 20 | 5 | 2 | 46, XY |
| Placenta-N C3 | 1 | 20 | 6 | 4 | 46, XY[2]/46, XX[18] |
| Placenta-N C4 | 1 | 20 | 5 | 2 | 46, XY |
| Placenta-N C15 | 1 | 20 | 5 | 2 | 46, XY |
| Placenta-N C20 | 1 | 20 | 5 | 2 | 46, XY |
| Placenta-N C22 | 1 | 20 | 5 | 2 | 46, XY |

Key: N- Neonatal side; V- villous region; M- maternal side; C- clone

Summary. Chromosome analysis identified placenta- and umbilical cord-derived PPDCs whose karyotypes appear normal as interpreted by a clinical cytogenetic laboratory. Karyotype analysis also identified cell lines free from maternal cells, as determined by homogeneous karyotype.

Example 7

Evaluation of Human Postpartum-Derived Cell Surface Markers by Flow Cytometry

Characterization of cell surface proteins or "markers" by flow cytometry can be used to determine a cell line's identity. The consistency of expression can be determined from multiple donors, and in cells exposed to different processing and culturing conditions. Postpartum-derived cell lines isolated from the placenta and umbilical cord were characterized by flow cytometry, thereby providing a profile for the identification of the cells of the invention.

Materials and Methods

Media. Cells were cultured in DMEM-low glucose Growth medium (Gibco Carlsbad, Calif.), with 15% (v/v) fetal bovine serum (FBS); (Hyclone, Logan, Utah), 0.001%

(v/v) betamercaptoethanol (Sigma, St. Louis, Mo.), and 50 Units/milliliter penicillin, 50 micrograms/milliliter streptomycin (Gibco, Carlsbad, Calif.).

Culture Vessels. Cells were cultured in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Antibody Staining. Adherent cells in flasks were washed in phosphate buffered saline (PBS); (Gibco, Carlsbad, Calif.) and detached with Trypsin/EDTA (Gibco, Carlsbad, Calif.). Cells were harvested, centrifuged, and resuspended in 3% (v/v) FBS in PBS at a cell concentration of $1 \times 10^7$ per milliliter. In accordance with the manufacturer's specifications, antibody to the cell surface marker of interest (Table 7-1) was added to one hundred microliters of cell suspension and the mixture was incubated in the dark for 30 minutes at 4° C. After incubation, cells were washed with PBS and centrifuged to remove unbound antibody. Cells were resuspended in 500 microliter PBS and analyzed by flow cytometry.

Flow Cytometry Analysis. Flow cytometry analysis was performed with a FACScalibur instrument (Becton Dickinson, San Jose, Calif.).

Antibodies to Cell Surface Markers. The following antibodies to cell surface markers were used.

TABLE 7-1

Antibodies to Cell Surface markers

| Antibody | Manufacture | Catalog Number |
|---|---|---|
| CD10 | BD Pharmingen (San Diego, CA) | 555375 |
| CD13 | BD Pharmingen (San Diego, CA) | 555394 |
| CD31 | BD Pharmingen (San Diego, CA) | 555446 |
| CD34 | BD Pharmingen (San Diego, CA) | 555821 |
| CD44 | BD Pharmingen (San Diego, CA) | 555478 |
| CD45RA | BD Pharmingen (San Diego, CA) | 555489 |
| CD73 | BD Pharmingen (San Diego, CA) | 550257 |
| CD90 | BD Pharmingen (San Diego, CA) | 555596 |
| CD117 | BD Biosciences (San Jose, CA) | 340529 |
| CD141 | BD Pharmingen (San Diego, CA) | 559781 |
| PDGFr-alpha | BD Pharmingen (San Diego, CA) | 556002 |
| HLA-A, B, C | BD Pharmingen (San Diego, CA) | 555553 |
| HLA-DR, DP, DQ | BD Pharmingen (San Diego, CA) | 555558 |
| IgG-FITC | Sigma (St. Louis, MO) | F-6522 |
| IgG-PE | Sigma (St. Louis, MO) | P-4685 |

Placenta- and Umbilical Cord-Derived Cell Comparison. Placenta-derived cells were compared to umbilical cord-derived cells at passage 8.

Passage to Passage Comparison. Placenta- and umbilical cord cells were analyzed at passages 8, 15, and 20.

Donor to Donor Comparison. To compare differences among donors, placenta-derived cells from different donors were compared to each other, and umbilical cord-derived cells from different donors were compared to each other.

Surface Coating Comparison. Placenta-derived cells cultured on gelatin-coated flasks were compared to placenta-derived cells cultured on uncoated flasks. Umbilical cord-derived cells cultured on gelatin-coated flasks were compared to umbilical cord-derived cells cultured on uncoated flasks.

Digestion Enzyme Comparison. Four treatments used for isolation and preparation of cells were compared. Cells derived from postpartum tissue by treatment with 1) collagenase; 2) collagenase/dispase; 3) collagenase/hyaluronidase; and 4) collagenase/hyaluronidase/dispase were compared.

Placental Layer Comparison. Cells isolated from the maternal aspect of placental tissue were compared to cells isolated from the villous region of placental tissue and cells isolated from the neonatal fetal aspect of placenta.

Results

Placenta-derived cells were compared to Umbilical cord-derived cells. Placenta- and umbilical cord-derived cells analyzed by flow cytometry showed positive for production of CD10, CD13, CD44, CD73, CD 90, PDGFr-alpha and HLA-A, B, C, indicated by the increased values of fluorescence relative to the IgG control. These cells were negative for detectable expression of CD31, CD34, CD45, CD117, CD141, and HLA-DR, DP, DQ, indicated by fluorescence values comparable to the IgG control. Variations in fluorescence values of positive curves was accounted. The mean (i.e., CD13) and range (i.e., CD90) of the positive curves showed some variation, but the curves appeared normal, confirming a homogeneous population. Both curves individually exhibited values greater than the IgG control.

Passage to Passage Comparison of Placenta-derived cells. Placenta-derived cells at passages 8, 15, and 20 analyzed by flow cytometry all were positive for production of CD10, CD13, CD44, CD73, CD 90, PDGFr-alpha and HLA-A, B, C, as reflected in the increased value of fluorescence relative to the IgG control. The cells were negative for production of CD31, CD34, CD45, CD117, CD141, and HLA-DR, DP, DQ having fluorescence values consistent with the IgG control.

Passage to Passage Comparison of Umbilical cord-derived cells. Umbilical cord-derived cells at passage 8, 15, and 20 analyzed by flow cytometry all expressed CD10, CD13, CD44, CD73, CD 90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Donor to Donor Comparison of Placenta-derived cells. Placenta-derived cells isolated from separate donors analyzed by flow cytometry each expressed CD10, CD13, CD44, CD73, CD 90, PDGFr-alpha and HLA-A, B, C, with increased values of fluorescence relative to the IgG control. The cells were negative for production of CD31, CD34, CD45, CD117, CD141, and HLA-DR, DP, DQ as indicated by fluorescence value consistent with the IgG control.

Donor to Donor Comparison of Umbilical cord-derived cells. Umbilical cord-derived cells isolated from separate donors analyzed by flow cytometry each showed positive for production of CD10, CD13, CD44, CD73, CD 90, PDGFr-alpha and HLA-A, B, C, reflected in the increased values of fluorescence relative to the IgG control. These cells were negative for production of CD31, CD34, CD45, CD117, CD141, and HLA-DR, DP, DQ with fluorescence values consistent with the IgG control.

The Effect of Surface Coating with Gelatin on Placenta-derived Cells. Placenta-derived cells expanded on either gelatin-coated or uncoated flasks analyzed by flow cytometry all expressed of CD10, CD13, CD44, CD73, CD 90, PDGFr-alpha and HLA-A, B, C, reflected in the increased values of fluorescence relative to the IgG control. These cells were negative for production of CD31, CD34, CD45, CD117, CD141, and HLA-DR, DP, DQ indicated by fluorescence values consistent with the IgG control.

The Effect of Surface Coating with Gelatin on Umbilical cord-derived Cells. Umbilical cord-derived cells expanded on gelatin and uncoated flasks analyzed by flow cytometry all were positive for production of CD10, CD13, CD44, CD73, CD 90, PDGFr-alpha and HLA-A, B, C, with increased values of fluorescence relative to the IgG control. These cells were negative for production of CD31, CD34, CD45, CD117, CD141, and HLA-DR, DP, DQ, with fluorescence values consistent with the IgG control.

Evaluation of Effect of Enzyme Digestion Procedure Used for Preparation and Isolation of the Cells on the Cell Surface Marker Profile. Placenta-derived cells isolated using various digestion enzymes analyzed by flow cytometry all expressed CD10, CD13, CD44, CD73, CD 90, PDGFr-alpha and HLA-A, B, C, as indicated by the increased values of fluorescence relative to the IgG control. These cells were negative for production of CD31, CD34, CD45, CD117, CD141, and HLA-DR, DP, DQ as indicated by fluorescence values consistent with the IgG control.

Placental Layer Comparison. Cells derived from the maternal, villous, and neonatal layers of the placenta, respectively, analyzed by flow cytometry showed positive for production of CD10, CD13, CD44, CD73, CD90, PDGFr-alpha and HLA-A, B, C, as indicated by the increased value of fluorescence relative to the IgG control. These cells were negative for production of CD31, CD34, CD45, CD117, CD141, and HLA-DR, DP, DQ as indicated by fluorescence values consistent with the IgG control.

Summary. Analysis of placenta- and umbilical cord-derived postpartum cells by flow cytometry has established of an identity of these cell lines. Placenta- and umbilical cord-derived postpartum cells are positive for CD10, CD13, CD44, CD73, CD90, PDGFr-alpha, HLA-A,B,C and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogeneous population which has positive expression of the markers.

Example 8

Analysis of Postpartum Tissue-Derived Cells by Affymetrix GeneChip® Arrays

Affymetrix GeneChip® arrays were used to compare gene expression profiles of umbilical cord- and placenta-derived cells with fibroblasts, human mesenchymal stem cells, and another cell line derived from human bone marrow. This analysis provided a characterization of the postpartum-derived cells and identified unique molecular markers for these cells.

Materials and Methods

Isolation and Culture of Cells

Postpartum tissue-derived cells. Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth medium (Dulbecco's Modified Essential Media (DMEM-low glucose; Invitrogen, Carlsbad, Calif.) with 15% (v/v) fetal bovine serum (Hyclone, Logan Utah), 100 Units/milliliter penicillin, 100 micrograms/milliliter streptomycin (Invitrogen, Carlsbad, Calif.), and 0.001% (v/v) 2-mercaptoethanol (Sigma, St. Louis Mo.)) on gelatin-coated tissue culture plastic flasks. The cultures were incubated at 37° C. in standard atmosphere.

Fibroblasts. Human dermal fibroblasts were purchased from Cambrex Incorporated (Walkersville, Md.; Lot number 9F0844) and were obtained from ATCC CRL-1501 (CCD39SK). Both lines were cultured in DMEM/F12 medium (Invitrogen, Carlsbad, Calif.) with 10% (v/v) fetal bovine serum (Hyclone) and 100 Units/milliliter penicillin, 100 micrograms/milliliter streptomycin (Invitrogen). The cells were grown on standard tissue-treated plastic.

Human Mesenchymal Stem Cells (hMSC). hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human Iliac Crest Bone Marrow Cells (ICBM). Human iliac crest bone marrow was received from NDRI with patient consent. The marrow was processed according to the method outlined by Ho, et al. (WO03/025149). The marrow was mixed with lysis buffer (155 micromolar $NH_4Cl$, 10 micromolar $KHCO_3$, and 0.1 micromolar EDTA, pH 7.2) at a ratio of 1 part bone marrow to 20 parts lysis buffer. The cell suspension was vortexed, incubated for 2 minutes at ambient temperature, and centrifuged for 10 minutes at 500 x g. The supernatant was discarded and the cell pellet was resuspended in Minimal Essential Medium-alpha (Invitrogen) supplemented with 10% (v/v) fetal bovine serum and 4 micromolar glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at $5 \times 10^4$ cells/cm$^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Isolation of mRNA and Gene Chip Analysis. Actively growing cultures of cells were removed from the flasks with a cell scraper in cold phosphate buffered saline (PBS). The cells were centrifuged for 5 minutes at 300 x g. The supernatant was removed and the cells were resuspended in fresh PBS and centrifuged again. The supernatant was removed and the cell pellet was immediately frozen and stored at −80° C. Cellular mRNA was extracted and transcribed into cDNA. cDNA was then transcribed into cRNA and biotin-labeled. The biotin-labeled cRNA was hybridized with HG-U133A GENECHIP oligonucleotide array (Affymetrix, Santa Clara Calif.). The hybridization and data collection was performed according to the manufacturer's specifications. Analyses were performed using "Significance Analysis of Microarrays" (SAM) version 1.21 computer software (Stanford University; Tusher, V. G. et al., 2001, Proc. Natl. Acad. Sci. USA 98: 5116-5121).

Results

Fourteen different populations of cells were analyzed in this study. The cells along with passage information, culture substrate, and culture media are listed in Table 8-1.

TABLE 8-1

Cells analyzed by the microarray study. The cells lines are listed by their identification code along with passage at the time of analysis, cell growth substrate, and growth media.

| Cell Population | Passage | Substrate | Media |
|---|---|---|---|
| Umbilical (022803) | 2 | Gelatin | DMEM, 15% FBS, BME |

TABLE 8-1-continued

Cells analyzed by the microarray study. The cells lines are listed by their identification code along with passage at the time of analysis, cell growth substrate, and growth media.

| Cell Population | Passage | Substrate | Media |
|---|---|---|---|
| Umbilical (042103) | 3 | Gelatin | DMEM, 15% FBS, BME |
| Umbilical (071003) | 4 | Gelatin | DMEM, 15% FBS, BME |
| Placenta (042203) | 12 | Gelatin | DMEM, 15% FBS, BME |
| Placenta (042903) | 4 | Gelatin | DMEM, 15% FBS, BME |
| Placenta (071003) | 3 | Gelatin | DMEM, 15% FBS, BME |
| ICBM (070203) (5% $O_2$) | 3 | Plastic | MEM 10% FBS |
| ICBM (062703) (std $O_2$) | 5 | Plastic | MEM 10% FBS |
| ICBM (062703)(5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (ATCC CRL-1501) | 4 | Plastic | DMEM-F12, 10% FBS |

The data were evaluated by a Principle Component Analysis, analyzing the 290 genes that were differentially expressed in the cells. This analysis allows for a relative comparison for the similarities between the populations. Table 8-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 8-2

The Euclidean Distances for the Cell Pairs. The Euclidean distance was calculated for the cell types using the 290 genes that were differentially expressed between the cell types. Similarity between the cells is inversely proportional to the Euclidean distance.

| Cell Pair | Euclidean Distance |
|---|---|
| ICBM-hMSC | 24.71 |
| Placenta-umbilical | 25.52 |
| ICBM-Fibroblast | 36.44 |
| ICBM-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 8-3, 8-4, and 8-5 show the expression of genes increased in placenta-derived cells (Table 8-3), increased in umbilical cord-derived cells (Table 8-4), and reduced in umbilical cord- and placenta-derived cells (Table 8-5). The column entitled "Probe Set ID" refers to the manufacturer's identification code for the sets of several oligonucleotide probes located on a particular site on the chip, which hybridize to the named gene (column "Gene Name"), comprising a sequence that can be found within the NCBI (GENBANK) database at the specified accession number (column "NCBI Accession Number").

TABLE 8-3

Genes shown to have specifically increased expression in the placenta-derived cells as compared to the other cell lines assayed.
Genes Increased in Placenta-Derived Cells

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | renin | NM_000537 |
| 210004_at | oxidised low density lipoprotein (lectin-like) receptor 1 | AF035776 |
| 214993_at | Homo sapiens, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | Homo sapiens mRNA; cDNA DKFZp547K1113 (from clone DKFZp547K1113) | AI246730 |

TABLE 8-4

Genes shown to have specifically increased expression in umbilical cord-derived cells as compared to the other cell lines assayed.
Genes Increased in Umbilical Cord-Derived Cells

| Probe Set ID | Gene Name | NCBI Accession Number |
|---|---|---|
| 202859_x_at | interleukin 8 | NM_000584 |
| 211506_s_at | interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 8-5

Genes that were shown to have decreased expression in the umbilical cord- and placenta-derived cells as compared to the other cell lines assayed.
Genes Decreased in Umbilical Cord- and Placenta-Derived Cells

| Probe Set ID | Gene name | NCBI Accession Number |
|---|---|---|
| 210135_s_at | short stature homeobox 2 | AF022654.1 |
| 205824_at | heat shock 27 kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |

TABLE 8-5-continued

Genes that were shown to have decreased expression in the umbilical cord- and placenta-derived cells as compared to the other cell lines assayed.
Genes Decreased in Umbilical Cord- and Placenta-Derived Cells

| Probe Set ID | Gene name | NCBI Accession Number |
|---|---|---|
| 206201_s_at | mesenchyme homeobox 2 (growth arrest-specific homeobox) | NM_005924.1 |
| 205817_at | sine oculis homeobox homolog 1 (*Drosophila*) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (*Drosophila*) | NM_003507.1 |
| 212736_at | hypothetical gene BC008967 | BE299456 |
| 214587_at | collagen, type VIII, alpha 1 | BE877796 |
| 201645_at | tenascin C (hexabrachion) | NM_002160.1 |
| 210239_at | iroquois homeobox protein 5 | U90304.1 |
| 203903_s_at | hephaestin | NM_014799.1 |
| 205816_at | integrin, beta 8 | NM_002214.1 |
| 203069_at | synaptic vesicle glycoprotein 2 | NM_014849.1 |
| 213909_at | *Homo sapiens* cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (*Drosophila*) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | biglycan | AA845258 |
| 201261_x_at | biglycan | BC002416.1 |
| 202132_at | transcriptional co-activator with PDZ-binding motif (TAZ) | AA081084 |
| 214701_s_at | fibronectin 1 | AJ276395.1 |
| 213791_at | proenkephalin | NM_006211.1 |
| 205422_s_at | integrin, beta-like 1 (with EGF-like repeat domains) | NM_004791.1 |
| 214927_at | *Homo sapiens* mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | *Homo sapiens* mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36 kDa | NM_000597.1 |

Tables 8-6, 8-7, and 8-8 show the expression of genes increased in human fibroblasts (Table 8-6), ICBM cells (Table 8-7), and MSCs (Table 8-8).

TABLE 8-6

Genes that were shown to have increased expression in fibroblasts as compared to the other cell lines assayed.
Genes increased in fibroblasts dual specificity phosphatase 2
KIAA0527 protein
*Homo sapiens* cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
*Homo sapiens* cDNA: FLJ23564 fis, clone LNG10773
*Homo sapiens* mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [*Homo sapiens*]
transforming growth factor, beta 2
hypothetical protein MGC29643
antigen identified by monoclonal antibody MRC OX-2

TABLE 8-7

Genes that were shown to have increased expression in the ICBM-derived cells as compared to the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine: polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1

TABLE 8-7-continued

Genes that were shown to have increased expression in the ICBM-derived cells as compared to the other cell lines assayed. Genes Increased In ICBM Cells jagged 1 (Alagille syndrome)
proteoglycan 1, secretory granule

TABLE 8-8

Genes that were shown to have increased expression in the MSC cells as compared to the other cell lines assayed. Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
Homo sapiens cDNA FLJ12232 fis, clone MAMMA1001206
Homo sapiens cDNA FLJ34668 fis, clone LIVER2000775
jun B proto-oncogene
B-cell CLL/lymphoma 6 (zinc finger protein 51)
zinc finger protein 36, C3H type, homolog (mouse)

Summary The GENECHIP analysis was performed to provide a molecular characterization of the postpartum cells derived from umbilical cord and placenta. This analysis included cells derived from three different umbilical cords and three different placentas. The study also included two different lines of dermal fibroblasts, three lines of mesenchymal stem cells, and three lines of iliac crest bone marrow cells. The mRNA that was expressed by these cells was analyzed by AffyMetrix GENECHIP that contained oligonucleotide probes for 22,000 genes.

Results showed that 290 genes are differentially expressed in these five different cell types. These genes include ten genes that are specifically increased in the placenta-derived cells and seven genes specifically increased in the umbilical cord-derived cells. Fifty-four genes were found to have specifically lower expression levels in placenta and umbilical cord.

The expression of selected genes has been confirmed by PCR in Example 9. These results demonstrate that the postpartum-derived cells have a distinct gene expression profile, for example, as compared to bone marrow-derived cells and fibroblasts.

REFERENCE

Lockhart et al., Expression monitoring by hybridization to high-density oligonucleotide arrays. *Nat. Biotechnol.* 1996, 14(13):1675-1680.

Example 9

Cell Markers in Postpartum-Derived Cells

Similarities and differences in cells derived from the human placenta and the human umbilical cord were assessed by comparing their gene expression profiles with those of cells derived from other sources (using an Affymetrix GENECHIP array). Six "signature" genes were identified: oxidized LDL receptor 1, interleukin-8, renin, reticulon, chemokine receptor ligand 3 (CXC ligand 3), and granulocyte chemotactic protein 2 (GCP-2). These "signature" genes were expressed at relatively high levels in postpartum-derived cells.

The present studies were conducted to verify the microarray data and to identify accordance/discordance between gene and protein expression, as well as to establish a series of reliable assays for detection of unique identifiers for placenta- and umbilical cord-derived cells.

Methods & Materials

Cells. Placenta-derived cells (three isolates, including one isolate predominately neonatal as identified by karyotyping analysis), umbilical cord-derived cells (four isolates), and Normal Human Dermal Fibroblasts (NHDF; neonatal and adult) were grown in Growth medium (DMEM-low glucose (Gibco, Carlsbad, Calif.), 15% (v/v) fetal bovine serum (Cat. #SH30070.03; Hyclone, Logan, Utah), 0.001% (v/v) beta-mercaptoethanol (Sigma, St. Louis, Mo.), 50 Units/milliliter penicillin, 50 micrograms/milliliter streptomycin (Gibco, Carlsbad, Calif.) in a gelatin-coated T75 flask. Mesenchymal Stem Cells (MSCs) were grown in Mesenchymal Stem Cell Growth Medium Bullet kit (MSCGM; Cambrex, Walkerville, Md.).

For the IL-8 secretion experiment, cells were thawed from liquid nitrogen and plated in gelatin-coated flasks at 5,000 cells/cm$^2$, grown for 48 hours in Growth medium, and then grown for an additional 8 hours in 10 milliliter of serum starvation medium (DMEM-low glucose (Gibco, Carlsbad, Calif.), 50 Units/milliliter penicillin, 50 micrograms/milliliter streptomycin (Gibco, Carlsbad, Calif.), and 0.1% (w/v) Bovine Serum Albumin (BSA; Sigma, St. Louis, Mo.)). After this treatment, RNA was extracted and the supernatants were centrifuged at 150×g for 5 minutes to remove cellular debris. Supernatants were then frozen at −80° C. for ELISA analysis.

Cell culture for ELISA assay. Postpartum cells derived from placenta and umbilical cord, as well as human fibroblasts derived from human neonatal foreskin, were cultured in Growth medium in gelatin-coated T75 flasks. Cells were frozen at passage 11 in liquid nitrogen. Cells were thawed and transferred to 15 milliliter centrifuge tubes. After centrifugation at 150×g for 5 minutes, the supernatant was discarded. Cells were resuspended in 4 milliliter culture medium and counted. Cells were grown in a 75 cm$^2$ flask containing 15 milliliter of Growth medium at 375,000 cell/flask for 24 hours. The medium was changed to a serum starvation medium for 8 hours. Serum starvation medium was collected at the end of incubation, centrifuged at 14,000×g for 5 minutes, and stored at −20° C.

To estimate the number of cells in each flask, 2 milliliter of tyrpsin/EDTA (Gibco, Carlsbad, Calif.) was added to each flask. After cells detached from the flask, trypsin activity was neutralized with 8 milliliter of Growth medium. Cells were transferred to a 15 milliliter centrifuge tube and centrifuged at 150×g for 5 minutes. Supernatant was removed, and 1 milliliter Growth medium was added to each tube to resuspend the cells. Cell number was estimated using a hemocytometer.

ELISA assay. The amount of IL-8 secreted by the cells into serum starvation medium was analyzed using ELISA assays (R&D Systems, Minneapolis, Minn.). All assays were tested according to the instructions provided by the manufacturer.

Total RNA isolation. RNA was extracted from confluent postpartum-derived cells and fibroblasts or for IL-8 expression from cells treated as described above. Cells were lysed with 350 microliter buffer RLT containing beta-mercaptoethanol (Sigma, St. Louis, Mo.) and RNA was extracted using an RNA purification mini kit sold under the trademark RNEASY according to the manufacturer's instructions (RNEASY Mini Kit; Qiagen, Valencia, Calif.) and subjected to DNase treatment (2.7 U/sample) (Sigma St. Louis, Mo.). RNA was eluted with 50 microliter DEPC-treated water and stored at −80° C. RNA was also extracted from human placenta and umbilical cord. Tissue (30 milligram) was suspended in 700 microliter of buffer RLT containing beta-mercaptoethanol. Samples were mechanically homogenized, and the RNA extraction proceeded according to manufacturer's specification. RNA was extracted with 50 microliter of DEPC-treated water and stored at −80° C.

Reverse transcription. RNA was reversed transcribed using random hexamers with the TaqMan® reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum-derived cells (signature genes—including oxidized LDL receptor, interleukin-8, renin, and reticulon), were further investigated using real-time and conventional PCR.

Real-time PCR. PCR was performed on cDNA samples using ASSAYS-ON-DEMAND gene expression products: oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH were mixed with cDNA and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 minutes and 95° C. for 10 min, followed by 40 cycles of 95° C. for 15 seconds and 60° C. for 1 minute. PCR data was analyzed according to manufacturer's specifications (User Bulletin #2 from Applied Biosystems for ABI Prism 7700 Sequence Detection System).

Conventional PCR. Conventional PCR was performed using an ABI PRISM 7700 (Perkin Elmer Applied Biosystems, Boston, Mass.) to confirm the results from real-time PCR. PCR was performed using 2 microliter of cDNA solution, 1×TAQ polymerase (tradename AMPLITAQ GOLD) universal mix PCR reaction buffer (Applied Biosystems, Foster City, Calif.), and initial denaturation at 94° C. for 5 minutes. Amplification was optimized for each primer set: for IL-8, CXC ligand 3, and reticulon (94° C. for 15 seconds, 55° C. for 15 seconds and 72° C. for 30 seconds for 30 cycles); for renin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 1. Primer concentration in the final PCR reaction was 1 micromolar except for GAPDH which was 0.5 micromolar. GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length POLAROID camera (VWR International, South Plainfield, N.J.).

TABLE 9-1

Primers used

| Primer name | Primers | |
|---|---|---|
| Oxidized LDL receptor | S: 5'-GAGAAATCCAAAGAGCAAATGG-3' | (SEQ ID NO: 1) |
| | A: 5'-AGAATGGAAAACTGGAATAGG-3' | (SEQ ID NO: 2) |
| Renin | S: 5'-TCTTCGATGCTTCGGATTCC-3' | (SEQ ID NO: 3) |
| | A: 5'-GAATTCTCGGAATCTCTGTTG-3' | (SEQ ID NO: 4) |
| Reticulon | S: 5'- TTACAAGCAGTGCAGAAAACC-3' | (SEQ ID NO: 5) |
| | A: 5'- AGTAAACATTGAAACCACAGCC-3' | (SEQ ID NO: 6) |
| Interleukin-8 | S: 5'- TCTGCAGCTCTGTGTGAAGG-3' | (SEQ ID NO: 7) |
| | A: 5'-CTTCAAAAACTTCTCCACAACC-3' | (SEQ ID NO: 8) |
| Chemokine (CXC) ligand 3 | S: 5'-CCCACGCCACGCTCTCC-3' | (SEQ ID NO: 9) |
| | A: 5'-TCCTGTCAGTTGGTGCTCC-3' | (SEQ ID NO: 10) |

Immunofluorescence. Postpartum-derived cells were fixed with cold 4% (w/v) paraformaldehyde (Sigma-Aldrich, St. Louis, Mo.) for 10 minutes at room temperature. One isolate each of umbilical cord- and placenta-derived cells at passage 0 (P0) (directly after isolation) and passage 11 (P11) (two isolates of Placenta-derived, two isolates of Umbilical cord-derived cells) and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Calif.—raised against mouse,), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum-derived cells: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the process. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution (no 1° control). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of cells for FACS analysis. Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1 \times 10^7$/milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per manufacturer's specifications, and the cells were incubated for in the dark for 30 minutes at 4° C. After incubation, cells were washed with PBS and centrifuged to remove excess antibody. Cells requiring a secondary antibody were resuspended in 100 microliter of 3% FBS. Secondary antibody was added as per manufacturer's specification, and the cells were incubated in the dark for 30 minutes at 4° C. After incubation, cells were washed with PBS and centrifuged to remove excess secondary antibody. Washed cells were resuspended in 0.5 milliliter PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), and Donkey against Goat IgG (sc-3743; Santa Cruz, Biotech.).

FACS analysis. Flow cytometry analysis was performed with FACScalibur (Becton Dickinson San Jose, Calif.).

Results

Results of real-time PCR for selected "signature" genes performed on cDNA from cells derived from human placentas, adult and neonatal fibroblasts, and Mesenchymal Stem Cells (MSCs) indicate that both oxidized LDL receptor and renin were expressed at higher level in the placenta-derived cells as compared to other cells. The data obtained from real-time PCR were analyzed by the ΔΔCT method and expressed on a logarithmic scale. Levels of reticulon and oxidized LDL receptor expression were higher in umbilical cord-derived cells as compared to other cells. No significant difference in the expression levels of CXC ligand 3 and GCP-2 were found between postpartum-derived cells and controls (data not shown). CXC-ligand 3 was expressed at very low levels. GCP-2 was expressed at levels comparable to human adult and neonatal fibroblasts. The results of real-time PCR were confirmed by conventional PCR. Sequencing of PCR products further validated these observations. No significant difference in the expression level of CXC ligand 3 was found between postpartum-derived cells and controls using conventional PCR CXC ligand 3 primers listed in Table 9-1.

The expression of the cytokine IL-8 in postpartum-derived cells is elevated in both Growth medium-cultured and serum-starved postpartum-derived cells. All real-time PCR data was validated with conventional PCR and by sequencing PCR products.

When supernatants of cells grown in serum-free medium were examined for the presence of IL-8, the highest amounts were detected in media derived from umbilical cord-derived cells and some isolates of placenta-derived cells (Table 9-2). No IL-8 was detected in medium derived from human dermal fibroblasts.

TABLE 9-2

| IL-8 protein expression measured by ELISA | |
| --- | --- |
| Cell type | IL-8 |
| Human fibroblasts | ND |
| Placenta Isolate 1 | ND |
| UMBC Isolate 1 | 2058.42 ± 144.67 |
| Placenta Isolate 2 | ND |
| UMBC Isolate 2 | 2368.86 ± 22.73 |
| Placenta Isolate3 (normal $O_2$) | 17.27 ± 8.63 |
| Placenta Isolate 3 (low$O_2$, W/O BME) | 264.92 ± 9.88 |

Results of the ELISA assay for interleukin-8 (IL-8) performed on placenta- and umbilical cord-derived cells as well as human skin fibroblasts. Values are presented here are picogram/million cells, n = 2, sem.
ND: Not Detected Placenta-derived cells were also examined for the expression of oxidized LDL receptor, GCP-2, and GROalpha by FACS analysis. Cells tested positive for GCP-2. Oxidized LDL receptor and GRO were not detected by this method.

Placenta-derived cells were also tested for the production of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Cells derived from the human umbilical cord at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilical cord-derived cells were positive for alpha-smooth muscle actin and vimentin, with the staining pattern consistent through passage 11.

Placenta-derived cells at passage 11 were also investigated by immunocytochemistry for the production of GROalpha and GCP-2. Placenta-derived cells were GCP-2 positive, but GROalpha production was not detected by this method.

The production of GROalpha, GCP-2, oxidized LDL receptor 1 and reticulon (NOGO-A) in umbilical cord-derived cells at passage 11 was investigated by immunocytochemistry. Umbilical cord-derived cells were GCP-2 positive, but GRO alpha production was not detected by this method. Furthermore, cells were NOGO-A positive.

Summary. Accordance between gene expression levels measured by microarray and PCR (both real-time and conventional) has been established for four genes: oxidized LDL receptor 1, renin, reticulon, and IL-8. The expression of these genes was differentially regulated at the mRNA level in postpartum-derived cells, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level; however, GCP-2 was detected at the protein level by FACS analysis in the placenta-derived cells. Although this result does not support data originally obtained from the microarray experiment, this may be due to a difference in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin expression may be preserved in cells with passaging, at least in the Growth medium used here.

Cells derived from the human umbilical cord at passage 0 were probed for the expression of alpha-smooth muscle actin and vimentin. and were positive for both. The staining pattern was preserved through passage 11.

In conclusion, the complete mRNA data at least partially verifies the data obtained from the microarray experiments.

Example 10

Immunohistochemical Characterization of PPDC Phenotype

The phenotypes of cells found within human postpartum tissues, namely umbilical cord and placenta, were analyzed by immunohistochemistry.

Materials & Methods

Tissue Preparation. Human umbilical cord and placenta tissue were harvested and immersion fixed in 4% (w/v) paraformaldehyde overnight at 4° C. Immunohistochemistry was performed using antibodies directed against the following epitopes (see Table 10-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 micron thick) using a standard cryostat (Leica Microsystems) and mounted onto glass slides for staining.

TABLE 10-1

Summary of Primary Antibodies Used

| Antibody | Concentration | Vendor |
| --- | --- | --- |
| Vimentin | 1:500 | Sigma, St. Louis, MO |
| Desmin (rb) | 1:150 | Sigma |
| Desmin (m) | 1:300 | Chemicon, Temecula, CA |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |
| GROalpha-PE | 1:100 | BD, Franklin Lakes, NJ |
| GCP-2 | 1:100 | Santa Cruz Biotech |
| Ox-LDL R1 | 1:100 | Santa Cruz Biotech |
| NOGO-A | 1:100 | Santa Cruz Biotech |

Immunohistochemistry. Immunohistochemistry was performed similar to previous studies (e.g., Messina, et al. (2003) Exper. Neurol. 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Umbilical Cord Characterization. Vimentin, desmin, SMA, CK18, vWF, and CD34 markers were expressed in a subset of the cells found within umbilical cord (data not shown). In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery & vein, but not contained with the vessels themselves. CK18 and desmin were observed within the vessels only, desmin being restricted to the middle and outer layers.

Placenta Characterization. Vimentin, desmin, SMA, CK18, vWF, and CD34 were all observed within the placenta and regionally specific.

GROalpha, GCP-2, ox-LDL R1, and NOGO-A Tissue Expression. None of these markers were observed within umbilical cord or placental tissue (data not shown).

Summary. Vimentin, desmin, alpha-smooth muscle actin, cytokeratin 18, von Willebrand Factor, and CD 34 are expressed in cells within human umbilical cord and placenta. Based on in vitro characterization studies showing that only vimentin and alpha-smooth muscle actin are expressed, the data suggests that the current process of postpartum-derived cell isolation harvests a subpopulation of cells or that the cells isolated change expression of markers to express vimentin and alpha-smooth muscle actin.

Example 11

In Vitro Immunology of Postpartum-Derived Cells

Postpartum-derived cell lines were evaluated in vitro for their immunological characteristics in an effort to predict the immunological response, if any, these cells would elicit upon in vivo transplantation. Postpartum-derived cell lines were assayed by flow cytometry for the expression of HLA-DR, HLA-DP, HLA-DQ, CD80, CD86, and B7-H2. These proteins are expressed by antigen-presenting cells (APC) and are required for the direct stimulation of naïve CD4+ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, CELLULAR AND MOLECULAR IMMUNOLOGY, 5th Ed. (2003) Saunders, Philadelphia, p. 171), CD 178 (Coumans, et. al., (1999) *Journal of Immunological Methods* 224, 185-196), and PD-L2 (Abbas & Lichtman, CELLULAR AND MOLECULAR IMMUNOLOGY, 5th Ed. (2003) Saunders, Philadelphia, p. 171; Brown, et. al. (2003) *The Journal of Immunology* 170, 1257-1266). The expression of these proteins by cells residing in placental tissues is thought to mediate the immuno-privileged status of placental tissues in utero. To predict the extent to which postpartum placenta- and umbilical cord-derived cell lines elicit an immune response in vivo, the cell lines were tested in a one-way mixed lymphocyte reaction (MLR).

Materials and Methods

Cell culture. Cells were cultured in Growth medium (DMEM-low glucose (Gibco, Carlsbad, Calif.), 15% (v/v) fetal bovine serum (FBS); (Hyclone, Logan, Utah), 0.001% (v/v) betamercaptoethanol (Sigma, St. Louis, Mo.), 50 Units/milliliter penicillin, 50 micrograms/milliliter streptomycin (Gibco, Carlsbad, Calif.)) until confluent in T75 flasks (Corning, Corning, N.Y.) coated with 2% gelatin (Sigma, St. Louis, Mo.).

Antibody Staining. Cells were washed in phosphate buffered saline (PBS) (Gibco, Carlsbad, Calif.) and detached with Trypsin/EDTA (Gibco, Carlsbad, Calif.). Cells were harvested, centrifuged, and re-suspended in 3% (v/v) FBS in PBS at a cell concentration of $1 \times 10^7$ per milliliter. Antibody (Table 11-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 11-1

Antibodies

| Antibody | Manufacturer | Catalog Number |
|---|---|---|
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego,CA) | 557846 |
| Mouse IgG2a | Sigma (St. Louis, MO) | F-6522 |
| Mouse IgG1 kappa | Sigma (St. Louis, MO) | P-4685 |

Mixed Lymphocyte Reaction. Cryopreserved vials of passage 10 umbilical cord-derived PPDCs labeled as cell line A and passage 11 placenta-derived PPDCs labeled as cell line B were sent on dry ice to CTBR (Senneville, Quebec) to conduct a mixed lymphocyte reaction using CTBR SOP no. CAC-031. Peripheral blood mononuclear cells (PBMCs) were collected from multiple male and female volunteer donors. Stimulator (donor) allogeneic PBMC, autologous PBMC, and postpartum-derived cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the postpartum-derived cells was calculated as the mean proliferation of the receiver plus mitomycin C-treated postpartum-derived cell line divided by the baseline proliferation of the receiver.

Results

Mixed Lymphocyte Reaction-Placenta. Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta-derived cell lines were treated with mitomycin C and cultured in a mixed lymphocyte reaction with the six individual allogeneic receivers. Reactions were performed in triplicate using two cell culture plates with three receivers per plate (Table 11-2). The average stimulation index ranged from 1.3 (plate 2) to 3 (plate 1) and the allogeneic donor positive controls ranged from 46.25 (plate 2) to 279 (plate 1) (Table 11-3).

TABLE 11-2

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| | Plate ID: Plate1 | | | | | | |
| IM03-7769 | Proliferation baseline of receiver | 79 | 119 | 138 | 112.0 | 30.12 | 26.9 |
| | Control of autostimulation (Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| SI (donor) | | | | | 200 | | |
| SI (cell line) | | | | | 7 | | |
| IM03-7770 | Proliferation baseline of receiver | 206 | 134 | 262 | 200.7 | 64.17 | 32.0 |
| | Control of autostimulation (Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| SI (donor) | | | | | 221 | | |
| SI (cell line) | | | | | 9 | | |
| IM03-7771 | Proliferation baseline of receiver | 157 | 87 | 128 | 124.0 | 35.17 | 28.4 |
| | Control of autostimulation (Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| SI (donor) | | | | | 243 | | |
| SI (cell line) | | | | | 5 | | |
| IM03-7772 | Proliferation baseline of receiver | 56 | 98 | 51 | 68.3 | 25.81 | 37.8 |
| | Control of autostimulation (Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| SI (donor) | | | | | 275 | | |
| SI (cell line) | | | | | a | | |
| IM03-7768 | Proliferation baseline of receiver | 84 | 242 | 208 | 178.0 | 83.16 | 46.7 |
| (allogenic donor) | Control of autostimulation (Mitomycin treated autologous cells) | 361 | 617 | 304 | 427.3 | 166.71 | 39.0 |
| Cell line type B | Proliferation baseline of receiver | 126 | 124 | 143 | 131.0 | 10.44 | 8.0 |
| | Control of autostimulation (Mitomycin treated autologous cells) | 822 | 1075 | 487 | 794.7 | 294.95 | 37.1 |
| | Plate ID: Plate 2 | | | | | | |
| IM03-7773 | Proliferation baseline of receiver | 908 | 181 | 330 | 473.0 | 384.02 | 81.2 |
| | Control of autostimulation (Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| SI (donor) | | | | | 61 | | |
| SI (cell line) | | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 294 | 532.7 | 247.97 | 46.6 |
| SI (donor) | | | | | 59 | | |
| SI (cell line) | | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28965 | 21014.0 | 9479.74 | 45.1 |
| | MLR with cell line (Mitomycin C treated cell type B) | 768 | 924 | 563 | 751.7 | 181.05 | 24.1 |
| SI (donor) | | | | | 30 | | |
| SI (cell line) | | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| SI (donor) | | | | | 35 | | |
| SI (cell line) | | | | | a | | |

TABLE 11-3

Average stimulation index of placenta cells and an allogeneic donor in a mixed lymphocyte reaction with six individual allogeneic receivers.

| | Average Stimulation Index | |
|---|---|---|
| | Recipient | Placenta |
| Plate 1 (receivers 1-3) | 279 | 3 |
| Plate 2 (receivers 4-6) | 46.25 | 1.3 |

Mixed Lymphocyte Reaction—Umbilical cord. Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and umbilical cord-derived cell lines were mitomycin C-treated and cultured in a mixed lymphocyte reaction with the five individual allogeneic receivers. Reactions were performed in triplicate using two cell culture plates with three receivers per plate (Table 11-4). The average stimulation index ranged from 6.5 (plate 1) to 9 (plate 2) and the allogeneic donor positive controls ranged from 42.75 (plate 1) to 70 (plate 2) (Table 11-5).

TABLE 11-4

Mixed Lymphocyte Reaction Data- Cell Line A (Umbilical cord)
DPM for Proliferation Assay

| Analytical number | Culture System | Replicates 1 | 2 | 3 | Mean | SD | CV |
|---|---|---|---|---|---|---|---|
| Plate ID: Plate1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| SI (donor) | | | | | 70 | | |
| SI (cell line) | | | | | 9 | | |
| IM04-2477 (allogenic donor) Cell line type A | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 11-5

Average stimulation index of umbilical cord-derived cells and an allogeneic donor in a mixed lymphocyte reaction with five individual allogeneic receivers.
Average Stimulation Index

| | Recipient | Umbilical Cord |
|---|---|---|
| Plate 1 (receivers 1-4) | 42.75 | 6.5 |
| Plate 2 (receiver 5) | 70 | 9 |

Antigen Presenting Cell Markers—Placenta. Histograms of placenta-derived cells analyzed by flow cytometry show negative expression of HLA-DR, DP, DQ, CD80, CD86, and B7-H2, as noted by fluorescence value consistent with the IgG control, indicating that placenta-derived cell lines lack the cell surface molecules required to directly stimulate allogeneic PBMCs (e.g., CD4$^+$ T cells).

Immuno-modulating Markers—Placenta-derived cells. Histograms of placenta-derived cells analyzed by flow cytometry show positive expression of PD-L2, as noted by the increased value of fluorescence relative to the IgG control, and negative expression of CD178 and HLA-G, as noted by fluorescence value consistent with the IgG control (data not shown).

Antigen Presenting Cell Markers—Umbilical cord-derived cells. Histograms of umbilical cord-derived cells analyzed by flow cytometry show negative expression of HLA-DR, DP, DQ, CD80, CD86, and B7-H2, as noted by fluorescence value consistent with the IgG control, indicating that umbilical cord-derived cell lines lack the cell surface molecules required to directly stimulate allogeneic PBMCs (e.g., CD4$^+$ T cells).

Immuno-modulating Markers—Umbilical cord-derived cells. Histograms of umbilical cord-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Summary. In the mixed lymphocyte reactions conducted with placenta-derived cell lines, the average stimulation index ranged from 1.3 to 3, and that of the allogeneic positive controls ranged from 46.25 to 279. In the mixed lymphocyte reactions conducted with umbilical cord-derived cell lines, the average stimulation index ranged from 6.5 to 9, and that of the allogeneic positive controls ranged from 42.75 to 70. Placenta- and umbilical cord-derived cell lines were negative for the expression of the stimulating proteins HLA-DR, HLA-DP, HLA-DQ, CD80, CD86, and B7-H2, as measured by flow cytometry. Placenta- and umbilical cord-derived cell lines were negative for the expression of immuno-modulating proteins HLA-G and CD178 and positive for the expression of PD-L2, as measured by flow cytometry. Allogeneic donor PBMCs contain antigen-presenting cells expressing HLA-DP, DR, DQ, CD80, CD86, and B7-H2, thereby allowing for the stimulation of allogeneic PBMCs (e.g., naïve $CD4^+$ T cells). The absence of antigen-presenting cell surface molecules on placenta- and umbilical cord-derived cells required for the direct stimulation of allogeneic PBMCs (e.g., naïve $CD4^+$ T cells) and the presence of PD-L2, an immuno-modulating protein, may account for the low stimulation index exhibited by these cells in a MLR as compared to allogeneic controls.

REFERENCES

Bruder S P et. al. U.S. Pat. No. 6,355,239 B1 (2002)
Abbas, A K, Lichtman, A H Cellular and Molecular Immunology 5th Ed. (2003) Saunders, Philadelphia, p. 171
Bouteiller P. Le et. al., (2003) Placenta 24;S10-S15
Coumans B et. al., (1999) Journal of Immunological Methods 224, 185-196]
Brown, Julia et. al. (2003) The Journal of Immunology 170, 1257-1266

Example 12

Secretion of Trophic Factors by Postpartum-Derived Cells

The secretion of selected trophic factors from placenta- and umbilical cord-derived PPDCs was measured. Factors were selected that have angiogenic activity (i.e., hepatocyte growth factor (HGF) (Rosen et al. (1997) *Ciba Found. Symp.* 212:215-26), monocyte chemotactic protein 1 (MCP-1) (Salcedo et al. (2000) *Blood* 96;34-40), interleukin-8 (IL-8) (Li et al. (2003) *J. Immunol.* 170:3369-76), keratinocyte growth factor (KGF), basic fibroblast growth factor (bFGF), vascular endothelial growth factor (VEGF) (Hughes et al. (2004) *Ann. Thorac. Surg.* 77:812-8), tissue inhibitor of matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1a (SDF-1a)), neurotrophic/neuroprotective activity (brain-derived neurotrophic factor (BDNF) (Cheng et al. (2003) *Dev. Biol.* 258;319-33), interleukin-6 (IL-6), granulocyte chemotactic protein-2 (GCP-2), transforming growth factor beta2 (TGF-beta2)), or chemokine activity (macrophage inflammatory protein 1a (MIP1a), macrophage inflammatory protein 1beta (MIP1b), monocyte chemoattractant-1 (MCP-1), Rantes (regulated on activation, normal T cell expressed and secreted), 1309, thymus and activation-regulated chemokine (TARC), Eotaxin, macrophage-derived chemokine (MDC), IL-8).

Methods & Materials

Cell culture. PPDCs derived from placenta and umbilical cord as well as human fibroblasts derived from human neonatal foreskin were cultured in Growth medium (DMEM-low glucose (Gibco, Carlsbad, Calif.), 15% (v/v) fetal bovine serum (SH30070.03; Hyclone, Logan, Utah), 50 Units/milliliter penicillin, 50 micrograms/milliliter streptomycin (Gibco)) on gelatin-coated T75 flasks. Cells were cryopreserved at passage 11 and stored in liquid nitrogen. After thawing of the cells, Growth medium was added to the cells followed by transfer to a 15 milliliter centrifuge tube and centrifugation of the cells at 150×g for 5 minutes. The supernatant was discarded. The cell pellet was resuspended in 4 milliliter Growth medium, and cells were counted. Cells were seeded at 5,000 cells/cm² on a T75 flask containing 15 milliliter of Growth medium and cultured for 24 hours. The medium was changed to a serum-free medium (DMEM-low glucose (Gibco), 0.1% (w/v) bovine serum albumin (Sigma), 50 Units/milliliter penicillin, 50 micrograms/milliliter streptomycin (Gibco)) for 8 hours. Conditioned serum-free media was collected at the end of incubation by centrifugation at 14,000×g for 5 minutes and stored at −0° C. To estimate the number of cells in each flask, cells were washed with phosphate-buffered saline (PBS) and detached using 2 milliliter trypsin/EDTA (Gibco). Trypsin activity was inhibited by addition of 8 milliliter Growth medium. Cells were centrifuged at 150×g for 5 minutes. Supernatant was removed, and cells were resuspended in 1 milliliter Growth Medium. Cell number was estimated using a hemocytometer.

ELISA assay. Cells were grown at 37° C. in 5% carbon dioxide and atmospheric oxygen. Placenta-derived PPDCs (101503) also were grown in 5% oxygen or beta-mercaptoethanol (BME). The amount of MCP-1, IL-6, VEGF, SDF-1a, GCP-2, IL-8, and TGF-beta2 produced by each cell sample was measured by an ELISA assay (R&D Systems, Minneapolis, Minn.). All assays were performed according to the manufacturer's instructions. Values presented are picogram/milliliter/million cells (n=2, sem).

SEARCHLIGHT Multiplexed ELISA assay. Chemokines (MIP1a, MIP1b, MCP-1, Rantes, I309, TARC, Eotaxin, MDC, IL8), BDNF, and angiogenic factors (HGF, KGF, bFGF, VEGF, TIMP1, ANG2, PDGF-bb, TPO, HB-EGF were measured using a multiplexed chemiluminescent ELISA assay sold under the trademark SEARCHLIGHT (SEARCHLIGHT Proteome Arrays; Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the original standard or sample.

Results

ELISA assay. MCP-1 and IL-6 were secreted by placenta- and umbilical cord-derived PPDCs and dermal fibroblasts (Table 12-1). Umbilical cord-derived cells secreted at least 10-fold higher amounts of MCP-1 and IL6 than other cell populations. GCP-2 and IL-8 were highly expressed by umbilical-derived PPDCs. TGF-beta2 was not detectable. VEGF was detected in fibroblast medium.

The amounts of HGF, FGF, and BDNF secreted from umbilical cord-derived cells were noticeably higher than fibroblasts and placenta-derived cells (Tables 12-2 and 12-3). Similarly, TIMP1, TPO, HBEGF, MCP-1, TARC, and IL-8 were higher in umbilical cord-derived cells than other cell populations (Table 12-3). No ANG2 or PDGF-bb were detected.

TABLE 12-1

ELISA assay results

|  | MCP-1 | IL-6 | VEGF | SDF-1a | GCP-2 | IL-8 | TGF-beta2 |
|---|---|---|---|---|---|---|---|
| Fibroblast | 17 ± 1 | 61 ± 3 | 29 ± 2 | 19 ± 1 | 21 ± 1 | ND | ND |
| Placenta (042303) | 60 ± 3 | 41 ± 2 | ND | ND | ND | ND | ND |
| Umbilical (022803) | 1150 ± 74 | 4234 ± 289 | ND | ND | 160 ± 11 | 2058 ± 145 | ND |
| Placenta (071003) | 125 ± 16 | 10 ± 1 | ND | ND | ND | ND | ND |
| Umbilical (071003) | 2794 ± 84 | 1356 ± 43 | ND | ND | 2184 ± 98 | 2369 ± 23 | ND |
| Placenta (101503) BME | 21 ± 10 | 67 ± 3 | ND | ND | 44 ± 9 | 17 ± 9 | ND |
| Placenta (101503) 5% $O_2$, W/O BME | 77 ± 16 | 339 ± 21 | ND | 1149 ± 137 | 54 ± 2 | 265 ± 10 | ND |

Key: ND: Not Detected.

TABLE 12-2

SEARCHLIGHT Multiplexed ELISA assay results

|  | TIMP1 | ANG2 | PDGFbb | TPO | KGF | HGF | FGF | VEGF | HBEGF | BDNF |
|---|---|---|---|---|---|---|---|---|---|---|
| hFB | 19306.3 | ND | ND | 230.5 | 5.0 | ND | ND | 27.9 | 1.3 | ND |
| P1 | 24299.5 | ND | ND | 546.6 | 8.8 | 16.4 | ND | ND | 3.81.3 | ND |
| U1 | 57718.4 | ND | ND | 1240.0 | 5.8 | 559.3 | 148.7 | ND | 9.3 | 165.7 |
| P3 | 14176.8 | ND | ND | 568.7 | 5.2 | 10.2 | ND | ND | 1.9 | 33.6 |
| U3 | 21850.0 | ND | ND | 1134.5 | 9.0 | 195.6 | 30.8 | ND | 5.4 | 388.6 |

Key: hFB (human fibroblasts), P1 (placenta-derived PPDC (042303)), U1 (umbilical cord-derived PPDC (022803)), P3 (placenta-derived PPDC (071003)), U3 (umbilical cord-derived PPDC (071003)). ND: Not Detected.

TABLE 12-3

SEARCHLIGHT Multiplexed ELISA assay results

|  | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| P1 | 79.5 | ND | 228.4 | 4.1 | ND | 3.8 | 12.2 | ND | 413.5 |
| U1 | ND | 8.0 | 1694.2 | ND | 22.4 | 37.6 | ND | 18.9 | 51930.1 |
| P3 | ND | ND | 102.7 | ND | ND | 0.4 | ND | ND | 63.8 |
| U3 | ND | 5.2 | 2018.7 | 41.5 | 11.6 | 21.4 | ND | 4.8 | 10515.9 |

Key: hFB (human fibroblasts), P1 (placenta-derived PPDC (042303)), U1 (umbilical cord-derived PPDC (022803)), P3 (placenta-derived PPDC (071003)), U3 (umbilical cord-derived PPDC (071003)). ND: Not Detected.

Summary. Umbilical cord-cells secreted significantly higher amount of trophic factors than placenta-derived cells and fibroblasts. Some of these trophic factors, such as HGF, bFGF, MCP-1 and IL-8, play important roles in angiogenesis. Other trophic factors, such as BDNF and IL-6, have important roles in neural regeneration. Under these conditions, the expression of some factors was confined to umbilical cord-derived cells, such as MIP1b, Rantes, I309, and FGF.

REFERENCES

Le Belle J E, Svendsen C N. (2002) Stem cells for neurodegenerative disorders: where can we go from here? BioDrugs. 16;389-401

Rosen E M, Lamszus K, Laterra J, Polyerini P J, Rubin J S, Goldberg I D. (1997) HGF/SF in angiogenesis. Ciba Found Symp. 212;215-26.

Salcedo R, Ponce M L, Young H A, Wasserman K, Ward J M, Kleinman H K, Oppenheim J J, Murphy W J. (2000) Human endothelial cells express CCR2 and respond to MCP-1: direct role of MCP-1 in angiogenesis and tumor progression. Blood. 96;34-40.

Li A, Dubey S, Varney M L, Dave B J, Singh R K (2003) IL-8 directly enhanced endothelial cell survival, proliferation, and matrix metalloproteinases production and regulated angiogenesis. J. Immunol. 170;3369-76

Hughes G C, Biswas S S, Yin B, Coleman R E, DeGrado T R, Landolfo C K, Lowe J E, Annex B H, Landolfo K P. (2004) Therapeutic angiogenesis in chronically ischemic porcine myocardium: comparative effects of bFGF and VEGF. Ann Thorac Surg. 77;812-8.

Cheng A, Wang S, Cai J, Rao M S, Mattson M P (2003) Nitric oxide acts in a positive feedback loop with BDNF to regulate neural progenitor cell proliferation and differentiation in the mammalian brain. Dev Biol. 258;319-33.

Sebire G, Emilie D, Wallon C, Hery C, Devergne O, Delfraissy J F, Galanaud P, Tardieu M. (1993) In vitro production of IL-6, IL-1 beta, and tumor necrosis factor-alpha by human embryonic microglial and neural cells. J. Immunol. 150;1517-23.

Example 13

Plasma Clotting Assay

Cell therapy may be injected systemically for certain applications where cells are able to target the site of action. It is important that injected cells not cause thrombosis, which may be fatal. Tissue factor, a membrane-bound procoagulant glycoprotein, is the initiator of the extrinsic clotting cascade, which is the predominant coagulation pathway in vivo. Tissue factor also plays an important role in embryonic vessel formation, for example, in the formation of the primitive vascular wall (Brodsky et al. (2002) *Exp. Nephrol.* 10:299-306). To determine the potential for PPDCs to initiate clotting, umbilical cord- and placenta-derived PPDCs were evaluated for tissue factor expression and their ability to initiate plasma clotting.

Methods & Materials

Human Tissue factor. Human tissue factor SIMPLASTIN (Organon Tekailca Corporation, Durham, N.C.), was reconstituted with 20 milliliter distilled water. The stock solution was serially diluted (1:2) in eight tubes. Normal human plasma (George King Bio-Medical, Overland Park, Kans.) was thawed at 37° C. in a water bath and then stored in ice before use. To each well of a 96-well plate was added 100 microliter phosphate buffered saline (PBS), 10 microliter diluted Simplastin® (except a blank well), 30 microliter 0.1 molar calcium chloride, and 100 microliter of normal human plasma. The plate was immediately placed in a temperature-controlled microplate reader and absorbance measured at 405 nanometer at 40 second intervals for 30 minutes.

J-82 and postpartum-derived cells. J-82 cells (ATCC, MD) were grown in Iscove's modified Dulbecco's medium (IMDM; Gibco, Carlsbad, Calif.) containing 10% (v/v) fetal bovine serum (FBS; Hyclone, Logan Utah), 1 millimolar sodium pyruvate (Sigma Chemical, St. Louis, Mo.), 2 millimolar L-Glutamin (Mediatech Herndon, Va.), 1× non-essential amino acids (Mediatech Herndon, Va.). At 70% confluence, cells were transferred to wells of 96-well plate at 100,000, 50,000, and 25,000 cells/well. Postpartum cells derived from placenta and umbilical cord were cultured in Growth Medium (DMEM-low glucose (Gibco), 15% (v/v) FBS, 50 Units/milliliter penicillin, 50 micrograms/milliliter streptomycin (Gibco), and 0.001% betamercaptoethanol (Sigma)) in gelatin-coated T75 flasks (Corning, Corning, N.Y.). Placenta-derived cells at passage 5 and umbilical cord-derived cells at passages 5 and 11 were transferred to wells at 50,000 cells/well. Culture medium was removed from each well after centrifugation at 150×g for 5 minutes. Cells were suspended in PBS without calcium and magnesium. Cells incubated with anti-tissue factor antibody cells were incubated with 20 microgram/milliliter CNTO 859 (Centocor, Malvern, Pa.) for 30 minutes. Calcium chloride (30 microliter) was added to each well. The plate was immediately placed in a temperature-controlled microplate reader and absorbance measured at 405 nanometers at 40 second intervals for 30 minutes.

Antibody Staining. Cells were washed in PBS and detached from the flask with Trypsin/EDTA (Gibco Carlsbad, Calif.). Cells were harvested, centrifuged, and re-suspended 3% (v/v) FBS in PBS at a cell concentration of $1 \times 10^7$ per milliliter. Antibody was added to 100 microliter cell suspension as per the manufacturer's specifications, and the cells were incubated in the dark for 30 minutes at 4° C. After incubation, cells were washed with PBS and centrifuged at 150×g for 5 minutes to remove unbound antibody. Cells were re-suspended in 100 microliter of 3% FBS and secondary antibody added as per the manufacturer's instructions. Cells were incubated in the dark for 30 minutes at 4° C. After incubation, cells were washed with PBS and centrifuged to remove unbound secondary antibody. Washed cells were re-suspended in 500 microliter of PBS and analyzed by flow cytometry.

Flow Cytometry Analysis. Flow cytometry analysis was performed with a FACSCalibur instrument (Becton Dickinson, San Jose, Calif.).

Results

Flow cytometry analysis revealed that both placenta- and umbilical cord-derived postpartum cells express tissue factor. A plasma clotting assay demonstrated that tissue factor was active. Both placenta- and umbilical cord-derived cells increased the clotting rate as indicated by the time to half maximal absorbance (T ½ to max; Table 13-1). Clotting was observed with both early (P5) and late (P18) cells. The T ½ to max is inversely proportional to the number of J82 cells. Preincubation of umbilical cells with CNTO 859, an antibody to tissue factor, inhibited the clotting reaction, thereby showing that tissue factor was responsible for the clotting.

TABLE 13-1

The effect of human tissue factor (SIMPLASTIN), placenta-derived cells (Pla), and umbilical cord-derived cells (Umb) on plasma clotting was evaluated. The time to half maximal absorbance (T ½ to max) at the plateau in seconds was used as a measurement unit.

| Simplastin ® Dilution | T ½ to max (seconds) |
|---|---|
| 1:2 | 61 |
| 1:4 | 107 |
| 1:8 | 147 |
| 1:16 | 174 |
| 1:32 | 266 |
| 1:64 | 317 |
| 1:128 | 378 |
| 0 (negative control) | 1188 |
| J-82 cells | |
| 100,000 | 122 |
| 50,000 | 172 |
| 25,000 | 275 |
| Pla P5 | |
| 50,000 | 757 |
| Umb P5 | |
| 50,000 | 833 |
| Umb P18 | |
| 50,000 | 443 |

Summary. Placenta- and umbilical cord-derived PPDCs express tissue factor, which can induce clotting. The addition of an antibody to tissue factor can inhibit tissue factor. Tissue factor is normally found on cells in a conformation that is inactive but is activated by mechanical or chemical (e.g., LPS) stress (Sakariassen et al. (2001) *Thromb. Res.* 104:149-74; Engstad et al. (2002) *Int. Immunopharmacol.*

2:1585-97). Thus, minimization of stress during the preparation process of PPDCs may prevent activation of tissue factor. In addition to the thrombogenic activity, tissue factor has been associated with angiogenic activity. Thus, tissue factor activity may be beneficial when umbilical cord- or placenta-derived PPDCs are transplanted in tissue but should be inhibited when PPDCs are injected intravenously.

REFERENCES

Doshi and Marmur, *Critical Care Med.*, 30:S241-S250 (2002)

Moll and Ortel, *Ann. Intern. Med.*, 127:177-185 (1997)

Example 14

Differentiation of PPDCs to an Osteogenic Phenotype

Mesenchymal stem cells (MSCs) derived from bone marrow can differentiate into osteoblast-like cells that mineralize and express alkaline phosphatase. Additional markers expressed by osteoblasts, such as osteocalcin and bone sialoprotein, have also been used to demonstrate differentiation into an osteoblast-like cell. A determination was made as to whether postpartum-derived cells can also differentiate into an osteogenic phenotype by culturing in an osteogenic medium and in the presence of bone morphogenic proteins (BMP)-2 (Rickard et al., 1994) or -4, and transforming growth factor beta 1.

Methods & Materials

Culture of cells. Prior to initiation of osteogenesis, Mesenchymal Stem Cells (MSC) were grown in Mesenchymal Stem Cell Growth Medium Bullet kit (MSCGM, Cambrex, Walkerville, Md.). Other cells were cultured in Growth medium (DMEM-low glucose (Gibco, Carlsbad, Calif.), 15% (v/v) fetal bovine serum (SH30070.03; Hyclone, Logan, Utah), 0.001% (v/v) betamercaptoethanol (Sigma, St. Louis, Mo.), penicillin/streptomycin (Gibco)), in a gelatin-coated T75 flask were washed with phosphate buffered saline (PBS).

Osteoblasts (9F1721; Cambrex) were grown in osteoblast growth medium (Cambrex) and RNA was extracted as described below.

Osteogenesis

Protocol 1. Placenta-derived cells, isolate 1, P3, placenta-derived cells, isolate 2, P4 (previously karyotyped and shown to be predominantly neonatal-derived cells), umbilical cord-derived cells isolate 1, P4, and MSC at P3 were seeded at $5 \times 10^3$ cells/cm$^2$ in 24 well plates and 6-well dishes in Growth medium and incubated overnight. The medium was removed and replaced with Osteogenic medium (DMEM-low glucose, 10% (v/v) fetal bovine serum, 10 millimolar betaglycerophosphate (Sigma), 100 nanomolar dexamethasone (Sigma, St. Louis, Mo.), 50 micromolar ascorbate phosphate salt (Sigma), fungizone (Gibco), penicillin and streptomycin (Gibco)). Osteogenic medium was supplemented with 20 nanograms/milliliter hTGF-beta1 (Sigma), 40 nanograms/milliliter hrBMP-2 (Sigma), or 40 nanograms/milliliter hrBMP-4 (Sigma). Cultures were treated for a total of 14, 21 and 28 days, with media changes every 3-4 days.

Protocol 2. Postpartum-derived cells were tested for the ability to differentiate into an osteogenic phenotype. Umbilical cord-derived cells (isolate 1, P3 & isolate 2, P4) and placenta-derived cells (isolate 1; P4 & isolate 2, P4) were seeded at 30,000 cells/well in 6-well, gelatin-coated plates in Growth medium. Mesenchymal stem cells (MSC) (isolate 1; P3 & isolate 2; P4), fibroblasts (1F1853, P11), and iliac crest bone marrow cells (070203; P3; WO2003025149) were also seeded at 30,000 cells/well in 6-well, gelatin-coated plates (gelatin-coated) in mesenchymal stem cell growth medium (MSCGM, Cambrex) and Growth medium, respectively.

Osteogenic induction was initiated by removing the initial seeding media (24 h) and replacing it with osteogenic induction medium (DMEM-low glucose, 10% fetal bovine serum, 10 millimolar betaglycerophosphate (Sigma), 100 nanomolar dexamethasone (Sigma), 50 micromolar ascorbate phosphate salt (Sigma), penicillin and streptomycin (Gibco)). In some cases, osteogenic medium was supplemented with either hrBMP-2 (20 nanograms/milliliter) (Sigma), hrBMP-4 (Sigma), or with both hrBMP-2 (20 nanograms/milliliter) and hrBMP-4 (20 nanograms/milliliter) (Sigma). Cultures were treated for a total of 28 days, with media changes every 3-4 days.

RNA extraction and Reverse Transcription. Cells were lysed with 350 microliter buffer RLT containing beta-mercaptoethanol (Sigma, St. Louis, Mo.) according to the manufacturer's instructions (RNEASY Mini kit, Qiagen, Valencia, Calif.) and stored at −80° C. Cell lysates were thawed and RNA extracted according to the manufacturer's instructions (RNEASY Mini kit, Qiagen, Valencia, Calif.) with a 2.7 U/sample DNase treatment (Sigma St. Louis, Mo.). RNA was eluted with 50 microliter DEPC-treated water and stored at −80° C. RNA was reverse transcribed using random hexamers with the TaqMan reverse transcription reagents (Applied Biosystems, Foster City, Calif.) at 25° C. for 10 minutes, 37° C. for 60 minutes and 95° C. for 10 minutes. Samples were stored at −20° C.

Polymerase Chain Reaction. PCR was performed on cDNA samples using Assays-on-Demand™ gene expression products bone sialoprotein (Hs00173720), osteocalcin (Hs00609452) GAPDH (Applied Biosystems, Foster City, Calif.), and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 min and 95° C. for 10 min followed by 40 cycles of 95° C. for 15 sec and 60° C. for 1 min.

von Kossa Staining. Cells were fixed with 10% (v/v) neutral buffered formalin (Richard-Allan, Kalamazoo, Mich.). After fixation, the cells were washed in deionized water and incubated in 5% (w/v) silver nitrate (Aldrich Chemical Company, Milwaukee, Wis.) for one hour in direct sunlight. Cells were then washed in DI water and incubated in 5% (w/v) sodium thiosulfate (EM Sciences, Gibbstown, N.J.) for five minutes. Cells were washed in distilled water and examined by light microscopy.

Results

Protocol 1. RNA extracted from osteoblasts was used as a positive control for the real-time gene expression of osteocalcin and bone sialoprotein. Osteoblast expression levels relative to placenta-derived cells grown in growth medium of osteocalcin and BSP was 2.5- and 8000-fold, respectively. MSCs grown in the osteogenic medium for 28 days mineralized and were positive for von Kossa staining. Extensive mineralization was observed in one placenta isolate that had predominantly neonatal-derived cells. Also, one placenta isolate show induction of BSP expression levels in osteogenic media and low levels of osteocalcin induction.

MSC expression of osteocalcin and BSP was significantly increased in osteogenic medium at 21 days. The addition of BMP-2 and -4 enhanced BSP expression but had no effect on osteocalcin expression. TGF-beta1 did not augment the effect of osteogenesis medium. BMP-4 and TGF-beta1 both increased osteocalcin expression by a placenta isolate.

Protocol 2. Osteogenic differentiation, as shown by positive von Kossa staining for mineralization, was observed with placenta-derived cells P4 and ICBM (070203), P3 incubated with osteogenic medium supplemented with BMP2 or 4, and MSCs (092903) P3 incubated with osteogenic medium supplemented with BMP 4 (Table 14-1). None of the other cells differentiated into the osteogenic phenotype and stained by von Kossa. To ensure that von Kossa staining was related to the cell and not to the extracellular matrix, cells were counterstained with nuclear fast red. Large lipid droplets were observed in some MSCs consistent with an adipocyte phenotype. This suggests that MSCs do not differentiate specifically into an osteogenic phenotype in these conditions. Furthermore, adipogenesis increased when MSCs were incubated in osteogenic medium supplemented with either BMP2 or BMP4.

TABLE 14-1

Results of osteogenic differentiation using von Kossa staining for Protocol 2. Umbilical cord-derived cells (Umb), placenta-derived cells (Pla), mesenchymal stem cells (MSC), fibroblasts (Fib), and iliac crest bone marrow cells (ICBM) cells were cultured in osteogenic medium (OM) alone or supplemented with BMP2 or BMP2 and BMP4.

| Number | Cell Line | Conditions | Von Kossa | Comments |
|---|---|---|---|---|
| 1 | Umb 071003 O1P3 | Osteogenic medium (OM) | Neg | |
| 2 | Umb 071003 O1P3 | OM, BMP2 | Neg | |
| 3 | Umb 071003 O1P3 | OM, BMP4 | Neg | |
| 4 | ICBM 070203 O1P3 | Osteogenic medium (OM) | Neg | Normal O2 |
| 5 | ICBM 070203 O1P3 | OM, BMP2 | Pos | Normal O3 |
| 6 | ICBM 070203 O1P3 | OM, BMP4 | Pos | Normal O4 |
| 7 | MSC 092903 | Osteogenic medium (OM) | Neg | lots of fat |
| 8 | MSC 092903 | OM, BMP2 | Neg | lots of fat |
| 9 | MSC 092903 | OM, BMP4 | Pos | lots of fat |
| 10 | Pla 101603 O1P4 | Osteogenic medium (OM) | Neg | |
| 11 | Pla 101603 O1P4 | OM, BMP2 | Pos | |
| 12 | Pla 101603 O1P4 | OM, BMP4 | Pos | |
| 13 | MSC 012104 O1P4 | Osteogenic medium (OM) | Neg | Fat |
| 14 | MSC 012104 O1P4 | OM, BMP2 | Neg | Fat |
| 15 | MSC 012104 O1P4 | OM, BMP2, BMP4 | Neg | Fat |
| 16 | Umb 022803 O1P4 | Osteogenic medium (OM) | Neg | |
| 17 | Umb 022803 O1P4 | OM, BMP2 | Neg | |
| 18 | Umb 022803 O1P4 | OM, BMP2, BMP4 | Neg | |
| 19 | Pla 100703 O1P4 | Osteogenic medium (OM) | Neg | |
| 20 | Pla 100703 O1P4 | OM, BMP2 | Neg | |
| 21 | Pla 100703 O1P4 | OM, BMP2, BMP4 | Neg | |
| 22 | Fib 1F1853 O1P11 | Osteogenic medium (OM) | Neg | |
| 23 | Fib 1F1853 O1P11 | OM, BMP2 | Neg | |
| 24 | Fib 1F1853 O1P11 | OM, BMP2, BMP4 | Neg | |

Summary. Bone marrow-derived MSCs (Kadiyala et al., 1997) as well as cells derived from other tissue such adipose (Halvorsen et al., 2001) have been shown to differentiate into osteoblast-like cells. MSCs have also been shown to differentiate into adipocytes or osteoblasts in response to BMPs (Chen et al., 1998) due to different roles for bone morphogenic protein (BMP) receptor type IB and IA.

Neonatal-derived placenta-derived cells and MSCs showed mineralization as well as induction of osteocalcin and bone sialoprotein. Under the conditions used, umbilical-derived cells did not show mineralization or induction of osteoblast genes. Maternal placenta-derived cells may require addition of BMP-4 or TGF to the osteogenic medium for mineralization to occur. The gestational age of the sample may also be a factor in the ability of cells derived from postpartum tissues to differentiate.

REFERENCES

Kadiyala S, Young R G, Thiede M A, Bruder S P. (1997) Culture expanded canine mesenchymal stem cells possess osteochondrogenic potential in vivo and in vitro. Cell Transplant. 6: 125-34.

Chen D, Ji X, Harris M A, Feng J Q, Karsenty G, Celeste A J, Rosen V, Mundy G R, Harris S E. (1998) Differential roles for bone morphogenic protein (BMP) receptor type IB and IA in differentiation and specification of mesenchymal precursor cells to osteoblast and adipocyte lineages. J. Cell Biol. 142:295-305

Halvorsen Y D, Franklin D, Bond A L, Hitt D C, Auchter C, Boskey A L, Paschalis E P, Wilkison W O, Gimble J M (2001) Extracellular matrix mineralization and osteoblast gene expression by human adipose tissue-derived stromal cells. Tissue Eng. 7:729-41.

Rickard D J et al., (1994) Induction of rapid osteoblast differentiation in rat bone marrow stromal cell cultures by dexamethasone and BMP-2. Dev Biol 161,:218-228.

WO2003025149 A2 HO, Tony, W.; KOPEN, Gene, C.; RIGHTER, William, F.; RUTKOWSKI, J., Lynn; HERRING, W., Joseph; RAGAGLIA, Vanessa; WAGNER, Joseph,. CELL POPULATIONS WHICH CO-EXPRESS CD49C AND CD90, NEURONYX, INC. Application No. PCT/US02/29971, Filed 20020920, A2 Published 20030327, A3 Published 20031218

Example 15

Chondrogenic Differentiation of Postpartum-Derived Cells

Cartilage damage and defects lead to approximately 600,000 surgical procedures each year in the United States alone (1). A number of strategies have been developed to treat these conditions but these have had limited success. One approach, Cartecel (Genzyme), uses autologous chondrocytes that are collected from a patient and expanded in vitro and then implanted into the patient (1). This approach has the disadvantage of collecting healthy cartilage and requiring a second procedure to implant the cultured cells. One novel possibility is a stem cell-based therapy in which cells are placed at or near the defect site to directly replace the damaged tissue. Cells may be differentiated into chondrocytes prior to the application or progenitor cells that can differentiate in situ may be used. Such transplanted cells would replace the chondrocytes lost in the defect.

Candidate cells for this indication should be evaluated for their ability to differentiate into chondrocytes in vitro. A number of protocols have been developed for testing the ability of cells to differentiate and express chondrocyte marker genes. Postpartum-derived cells were tested for their ability to differentiate into chondrocytes in vitro in two different assay systems: the pellet assay culture system and collagen gel cultures. The pellet culture system has been used successfully with selected lots of human mesenchymal stem cells (MSC). MSCs grown in this assay and treated with transforming growth factor-beta3 have been shown to differentiate into chondrocytes (2). The collagen gel system has been used to culture chondrocytes in vitro (3). Chondrocytes grown under these conditions form a cartilage-like structure.

Materials and Methods

Cell Culture

Postpartum tissue-derived cells. Human umbilical cords and placenta were received and cells were isolated as described above. Cells were cultured in Growth medium (Dulbecco's Modified Essential Media (DMEM) with 15% (v/v) fetal bovine serum (Hyclone, Logan Utah), penicillin/streptomycin (Invitrogen, Carlsbad, Calif.), and 0.001% (v/v) 2-mercaptoethanol (Sigma, St. Louis, Mo.)) on gelatin-coated tissue culture plastic flasks. The cultures were incubated at 37° C. with 5% $CO_2$. For use in experiments, cells were between passages 4 and 12.

Human articular chondrocytes. Human articular chondrocytes were purchased from Cambrex (Walkersville, Md.) and cultured in the same media as the postpartum-derived cells. Twenty-four hours before the experiment, the culture media was changed to a media containing 1% FBS.

Human mesenchymal stem cells (hMSC). MSCs were purchased from Cambrex (Walkersville, Md.) and cultured in MSCGM (Cambrex). Cells used for experiments were between passages 2 and 4.

Collagen gel assays. Cultured cells were trypsinized to remove from culture plate. Cells were washed with centrifugation twice at 300×g for 5 min in DMEM without serum and counted. Cells were mixed with the following components at the final concentrations listed. Rat tail collagen (1 milligram/milliliter, BD DiscoveryLabware, Bedford, Mass.), 0.01 N NaOH and Chondrogenic medium (DMEM, 100 U/100 microgram Penicillin/Streptomycin, 2 millimolar L-Glutamine, 1 millimolar Sodium Pyruvate, 0.35 millimolar L-Proline, 100 nanomolar dexamethasone, 0.17 millimolar L-Ascorbic Acid, 1% (v/v) ITS (insulin, transferrin, selenium) (All components from Sigma Chemical Company)). The cells were gently mixed with the medium the samples were aliquoted into individual wells of a 24 well ultra-low cluster plate (Corning, Corning, N.Y.) at a concentration of either $2 \times 10^5$ per well or $5 \times 10^5$ per well. Cultures were placed in an incubator and left undisturbed for 24-48 hours. Medium was replaced with fresh chondrogenic medium supplemented with appropriate growth factor every 24-48 hours. Samples were allowed to culture for up to 28 days at which time they were removed and fixed in 10% (v/v) formalin (VWR Scientific, West Chester, Pa.) and processed for histological examination. Samples were stained with Safranin O or hematoxylin/eosin for evaluation.

Pellet culture assays. Cultured cells were trypsinized to remove from culture plate. Cells were washed with centrifugation twice at 300×g for 5 minutes in DMEM without serum and counted. Cells were resuspended in fresh chondrogenic medium (described above) at a concentration of $5 \times 10^5$ cells per milliliter. Cells were aliquoted into new polypropylene tubes at $2.5 \times 10^5$ cells per tube. The appropriate samples were then treated with TGF-beta3 (10 nanograms/milliliter, Sigma) or GDF-5 (100 nanograms/milliliter; R&D Systems, Minneapolis, Minn.). Cells were then centrifuged at 150×g for 3 minutes. Tubes were then transferred to the incubator and left undisturbed for 24-48 hours at 37° C. and 5% $CO_2$. Media was replaced with fresh chondrocyte cell media and growth factor, where appropriate, every 2-3 days. Samples were allowed to culture for up to 28 days at which time they were removed and fixed and stained as described above.

Results

Pellets were prepared and cultured and described in Methods. Pellets were grown in media (Control) or supplemented with TGF-beta3 (10 nanograms/milliliter) or GDF-5 (100 nanograms/milliliter) that was replaced every 2-3 days. Pellets collected after 21 days of culture and stained by Safranin O to test for the presence of glycosoaminoglycans. The pellets treated with TGFbeta3 and GDF-5 showed some positive Safranin O staining as compared to control cells. The morphology of the umbilical cord cells showed some limited chondrocyte-like morphology.

Safranin O stains of cell pellets from placenta cells showed similar glycosoaminoglycan expression as compared to the umbilical cord cells. The morphology of the cells also showed some limited chondrocyte-like morphology.

Summary. The results of the present study show that the postpartum-derived cells partially differentiated into chondrocytes in vitro in the pellet culture and the collagen gel assay systems. The postpartum-derived cells showed some indications of glycosoaminoglycan expression by the cells. Morphology showed limited similarity to cartilage tissue.

REFERENCES

1. U.S. Markets for Current and Emerging Orthopedic Biomaterials Products and Technologies. Medtech Insight L.L.C. 2002
2. Johnstone, B, T. M. Hering, A. I. Caplan, V. M. Goldberg and J. U. Yoo. In Vitro Chondrogenesis of Bone-Marrow-Derived Mesenchymal Stem Cells. 1998. Exp Cell Res 238:265-272.
3. Gosiewska, A., A. Rezania, S. Dhanaraj, M. Vyakarnam, J. Zhou, D. Burtis, L. Brown, W. Kong, M. Zimmerman and J. Geesin. Development of a Three-Dimensional Transmigration Assay for Testing Cell-Polymer Interactions for Tissue Engineering Applications. 2001 Tissue Eng. 7:267-277.

Example 16

Evaluation of Chondrogenic Potential of Cells Derived from Postpartum Tissue in an In Vitro Pellet Culture Based Assay This example describes evaluation of the chondrogenic potential of cells derived from placental or umbilical tissue using in vitro pellet culture based assays. Cells from umbilical cord and placenta at early passage (P3) and late passage (P12) were used. The chondrogenic potential of the cells was assessed in pellet culture assays, under chondrogenic induction conditions, in medium supplemented with transforming growth factor beta-3 (TGFbeta-3), GDF-5 (recombinant human growth and differentiation factor 5), or a combination of both.

Materials & Methods

Reagents. Dulbecco's Modified Essential Media (DMEM), Penicillin and Streptomycin, were obtained from Invitrogen, Carlsbad, Calif. Fetal calf serum (FCS) was obtained from HyClone (Logan, Utah). Mesenchymal stem cell growth medium (MSCGM) and hMSC chondrogenic differentiation bullet kit were obtained from Biowhittaker, Walkersville, Md. TGFbeta-3 was obtained from Oncogene research products, San Diego, Calif. GDF-5 was obtained from Biopharm, Heidelberg, Germany (WO9601316 A1, US5994094 A).

Cells. Human mesenchymal stem cells (Lot #2F1656) were obtained from Biowhittaker, Walkersville, Md. and were cultured in MSCGM according to manufacturer's instructions. This lot has been tested previously, and was shown to be positive in the chondrogenesis assays. Human adult and neonatal fibroblasts were obtained from American Type Culture Collection (ATCC), Manassas, Va. and cultured in growth medium (Dulbecco's Modified Essential supplemented with 15% (v/v) fetal bovine serum, penicillin/streptomycin (100 U/100 milligram, respectively) and 0.001% (v/v) 2-mercaptoethanol (Sigma, St. Louis, Mo.) on gelatin-coated tissue culture plastic flasks. Postpartum tissue-derived cells, isolated from human umbilical cords (Lot #022703Umb) and placenta (Lot #071003Plac) as described in previous examples, were utilized. Cells were cultured in Growth medium similar to fibroblasts. The cell cultures were incubated at 37° C. with 5% $CO_2$. Cells used for experiments were at passages 3 and 12.

Pellet culture assay. For pellet cultures, $0.25 \times 10^6$ cells were placed in a 15 milliliter conical tube and centrifuged at 150×g for 5 minutes at room temperature to form a spherical pellet according to protocol for chondrogenic assay from Biowhittaker. Pellets were cultured in chondrogenic induction medium containing TGFbeta-3 (10 nanograms/milliliter), GDF-5 (500 nanograms/milliliter), or a combination of TGFbeta-3 (10 nanograms/milliliter), and GDF-5 (500 nanograms/milliliter) for three weeks. Untreated controls were cultured in growth medium. During culture, pellets were re-fed with fresh medium every other day. Treatment groups included the following:

Treatment Group
A. Placenta-derived cells early passage (P EP)+GDF-5
B. Placenta-derived cells late passage (P LP)+GDF-5
C. Umbilical cord derived cells early passage (U EP)+GDF-5
D. Umbilical cord derived cells late passage (U LP)+GDF-5, n=2
E. Human Mesenchymal Stem cells (HMSC)+GDF-5
F. Human adult fibroblast cells (HAF)+GDF-5
G. Placenta-derived cells early passage (P EP)+TGFbeta-3
H. Placenta-derived cells late passage (P LP)+TGFbeta-3
I. Umbilical cord derived cells early passage (U EP)+TGFbeta-3
J. Umbilical cord derived cells late passage (U LP)+TGFbeta-3, n=2
K. Human Mesenchymal Stem cells (HMSC)+TGFbeta-3
L. Human adult fibroblast cells (HAF)+TGFbeta-3
M. Placenta-derived cells early passage (P EP)+GDF-5+TGFbeta-3, n=1
N. Placenta-derived cells late passage (P LP)+GDF-5+TGFbeta-3
O. Umbilical cord derived cells early passage (U EP)+GDF-5+TGFbeta-3
P. Umbilical cord derived cells late passage (U LP)+GDF-5+TGFbeta-3, n=2
Q. Human Mesenchymal Stem cells (HMSC)+GDF-5+TGFbeta-3
R. Human adult fibroblast cells (HAF)+GDF-5+TGFbeta-3
S. Human neonatal fibroblast cells (HNF)+GDF-5+TGFbeta-3
T. Placenta-derived cells early passage (P EP)
U. Placenta-derived cells late passage (P LP)
V. Umbilical cord derived cells early passage (U EP)
W. Umbilical cord derived cells late passage (U LP)
X. Human Mesenchymal Stem cells (HMSC)
Y. Human adult fibroblast cells (HAF)

Histology of in vitro samples. At the end of the culture period pellets were fixed in 10% buffered formalin and sent to MPI Research (Mattawan, Mich.) for paraffin embedding, sectioning, and staining with Hematoxylin/Eosin (H/E) and Safranin O (SO) staining.

Results

Placenta- and umbilical cord-derived cells, MSCs, and fibroblasts formed cell pellets in chondrogenic induction medium with the different growth factors. The size of the pellets at the end of culture period varied among the different cell types. Pellets formed with placenta-derived cells were similar in size, or slightly larger than, those formed by MSCs and fibroblasts. Pellets formed with the umbilical cord-derived cells tended to be larger and looser than the other groups. Pellets formed with all cell types and cultured in control medium were smaller than pellets cultured in chondrogenic induction medium.

Examination of cross sections of pellets stained with hematoxylin/eosin and Safranin-O showed that umbilical cord-derived cells at early passage had the potential to undergo chondrogenic differentiation. Chondrogenesis as assessed by cell condensation, cell morphology and Safranin O positive staining of matrix was observed in the umbilical cell pellets cultured in chondrogenic induction medium supplemented with TGFbeta-3, GDF-5, or both. Chondrogenesis in pellets was similar for TGFbeta-3, GDF-5, and the combined treatments. Control pellets cultured in growth medium showed no evidence of chondrogenesis. Chondrogenic potential of the umbilical cord derived cells was marginally lower than that observed with the MSCs obtained from Biowhittaker.

Umbilical cord derived cells at late passage and placenta-derived cells did not demonstrate as distinct a chondrogenic potential as did early passage umbilical cord-derived cells. However, this may be due to the fact that chondrogenic induction conditions were optimized for MSCs, not for postpartum-derived cells. Nonetheless, distinct cell populations were observed in placenta-derived cells at both passages located apically or centrally. Some cell condensation was observed with fibroblast, but it was not associated with Safranin O staining.

Example 17

Endothelial Network Formation Assay

Angiogenesis, or the formation of new vasculature, is necessary for the growth of new tissue. Induction of angiogenesis is an important therapeutic goal in many pathological conditions. The present study was aimed at identifying potential angiogenic activity of the postpartum-derived cells in in vitro assays. The study followed a well-established method of seeding endothelial cells onto a culture plate coated with MATRIGEL (BD Discovery Labware, Bedford, Mass.), a basement membrane extract (Nicosia and Ottinetti (1990) In Vitro Cell Dev. Biol. 26(2): 119-28). Treating endothelial cells on MATRIGEL (BD Discovery Labware, Bedford, Mass.) with angiogenic factors will stimulate the cells to form a network that is similar to capillaries. This is a common in vitro assay for testing stimulators and inhibitors of blood vessel formation (Ito et al. (1996) Int. J. Cancer 67(1):148-52). The present studies made use of a co-culture system with the postpartum-derived cells seeded onto culture well inserts. These permeable inserts allow for the passive exchange of media components between the endothelial and the postpartum-derived cell culture media.

Material & Methods

Cell Culture.

Postpartum tissue-derived cells. Human umbilical cords and placenta were received and cells were isolated as previously described (Example 1). Cells were cultured in Growth medium (Dulbecco's Modified Essential Media (DMEM; Invitrogen, Carlsbad, Calif.), 15% (v/v) fetal bovine serum (Hyclone, Logan Utah), 100 Units/milliliter penicillin, 100 microgram/milliliter streptomycin (Invitrogen), 0.001% (v/v) 2-mercaptoethanol (Sigma, St. Louis, Mo.)) on gelatin-coated tissue culture plastic flasks. The cultures were incubated at 37° C. with 5% $CO_2$. Cells used for experiments were between passages 4 and 12.

Actively growing postpartum cells were trypsinized, counted, and seeded onto COSTAR TRANSWELL 6.5 millimeter diameter tissue culture inserts (Corning, Corning, N.Y.) at 15,000 cells per insert. Cells were cultured on the inserts for 48-72 hours in Growth medium at 37° C. under standard growth conditions.

Human mesenchymal stem cells (hMSC). hMSCs were purchased from Cambrex (Walkersville, Md.) and cultured in MSCGM (Cambrex). The cultures were incubated under standard growth conditions.

Actively growing MSCs were trypsinized and counted and seeded onto COSTAR TRANSWELL 6.5 millimeter diameter tissue culture inserts (Corning, Corning, N.Y.) at 15,000 cells per insert. Cells were cultured on the inserts for 48-72 hours in Growth medium under standard growth conditions.

Human umbilical vein endothelial cells (HUVEC). HUVEC were obtained from Cambrex (Walkersville, Md.). Cells were grown in separate cultures in either EBM or EGM endothelial cell media (Cambrex). Cells were grown on standard tissue cultured plastic under standard growth conditions. Cells used in the assay were between passages 4 and 10.

Human coronary artery endothelial cells (HCAEC). HCAEC were purchased from Cambrex Incorporated (Walkersville, Md.). These cells were also maintained in separate cultures in either the EBM or EGM media formulations. Cells were grown on standard tissue cultured plastic under standard growth conditions. Cells used for experiments were between passages 4 and 8.

Endothelial Network Formation (MATRIGEL) assays. Culture plates were coated with MATRIGEL (BD Discovery Labware, Bedford, Mass.) according to manufacturer's specifications. Briefly, MATRIGEL™ (BD Discovery Labware, Bedford, Mass.) was thawed at 4° C. and approximately 250 microliter was aliquoted and distributed evenly onto each well of a chilled 24-well culture plate (Corning). The plate was then incubated at 37° C. for 30 minutes to allow the material to solidify. Actively growing endothelial cell cultures were trypsinized and counted. Cells were washed twice in Growth medium with 2% FBS by centrifugation, resuspension, and aspiration of the supernatant. Cells were seeded onto the coated wells 20,000 cells per well in approximately 0.5 milliliter Growth medium with 2% (v/v) FBS. Cells were then incubated for approximately 30 minutes to allow cells to settle.

Endothelial cell cultures were then treated with either 10 nanomolar human bFGF (Peprotech, Rocky Hill, N.J.) or 10 nanomolar human VEGF (Peprotech, Rocky Hill, N.J.) to serve as a positive control for endothelial cell response. Transwell inserts seeded with postpartum-derived cells were added to appropriate wells with Growth medium with 2% FBS in the insert chamber. Cultures were incubated at 37° C. with 5% $CO_2$ for approximately 24 hours. The well plate was removed from the incubator, and images of the endothelial cell cultures were collected with an Olympus inverted microscope (Olympus, Melville, N.Y.).

Results

In a co-culture system with placenta-derived cells or with umbilical cord-derived cells, HUVEC form cell networks (data not shown). HUVEC cells form limited cell networks in co-culture experiments with hMSC and with 10 nanomolar bFGF (data not shown). HUVEC cells without any treatment showed very little or no network formation (data not shown). These results suggest that the postpartum-derived cells release angiogenic factors that stimulate the HUVEC.

In a co-culture system with placenta-derived cells or with umbilical cord-derived cells, CAECs form cell networks (data not shown).

Table 17-1 shows levels of known angiogenic factors released by the postpartum-derived cells in Growth medium. Postpartum-derived cells were seeded onto inserts as described above. The cells were cultured at 37° C. in atmospheric oxygen for 48 hours on the inserts and then switched to a 2% FBS media and returned at 37° C. for 24 hours. Media was removed, immediately frozen and stored at −80° C., and analyzed by the SEARCHLIGHT multiplex ELISA assay (Pierce Chemical Company, Rockford, IL). Results shown are the averages of duplicate measurements. The results show that the postpartum-derived cells do not release detectable levels of platelet-derived growth factor-bb (PDGF-bb) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

TABLE 17-1

Potential angiogenic factors released from postpartum-derived cells.
Postpartum-derived cells were cultured in 24 hours in media with 2% FBS in atmospheric oxygen.
Media was removed and assayed by the SEARCHLIGHT multiplex ELISA assay (Pierce).
Results are the means of a duplicate analysis. Values are concentrations in the media reported in
picograms per milliliter of culture media.

| | TIMP1 (pg/ml) | ANG2 (pg/ml) | PDGFBB (pg/ml) | TPO (pg/ml) | KGF (pg/ml) | HGF (pg/ml) | FGF (pg/ml) | VEGF (pg/ml) | HBEGF (pg/ml) |
|---|---|---|---|---|---|---|---|---|---|
| Plac (P4) | 91655.3 | 175.5 | <2.0 | 275.5 | 3.0 | 58.3 | 7.5 | 644.6 | <1.2 |
| Plac (P11) | 1592832.4 | 28.1 | <2.0 | 1273.1 | 193.3 | 5960.3 | 34.8 | 12361.1 | 1.7 |
| Umb cord (P4) | 81831.7 | <9.8 | <2.0 | 365.9 | 14.1 | 200.2 | 5.8 | <4.0 | <1.2 |
| Media alone | <9.8 | 25.1 | <2.0 | <6.4 | <2.0 | <3.2 | <5.4 | <4.0 | <1.2 |

Plac: placenta derived cells; Umb cord: Umbilical cord derived cells

Table 17-2 shows levels of known angiogenic factors released by the postpartum-derived cells. Postpartum-derived cells were seeded onto inserts as described above. The cells were cultured in Growth medium at 5% oxygen for 48 hours on the inserts and then switched to a 2% FBS medium and returned to 5% $O_2$ incubation for 24 hours. Media was removed, immediately frozen, and stored at −80° C., and analyzed by the SEARCHLIGHT multiplex ELISA assay (Pierce Chemical Company, Rockford, IL). Results shown are the averages of duplicate measurements. The results show that the postpartum-derived cells do not release detectable levels of platelet-derived growth factor-bb (PDGF-BB) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

TABLE 17-2

Potential angiogenic factors released from postpartum-derived cells.
Postpartum-derived cells were cultured in 24 hours in media with 2% FBS in 5% oxygen.
Media was removed and assayed by the SEARCHLIGHT multiplex ELISA assay (Pierce).
Results are the means of a duplicate analysis.
Values are concentrations in the media reported in picograms per milliliter of culture media.

| | TIMP1 (pg/ml) | ANG2 (pg/ml) | PDGF-BB (pg/ml) | TPO (pg/ml) | KGF (pg/ml) | HGF (pg/ml) | FGF (pg/ml) | VEGF (pg/ml) | HB-EGF (pg/ml) |
|---|---|---|---|---|---|---|---|---|---|
| Plac (P4) | 72972.5 | 253.6 | <2.0 | 743.1 | 2.5 | 30.2 | 15.1 | 1495.1 | <1.2 |
| Plac (P11) | 458023.1 | 55.1 | <2.0 | 2562.2 | 114.2 | 2138.0 | 295.1 | 7521.3 | 1.8 |
| Umb cord (P4) | 50244.7 | <9.8 | <2.0 | 403.3 | 10.7 | 156.8 | 5.7 | <4.0 | <1.2 |
| Media alone | <9.8 | 25.1 | <2.0 | <6.4 | <2.0 | <3.2 | <5.4 | <4.0 | <1.2 |

Plac: placenta derived cells; Umb cord: Umbilical cord derived cells

Summary. The results of the present study show that postpartum-derived cells can stimulate both human umbilical vein and coronary artery endothelial cells to form networks in an in vitro MATRIGEL™ (BD Discovery Labware, Bedford, Mass.) assay. This effect is similar to that seen with known angiogenic factors in this assay system. These results suggest that the postpartum-derived cells are useful for stimulating angiogenesis in vivo.

Example 18

Transplantion of PPDCs

Cells derived from the postpartum umbilical cord and placenta are useful for regenerative therapies. The tissue produced by postpartum-derived cells transplanted into SCID mice with a biodegradable material was evaluated. The materials evaluated were VICRYL non-woven, 35/65 PCL/PGA foam, and RAD 16 self-assembling peptide hydrogel.

Methods & Materials

Cell Culture. Placenta-derived cells and umbilical cord derived cells were grown in Growth medium (DMEM-low glucose (Gibco, Carlsbad Calif.), 15% (v/v) fetal bovine serum (Cat. #SH30070.03; Hyclone, Logan, Utah), 0.001% (v/v) betamercaptoethanol (Sigma, St. Louis, Mo.), 50 Units/milliliter penicillin, 50 microgram/milliliter streptomycin (Gibco)) in a gelatin-coated flasks.

Matrix Preparation. A nonwoven scaffold was prepared using a traditional needle punching technique as described below. Fibers, comprised of a synthetic absorbable copolymer of glycolic and lactic acids (PGA/PLA), sold under the tradename VICRYL were obtained from Ethicon, Inc. (Somerville, N.J.). The fibers were filaments of approximately 20 microns in diameter. The fibers were then cut and crimped into uniform 2-inch lengths to form 2-inch staple fiber. A dry lay needle-punched nonwoven matrix was then prepared utilizing the VICRYL staple fibers. The staple fibers were opened and carded on standard nonwoven machinery. The resulting mat was in the form of webbed staple fibers. The webbed staple fibers were needle-punched to form the dry lay needle-punched nonwoven scaffold. The nonwoven scaffold was rinsed in water followed by another incubation in ethanol to remove any residual chemicals or processing aids used during the manufacturing process.

Foams, composed of 35/65 poly(epsilon-caprolactone)/poly(glycolic acid) (35/65 PCL/PGA) copolymer, werer formed by the process of lyophilized, as discussed in U.S. Pat. No. 6,355,699.

Sample Preparation. One million viable cells were seeded in 15 microliter Growth medium onto 5 millimeter diameter, 2.25 millimeter thick VICRYL non-woven scaffolds (64.33 milligram/cubic centimeters; Lot #3547-47-1) or 5 millimeter diameter 35/65 PCL/PGA foam (Lot #3415-53). Cells were allowed to attach for two hours before adding more Growth medium to cover the scaffolds. Cells were grown on scaffolds overnight. Scaffolds without cells were also incubated in medium.

RAD16 self-assembling peptides (3D Matrix, Cambridge, Mass. under a material transfer agreement) was obtained as a sterile 1% (w/v) solution in water, which was mixed 1:1 with $1 \times 10^6$ cells in 10% (w/v) sucrose (Sigma, St Louis, Mo.), 10 millimolar HEPES in Dulbecco's modified medium (DMEM; Gibco) immediately before use. The final concentration of cells in RAD16 hydrogel was $1 \times 10^6$ cells/100 microliter.

Test Material (N=4/Rx)
1. VICRYL non-woven+$1 \times 10^6$ umbilical cord-derived cells
2. 35/65 PCL/PGA foam+$1 \times 10^6$ umbilical cord-derived cells
3. RAD 16 self-assembling peptide+$1 \times 10^6$ umbilical cord-derived cells
4. VICRYL non-woven+$1 \times 10^6$ placenta-derived cells
5. 35/65 PCL/PGA foam+$1 \times 10^6$ placenta-derived cells
6. RAD 16 self-assembling peptide+$1 \times 10^6$ placenta-derived cells
7. 35/65 PCL/PGA foam
8. VICRYL non-woven Animal Preparation. The animals utilized in this study were handled and maintained in accordance with the current requirements of the Animal Welfare Act. Compliance with the above Public Laws were accomplished by adhering to the Animal Welfare regulations (9 CFR) and conforming to the current standards promulgated in the Guide for the Care and Use of Laboratory Animals, 7th edition.

Mice (*Mus Musculus*)/Fox Chase SCID/Male (Harlan Sprague Dawley, Inc., Indianapolis, Ind.), 5 weeks of age. All handling of the SCID mice took place under a hood. The mice were individually weighed and anesthetized with an intraperitoneal injection of a mixture of 60 milligram/kilogram KETASET (ketamine hydrochloride, Aveco Co., Inc., Fort Dodge, Iowa) and 10 milligram/kilogram ROMPUN (xylazine, Mobay Corp., Shawnee, Kans.) and saline. After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period.

Subcutaneous Implantation Technique. Four skin incisions, each approximately 1.0 cm in length, were made on the dorsum of the mice. Two cranial sites were located transversely over the dorsal lateral thoracic region, about 5-mm caudal to the palpated inferior edge of the scapula, with one to the left and one to the right of the vertebral column. Another two were placed transversely over the gluteal muscle area at the caudal sacro-lumbar level, about 5-mm caudal to the palpated iliac crest, with one on either side of the midline. Implants were randomly placed in these sites. The skin was separated from the underlying connective tissue to make a small pocket and the implant placed (or injected for RAD16) about 1-cm caudal to the incision. The appropriate test material was implanted into the subcutaneous space. The skin incision was closed with metal clips.

Animal Housing. Mice were individually housed in microisolator cages throughout the course of the study within a temperature range of 64° F.-79° F. and relative humidity of 30% to 70%, and maintained on an approximate 12 hour light/12 hour dark cycle. The temperature and relative humidity were maintained within the stated ranges to the greatest extent possible. Diet consisted of Irradiated Pico Mouse Chow 5058 (Purina Co.) and water fed ad libitum.

Mice were euthanized at their designated intervals by carbon dioxide inhalation. The subcutaneous implantation sites with their overlying skin were excised and frozen for histology.

Histology. Excised skin with implant was fixed with 10% neutral buffered formalin (Richard-Allan Kalamazoo, Mich.). Samples with overlying and adjacent tissue were centrally bisected, paraffin-processed, and embedded on cut surface using routine methods. Five-micron tissue sections were obtained by microtome and stained with hematoxylin and eosin (Poly Scientific Bay Shore, N.Y.) using routine methods.

Results

There was minimal ingrowth of tissue into foams implanted subcutaneously in SCID mice after 30 days (data not shown). In contrast there was extensive tissue fill in foams implanted with umbilical-derived cells or placenta-derived cells (data not shown).

There was some tissue in growth in VICRYL non-woven scaffolds. Non-woven scaffolds seeded with umbilical cord- or placenta-derived cells showed increased matrix deposition and mature blood vessels (data not shown).

Summary. The purpose of this study was to determine the type of tissue formed by cells derived from human umbilical cord or placenta in scaffolds in immune deficient mice. Synthetic absorbable non-woven/foam discs (5.0 millimeter diameter×1.0 millimeter thick) or self-assembling peptide hydrogel were seeded with either cells derived from human umbilical cord or placenta and implanted subcutaneously bilaterally in the dorsal spine region of SCID mice. The present study demonstrates that postpartum-derived cells can dramatically increase good quality tissue formation in biodegradable scaffolds.

Example 19

Chondrogenic and Osteogenic Potential of Postpartum-Derived Cells on Implantation in SCID Mice The chondrogenic potential of cells derived from umbilical cord or placenta tissue was evaluated following seeding on bioresorbable growth factor-loaded scaffolds and implantation into SCID mice.

Materials & Methods

Reagents. Dulbecco's Modified Essential Media (DMEM), Penicillin and Streptomycin, were obtained from Invitrogen, Carlsbad, Calif. Fetal calf serum (FCS) was obtained from HyClone (Logan, Utah). Mesenchymal stem cell growth medium (MSCGM) was obtained from Biowhittaker, Walkersville, Md. TGFbeta-3 was obtained from Oncogene research products, San Diego, Calif. GDF-5 was obtained from Biopharm, Heidelberg, Germany (International PCT Publication No. WO96/01316 A1, U.S. Pat. No. 5,994,094A). Chondrocyte growth medium comprised DMEM-High glucose supplemented with 10% fetal calf serum (FCS), 10 milliMolar HEPES, 0.1 milliMolar nonessential amino acids, 20 microgram/milliliter L-proline, 50 microgram/milliliter ascorbic acid, 100 Unit/milliliter penicillin, 100 microgram/milliliter streptomycin, and 0.25 microgram/milliliter amphotericin B. Bovine fibrinogen was obtained from Calbiochem.

Cells. Human mesenchymal stem cells (hMSC, Lot #2F1656) were obtained from Biowhittaker, Walkersville, Md. and were cultured in MSCGM according to the manufacturer's instructions. This lot was tested in the laboratory previously in in vitro experiments and was shown to be positive in the chondrogenesis assays. Human adult fibroblasts were obtained from American Type Culture Collection (ATCC), Manassas, Va. and cultured in Growth Medium on gelatin-coated tissue culture plastic flasks. Postpartum-derived cells isolated from human umbilical cords (Lot #022703Umb) and placenta (Lot #071003Plac) were prepared as previously described (Example 1). Cells were cultured in Growth medium on gelatin-coated tissue culture plastic flasks. The cell cultures were incubated in standard growth conditions. Cells used for experiments were at passages 5 and 14.

Scaffold. 65/35 Polyglycolic acid (PGA)/Polycaprolactone (PCL) foam scaffolds[4×5 centimeters, 1 millimeter thick, Ethylene Oxide (ETO) sterilized] reinforced with Polydioxanone (PDS) mesh (PGA/PCL foam-PDS mesh) were obtained from Center for Biomaterials and Advanced Technologies (CBAT, Somerville, N.J.). Punches (3.5 millimeters) made from scaffolds were loaded with either GDF-5 (3.4 micrograms/scaffold), TGFbeta-3 (10 nanograms/scaffold), a combination of GDF-5 and TGFbeta-3, or control medium, and lyophilized.

Cell seeding on scaffolds. Placenta- and umbilical cord-derived cells were treated with trypsin, and cell number and viability was determined. $0.75 \times 10^6$ cells were resuspended in 15 microliter of Growth Medium and seeded onto 3.5 millimeter scaffold punches in a cell culture dish. The cell-seeded scaffold was incubated in a cell culture incubator in standard air with 5% $CO_2$ at 37° C. for 2 hours after which they were placed within cartilage explant rings.

Bovine Cartilage Explants. Cartilage explants 5 millimeter in diameter were made from cartilage obtained from young bovine shoulder. Punches (3 millimeter) were excised from the center of the explant and replaced with cells seeded 3.5 millimeter resorbable scaffold. Scaffolds with cells were retained within the explants using fibrin glue (60 microliter of bovine fibrinogen, 3 milligram/milliliter). Samples were maintained in chondrocyte growth medium overnight, rinsed in Phosphate Buffered Saline the following day, and implanted into SCID mice.

Animals. SCID mice ((*Mus musculus*)/Fox Chase SCID/Male), 5 weeks of age, were obtained from Harlan Sprague Dawley, Inc. (Indianapolis, Ind.) and Charles River Laboratories (Portage, Mich.). Animals used in the study were selected without any apparent systematic bias. A tag was placed on each individual animal cage listing the accession number, implantation technique, animal number, species/strain, surgery date, in vivo period, and date of euthanasia. The animals were identified by sequential numbers marked on the ear with an indelible ink marker.

Experimental Design. A total of 42 mice were tested. Two scaffolds were implanted subcutaneously in each mouse as described below; 42 mice for subcutaneous implantation; 28 treatments with n-value of 3 per treatment. The study corresponds to IACUC Approval Number: Skillman IACUC 01-037. The study lasted six weeks.

SCID Implantation.

A. Body Weights

Each animal was weighed prior to being anesthetized and at necropsy.

B. Anesthesia and Surgical Preparation:

All handling of the SCID mice occurred under a hood. The mice were individually weighed and anesthetized with an intraperitoneal injection of a mixture of KETASET (ketamine hydrochloride[60 milligram/kilogram]), ROMPUN (xylazine[10 milligram/kilogram]), and saline.

After induction of anesthesia, the entire back of the animal from the dorsal cervical area to the dorsal lumbosacral area was clipped free of hair using electric animal clippers. The area was scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period. The anesthetized and surgically prepared animal was placed in the desired recumbent position.

C. Subcutaneous Implantation Technique:

An approximate 2-cm skin incision was made just lateral to the thoracic spine parallel to the vertebral column. The skin was separated from the underlying connective tissue via blunt dissection. Each SCID mouse received 2 treatments that were placed in subcutaneous pockets created by blunt dissection in each hemithorax through one skin incision. Tacking sutures of 5-0 ETHIBOND EXCEL (polyester) were used to tack the skin to musculature around each scaffold to prevent subcutaneous migration. Scaffolds were implanted for 6 weeks and then harvested. The experimental design is outlined in Table 19-1.

TABLE 19-1

| | Experimental Design: Treatment (N = 3 per treatment) |
|---|---|
| A. | 65/35 PGA/PCL Foam + PDS mesh cultured with Placenta-derived cells, EP, TGFbeta3 |
| B. | 65/35 PGA/PCL Foam + PDS mesh cultured with Placenta-derived cells, EP, rhGDF-5 |
| C. | 65/35 PGA/PCL Foam + PDS mesh cultured with Placenta-derived cells, EP, rhGDF-5 + TGFbeta3 |
| D. | 65/35 PGA/PCL Foam + PDS mesh cultured with Placenta-derived cells, EP, control |
| E. | 65/35 PGA/PCL Foam + PDS mesh cultured with Placenta-derived cells, LP, TGFbeta3 |
| F. | 65/35 PGA/PCL Foam + PDS mesh cultured with Placenta-derived cells, LP, rhGDF-5 |
| G. | 65/35 PGA/PCL Foam + PDS mesh cultured with Placenta-derived cells, LP, rhGDF-5 + TGFbeta3 |
| H. | 65/35 PGA/PCL Foam + PDS mesh cultured with Placenta-derived cells, LP, control |
| I. | 65/35 PGA/PCL Foam + PDS mesh cultured with Umbilical cord-derived cells, EP, TGFbeta3 |
| J. | 65/35 PGA/PCL Foam + PDS mesh cultured with Umbilical cord-derived cells, EP, rhGDF-5 |
| K. | 65/35 PGA/PCL Foam + PDS mesh cultured with Umbilical cord-derived cells, EP, rhGDF-5 + TGFbeta3 |
| L. | 65/35 PGA/PCL Foam + PDS mesh cultured with Umbilical cord-derived cells, EP, control |
| M. | 65/35 PGA/PCL Foam + PDS mesh cultured with Umbilical cord-derived cells, LP, TGFbeta3 |
| N. | 65/35 PGA/PCL Foam + PDS mesh cultured with Umbilical cord-derived cells, LP, rhGDF-5 |
| O. | 65/35 PGA/PCL Foam + PDS mesh cultured with Umbilical cord-derived cells, LP, rhGDF-5 + TGFbeta3 |
| P. | 65/35 PGA/PCL Foam + PDS mesh cultured with Umbilical cord-derived cells, LP, control |
| Q. | 65/35 PGA/PCL Foam + PDS mesh cultured with hMSC, TGFbeta3 |
| R. | 65/35 PGA/PCL Foam + PDS mesh cultured with hMSC, rhGDF-5 |
| S. | 65/35 PGA/PCL Foam + PDS mesh cultured with hMSC, rhGDF-5 + TGFbeta3 |
| T. | 65/35 PGA/PCL Foam + PDS mesh cultured with hMSC, control |
| U. | 65/35 PGA/PCL Foam + PDS mesh cultured with fibroblasts, Adult TGFbeta3 |

TABLE 19-1-continued

Experimental Design: Treatment (N = 3 per treatment)

| | |
|---|---|
| V. | 65/35 PGA/PCL Foam + PDS mesh cultured with fibroblasts, Adult rhGDF-5 |
| W. | 65/35 PGA/PCL Foam + PDS mesh cultured with fibroblasts, Adult rhGDF-5 + TGFbeta3 |
| X. | 65/35 PGA/PCL Foam + PDS mesh cultured with fibroblasts, Adult control |
| Y. | 65/35 PGA/PCL Foam + PDS mesh, TGFbeta3 |
| Z. | 65/35 PGA/PCL Foam + PDS mesh, rhGDF-5 |
| AA. | 65/35 PGA/PCL Foam + PDS mesh, rhGDF-5 + TGFbeta3 |
| BB. | 65/35 PGA/PCL Foam + PDS mesh, control |

D. Necropsy and Histologic Preparation

Gross examination was performed on any animals that died during the course of the study or were euthanized in moribund condition. Selected tissues were saved at the discretion of the study director and/or pathologist.

Mice were euthanized by $CO_2$ inhalation at their designated intervals. Gross observations of the implanted sites were recorded. Samples of the subcutaneous implantation sites with their overlying skin were excised and fixed in 10% buffered formalin. Each implant was bisected into halves, and one half was sent to MPI Research (Mattawan, Mich.) for paraffin embedding, sectioning, and staining with Hematoxylin & Eosin (H & E) and Safranin O (SO).

The data obtained from this study were not statistically analyzed.

Results

New cartilage and bone formation was observed in the majority of the samples including growth factor-loaded, cell-seeded scaffolds, cell-seeded control scaffolds, and scaffolds loaded with growth factor alone. The extent of new cartilage and bone formation varied within the treatment and control groups.

Early and Late passage placenta-derived cell seeded scaffolds showed new cartilage and bone formation within the scaffolds. No obvious differences in new cartilage and bone formation was observed between the different growth factor-loaded, cell-seeded scaffolds and scaffolds seeded with cells alone. Compared to control scaffolds (without growth factors and without cells), it appeared that there was greater extent of new cartilage formation in cell-seeded scaffolds both with and without growth factors and in growth factor-loaded scaffolds alone. New cartilage formation with placenta-derived cell-seeded scaffolds was similar to MSC- and fibroblast-seeded scaffolds.

In growth factor-treated and control scaffolds seeded with umbilical cord-derived cells at early and late passage, new cartilage and bone formation were observed. The extent of cartilage formation appeared to be less than that seen with placenta-derived cells. No one sample showed extensive cartilage formation as seen with the placenta-derived cells. Bone formation appeared to be higher in scaffolds seeded with umbilical cord-derived cells on scaffolds containing both TGFbeta-3 and rhGDF-5.

hMSC-loaded scaffolds also showed new cartilage and bone formation. The extent of new cartilage and bone formation was similar for all the hMSC treatment groups. Human adult fibroblast seeded scaffolds also demonstrated new cartilage and bone formation. Results were similar to those obtained with placenta-derived cells and hMSCs In the control group, in which growth factor-loaded scaffolds or scaffold alone were placed in cartilage rings and implanted, new cartilage and bone formation were also observed. Not surprisingly, the extent of new cartilage formation was greater in scaffolds with growth factor than in scaffolds without growth factor. Increased bone formation was present in the control with the combination of the two tested growth factors.

New cartilage formation was observed adjacent to the cartilage explant rings as well as within the scaffolds. New cartilage formation within the scaffolds adjacent to the cartilage rings could be a result of chondrocyte migration. Cartilage formation seen as islands within the scaffolds may be a result of either migration of chondrocytes within the scaffolds, differentiation of seeded cells or differentiation of endogenous mouse progenitor cells. This observation stems from the fact that in control growth factor-loaded scaffolds with no seeded cells, islands of chondrogenic differentiation were observed. New bone formation was observed within the scaffolds independently and also associated with chondrocytes. Bone formation may have arisen from osteoblast differentiation as well as endochondral ossification.

It is difficult to separate new cartilage and bone formation associated with chondrocytes that migrated versus that from any chondrogenic and osteogenic differentiation of seeded cells that may have occurred. Staining of sections with specific human antibodies may distinguish the contribution of the seeded cells to the observed chondrogenesis and osteogenesis. It is also possible that placenta-derived cells and umbilical cord-derived cells stimulated chondrocyte migration.

Abundant new blood vessels were observed with the scaffolds loaded with placenta-derived cells and umbilical cord-derived cells. Blood vessels were abundant in areas of bone formation. New blood vessels were also observed within the hMSC- and fibroblast-seeded scaffolds associated with new bone formation.

Systemic effects of the adjacent scaffold (with growth factor (GF)) on the control scaffolds (no GF, no cells) on promoting new cartilage and bone formation cannot be ruled out. Analysis of new cartilage and bone formation in scaffolds, taking into consideration the scaffolds implanted adjacent to it in SCID mice, showed no clear pattern of systemic effect of growth factor from the adjacent scaffold.

Summary. Results showed that new cartilage and bone formation were observed in growth factor and control scaffolds seeded with placenta- and umbilical cord-derived cells. Results with placenta-derived cells were similar to that seen with human mesenchymal stem cells, while the extent of new cartilage like tissue formation was slightly less pronounced in umbilical cord-derived cells. Growth factor-loaded scaffolds implanted without cells also demonstrated new cartilage and bone formation. These data indicate that new cartilage formation within the scaffolds may arise from chondrocytes that migrated from the bovine explants, from chondrogenic differentiation of endogenous progenitor cells, and from chondrogenic differentiation of seeded cells.

These results suggest that placenta- and umbilical cord-derived cells undergo chondrogenic and osteogenic differentiation. These results also suggest that placenta- and umbilical cord-derived cells may promote migration of chondrocytes from the cartilage explant into the scaffolds. Abundant new blood vessels were also observed in the scaffolds especially associated with new bone formation.

While the present invention has been particularly shown and described with reference to the presently preferred embodiments, it is understood that the invention is not limited to the embodiments specifically disclosed and exemplified herein. Numerous changes and modifications may be made to the preferred embodiment of the invention, and such changes and modifications may be made without departing from the scope and spirit of the invention as set forth in the appended claims.

What is claimed:

1. A method of forming cartilage in a patient, said method comprising administering to said patient a matrix comprising a homogeneous population of undifferentiated umbilical cord tissue-derived cells, wherein the homogeneous population of cells is obtained from human postpartum umbilical cord substantially free of blood, and wherein said homogeneous population of cells:
  i) exhibits increased expression, relative to a human cell that is a fibroblast, a mesenchymal stem cell, or an iliac crest bone marrow cell, of an endogenous gene encoding interleukin 8 and an endogenous gene encoding reticulon 1;
  ii) secretes MCP-1, IL-6, IL-8, GCP-2, HGF, KGF, FGF, HB-EGF, BDNF, TPO, MIP1b, RANTES and TIMP 1;
  iii) produces CD10, CD13, CD44, CD73, CD90, PDGFr-alpha, and HLA-A, B, C; and
  iv) lacks production of CD31, CD34, CD117, CD141, and HLA-DR, DP, DQ,
  whereby cartilage is formed in the matrix.

2. The method of claim 1 wherein said matrix is implanted into said patient.

3. The method of claim 1 wherein said matrix comprises at least one bioactive factor.

4. The method of claim 1 wherein said matrix is administered to a bone of said patient.

5. The method of claim 1 wherein said matrix is administered to cartilage of said patient.

6. The method of claim 1 wherein said homogeneous cell population is capable of self-renewal and expansion in culture, has the potential to differentiate into cells of a chondrogenic phenotype, and requires L-valine for growth.

7. The method of claim 1 wherein said homogeneous cell population has the potential for at least 40 doublings in culture.

8. The method of claim 1 wherein said homogeneous cell population does not express any of CD80, CD86, CD178, or HLA-G.

9. The method of claim 1 wherein said homogeneous cell population expresses a gene for each of chemokine (C-X-C motif) ligand 1(melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3.

10. The method of claim 1 wherein said homogeneous cell population does not secrete any of the factors SDF-1alpha, TGF-beta2, ANG2, PDGFbb, MIP1a and VEGF.

11. The method of claim 1 wherein said homogeneous cell population is obtained by contacting umbilical cord tissue with an enzyme solution comprising a matrix metalloprotease, a neutral protease and a mucolytic enzyme.

12. A method of forming cartilage in a patient, said method comprising administering to said patient a matrix comprising a homogeneous population of undifferentiated umbilical cord tissue-derived cells, wherein said homogenous population of cells is deposited with ATCC under Accession No. PTA-6067, whereby cartilage is formed in the matrix.

13. A method of forming cartilage in a patient, said method comprising administering to said patient a matrix comprising a homogeneous population of undifferentiated umbilical cord tissue-derived cells, wherein said homogenous population of cells is deposited with ATCC under Accession No. PTA-6068, whereby cartilage is formed in the matrix.

14. The method of claim 12, wherein the homogeneous population of undifferentiated umbilical cord tissue-derived cells has the potential to differentiate into cells of a chondrogenic phenotype.

15. The method of claim 13, wherein the homogeneous population of undifferentiated umbilical cord tissue-derived cells has the potential to differentiate into cells of a chondrogenic phenotype.

* * * * *